(12) United States Patent
Speicher et al.

(10) Patent No.: US 10,338,076 B2
(45) Date of Patent: Jul. 2, 2019

(54) METHODS AND COMPOSITIONS FOR THE DIAGNOSIS OF OVARIAN CANCER

(71) Applicant: The Wistar Institute of Anatomy and Biology, Philadelphia, PA (US)

(72) Inventors: David W. Speicher, Berwyn, PA (US); Hsin Yao Tang, Media, PA (US); Lynn A. Beer, Medford, NJ (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 15/884,691

(22) Filed: Jan. 31, 2018

(65) Prior Publication Data

US 2018/0231559 A1    Aug. 16, 2018

Related U.S. Application Data

(62) Division of application No. 14/045,452, filed on Oct. 3, 2013, now Pat. No. 9,903,870.

(60) Provisional application No. 61/709,695, filed on Oct. 4, 2012.

(51) Int. Cl.
| | |
|---|---|
| *G01N 33/574* | (2006.01) |
| *C12Q 1/6886* | (2018.01) |
| *G01N 33/68* | (2006.01) |
| *C07K 16/30* | (2006.01) |
| *C40B 40/06* | (2006.01) |
| *C40B 40/10* | (2006.01) |

(52) U.S. Cl.
CPC ... *G01N 33/57449* (2013.01); *C07K 16/3069* (2013.01); *C12Q 1/6886* (2013.01); *G01N 33/6887* (2013.01); *C40B 40/06* (2013.01); *C40B 40/10* (2013.01); *G01N 2333/4712* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,745,149 B2 | 6/2010 | Chow |
| 2006/0063162 A1 | 3/2006 | Deng |
| 2007/0099209 A1* | 5/2007 | Clarke et al. ........ C12Q 1/6886 435/6.12 |
| 2007/0172900 A1 | 7/2007 | Cahill |
| 2009/0258002 A1* | 10/2009 | Barrett et al. ....... C12Q 1/6886 424/130.1 |
| 2009/0275608 A1 | 11/2009 | Ossovskaya |
| 2010/0016173 A1 | 1/2010 | Nagalla |
| 2011/0287034 A1 | 11/2011 | Frank |
| 2012/0214685 A1 | 8/2012 | Speicher |
| 2014/0228233 A1 | 8/2014 | Pawlowski |

FOREIGN PATENT DOCUMENTS

| | | | |
|---|---|---|---|
| EP | 2107127 | 10/2009 | |
| WO | WO 2000/061636 | 10/2000 | |
| WO | WO-2011068839 A1 * | 6/2011 | .......... C12Q 1/6886 |
| WO | WO 2013/036754 | 3/2013 | |

OTHER PUBLICATIONS

Anderson, L.; Hunter, C. L., "Quantitative mass spectrometric multiple reaction monitoring assays for major plasma proteins", Mol Cell Proteomics, Apr. 2006, p. 573-588 vol. 5, No. 4 (epublished Dec. 6, 2005).

Alaiya, A. et al., Phenotypic Analysis of Ovarian Carcinoma: Polypeptide Expression in Benign, Borderline and Malignant Tumors, International Journal of Cancer, Nov. 1997, 73(5): 678-683.

Alaiya, A. et al., Polypeptide Expression in Prostate Hyperplasia and Prostate Adenocarcinoma, Analytical Cellular Pathology, Oct. 2000, 21: 1-9.

Anastasi, E. et al, "HE4: A new potential early biomarker for the recurrence of ovarian cancer", Tumour Biol, Jan. 2010, vol. 31 No. 2, p. 113-119.

Anderson NL and Anderson NG. The human plasma proteome: history, character, and diagnostic prospects. Molecular & Cellular Proteomics. Oct. 2002;1(11):845-67.

Anderson NL. The clinical plasma proteome: a survey of clinical assays for proteins in plasma and serum. Clinical Chemistry. Nov. 2009;56(2):177-85.

(Continued)

*Primary Examiner* — Kaijiang Zhang

(74) *Attorney, Agent, or Firm* — Howson & Howson LLP

(57) ABSTRACT

A diagnostic reagent or device comprises at least one ligand capable of specifically complexing with, binding to, or quantitatively detecting or identifying the biomarker chloride intracellular channel protein 4 (CLIC4) or an isoform, pro-form, modified molecular form including posttranslational modification, or unique peptide fragment or nucleic acid fragment thereof. An alternative diagnostic reagent or device comprises ligand or ligands capable of specifically complexing with, binding to, or quantitatively detecting or identifying multiple tropomyosin biomarkers. Optionally, such reagent or device includes a signaling molecule and/or a substrate on which the ligand is immobilized. Other reagents and methods of diagnosing ovarian cancer include use of CLIC4 ligands and/or multiple tropomyosin ligands with an additional ovarian cancer biomarker. For example, CLIC4 combined with one or more of CLIC1 and/or one or multiple members of the tropomyosin family, e.g., TPM1, TPM2, TPM3 or TPM4, and further optionally including CTSD-30 kDa and/or PRDX-6, among other ovarian cancer biomarkers can form a characteristic diagnostic pattern or profile of expression that is diagnostic of the disease. Still other embodiments are described.

12 Claims, 6 Drawing Sheets

Specification includes a Sequence Listing.

(56) References Cited

OTHER PUBLICATIONS

Anderson NL. The roles of multiple proteomic platforms in a pipeline for new diagnostics. Molecular & Cellular Proteomics. Jul. 2005;4(10):1441-4.
Beer, L. A. et al., "Systematic discovery of ectopic pregnancy serum biomarkers using 3-D protein profiling coupled with label-free quantitation", J Proteome Res, Mar. 2011, p. 1126-1138 vol. 10 No. 3.
Bengtsson, S. et al, "Large-scale proteomics analysis of human ovarian cancer for biomarkers", J Proteome Res, Feb. 2007, vol. 6 No. 4, p. 1440-1450.
Bjorhall K, et al. Comparison of different depletion strategies for improved resolution in proteomic analysis of human serum samples. Proteomics. Jan. 2005;5(1):307-17.
Byrjalsen, I. et al., Two-Dimensional Gen Analysis of Human Endometrial Proteins: Characterization of Proteins with Increased Expression in Hyperplasia and Adenocarcinoma, Molecular Human Reproduction, Jun. 1999, 5(8): 748-756.
Cannistra, S. A., "Cancer of the ovary", N Engl J Med, Dec. 2004, vol. 351 No. 24, p. 2519-2529.
Chang, Y.H. et al., Cell Secretome Analysis Using Hollow Fiber Culture System Leads to the Discovery of CLIC1 Protein as a Novel Plasma Marker for Nasopharyngeal Carcinoma, Journal of Proteome, May 2009, 8: 5465-5474.
Chen, C.D. et al., Overexpression of CLIC1 in Human Gastric Carcinoma and Its Clinicopathological Significance, Proteomics, Sep. 2006, 7: 155-167.
Choi, C. et al, "From skeletal muscle to cancer: insights learned elucidating the function of tropomyosin", J Struct Biol, Nov. 2012, vol. 177 No. 1, p. 63-69.
Choi, H. et al., Tropomyosin3 Overexpression and a Potential Link To Epithelial-Mesenchymal Transition in Human Hepatocellular Carcinoma, BMC Cancer, Apr. 2010, 10(122): 1-11.
Chow, S. N. et al., "Analysis of protein profiles in human epithelial ovarian cancer tissues by proteomic technology", Eur J Gynaecol Oncol, Apr. 2010, vol. 31 No. 1, p. 55-62.
Dai, L. et al,"Comparative proteomic study of two closely related ovarian endometrioid adenocarcinoma cell lines using cIEF fractionation and pathway analysis", Electrophoresis, Apr. 2009, p. 1119-1131 vol. 30 No. 7.
Domon, B.; Aebersold, R., "Options and considerations when selecting a quantitative proteomics strategy", Nat Biotechnol, Jul. 2010, vol. 28 No. 7, p. 710-721.
Duncan, M. W. et al, "Quantifying proteins by mass spectrometry: The selectivity of SRM is only part of the problem", Proteomics, Mar. 2009, p. 1124-1127 vol. 9 No. 5.
Echan LA & Speicher DW. Immunoaffinity depletion of high abundance plasma and serum proteims the Protein Protocols Handbook, 3rd ed. Oct. 2009. pp. 139-153.
Echan LA et al., Depletion of multiple high-abundance proteins improves protein profiling capacities of human serum and plasma. Proteomics, Aug. 2005; 5(13):3292-303.
Elliott MH, et al. Current trends in quantitative proteomics. Journal of Mass Spectrometry. Dec. 2009;44(12):1637-60.
Faca, V. M. et al, "Proteomic analysis of ovarian cancer cells reveals dynamic processes of protein secretion and shedding of extracellular domains", PLoS One, Jun. 2008, p. e2425 vol. 3 No. 6.
Fang Y, et al. Quantitative analysis of proteome coverage and recovery rates for upstream fractionation methods in proteomics. Journal of Proteome Research. Apr. 2010;9(4):1902-12. (e-publication Jan. 16, 2010).
Gagne, J. P. et al, "Proteome profiling of human epithelial ovarian cancer cell line TOV-112D", Mol Cell Biochem, Dec. 2004, vol. 275 No. 1-2, p. 25-55.
Garcia-Blanco, M. A. et al, "Alternative splicing in disease and therapy", Nat Biotechnol, May 2004, p. 535-546 vol. 22 No. 5.

Gortzak-Uzan, L. et al, "A proteome resource of ovarian cancer ascites: integrated proteomic and bioinformatic analyses to identify putative biomarkers", J Proteome Res, Dec. 2007, vol. 7 No. 1, p. 339-351.
Gunawardana, C. G. et al., "Comprehensive analysis of conditioned media from ovarian cancer cell lines identifies novel candidate markers of epithelial ovarian cancer", J Proteome Res, Aug. 2009, vol. 8 No. 10, p. 4705-4713.
Gunning, P. W. et al, "Tropomyosin isoforms: divining rods for actin cytoskeleton function", Trends Cell Biol, Jun. 2005, p. 333-341 vol. 15 No. 6.
He, Q. Y. et al., Diverse Proteomic Alterations in Gastric Adenocarcinoma, Proteomics, May 2004, 4: 3276-3287.
He, Y. et al, "LC-MS/MS analysis of ovarian cancer metastasis-related proteins using a nude mouse model: 14-3-3 zeta as a candidate biomarker", J Proteome Res, Sep. 2010, vol. 9 No. 12, p. 6180-6190.
Helfman, D. M.; Flynn, P.; Khan, P.; Saeed, A., "Tropomyosin as a regulator of cancer cell transformation", Adv Exp Med Biol, 2008, vol. 644, p. 124-131.
Hellman, K. et al., Differential Tissue-Specific Protein Markers of Vaginal Carcinoma, British Journal of Cancer, Mar. 2009, 100: 1303-1314.
Hu, X.T. et al., The Proteasome Subunit PSMA7 Located on the 20q13 Amplicon is Overexpressed and Associated With Liver Metastasis in Colorectal Cancer, Oncology Reports, Nov. 2007, 19(2): 441-446.
Keller A, et al. Empirical statistical model to estimate the accuracy of peptide identifications made by MS/MS and database search. Analytical Chemistry, Oct. 2002;74(20):5383-92.
Klug, T. L. et al, "Monoclonal antibody immunoradiometric assay for an antigenic determinant (CA 125) associated with human epithelial ovarian carcinomas", Cancer Res, Mar. 1984, p. 1048-1053 vol. 44 No. 3.
Kriventseva, E. V. et al, "Increase of functional diversity by alternative splicing", Trends Genet, Mar. 2003, vol. 19 No. 3, p. 124-128.
Kuk, C. et al, "Mining the ovarian cancer ascites proteome for potential ovarian cancer biomarkers", Mol Cell Proteomics, Apr. 2009, p. 661-669 vol. 8 No. 4 (epublished Dec. 1, 2008).
Lo, W. Y. et al., Identification of Over-Expressed Proteins in Oral Squamous Cell Carcinoma (OSCC) Patients by Clinical Proteomic Analysis, Clinica Chimica Acta, Jun. 2006, 376(1-2): 101-107.
Lomnytska, M.I. et al., Diagnostic Protein Marker Patterns in Squamous Cervical Cancer, Proteomics Clinical Applications, Jan. 2010, 4(1): 17-31.
Lomnytska, M.I. et al., Differential Expression of ANXA6, HSP27, PRDX2, NCF2, and TPM4 During Uterine Cervix Carcinogenesis: Diagnostic and Prognostic Value, British Journal of Cancer, Nov. 2010, 104: 110-119.
Losch, A. et al, "Cathepsin D in ovarian cancer: prognostic value and correlation with p53 expression and microvessel density", Gynecologic Oncology, Feb. 2004, p. 545-552 vol. 92 No. 2.
Lu, H. et al, "Targeting serum antibody for cancer diagnosis: a focus on colorectal cancer", Expert Opin Ther Targets, Feb. 2007, vol. 11 No. 2, p. 235-244.
Molecular Target for Cancer Therapy, The Journal of Investigative Dermatology, Nov. 2005, 10(2): 105-109.
Moore, R. G. et al, "Comparison of a novel multiple marker assay vs the Risk of Malignancy Index for the prediction of epithelial ovarian cancer in patients with a pelvic mass", AM J Obstet Gynecol, Sep. 2010, p. 228 el-6 vol. 203 No. 3.
Moss, E. L. et al, "The role of CA125 in clinical practice", J Clin Pathol, Mar. 2005, p. 308-312 vol. 58 No. 3.
Mueller LN, et al. An assessment of software solutions for the analysis of mass spectrometry based quantitative proteomics data. Journal of Proteome Research. Jan. 2008;7(1):51-61.
Mutch, D. G., "Surgical management of ovarian cancer", Semin Oncol, Feb. 2002, vol. 29 No. 1, Suppl 1, p. 3-8.
Nesvizhskii AI, et al. A statistical model for identifying proteins by tandem mass spectrometry. Analytical Chemistry, Sep. 2003;75(17):4646-58.

(56) References Cited

OTHER PUBLICATIONS

Nesvizhskii, A. I.; Aebersold, R., "Interpretation of shotgun proteomic data: the protein inference problem", Mol Cell Proteomics, Oct. 2005, p. 1419-1440 vol. 4 No. 10.
Neubert H, et al. Label-free detection of differential protein expression by LC/MALDI mass spectrometry. Journal of Proteome Research. Jun. 2008;7(6):2270-9.
Nick, A. M.; Sood, A. K., "The ROC 'n' role of the multiplex assay for early detection of ovarian cancer", Nat Clin Pract Oncol, Oct. 2008, vol. 5 No. 10, p. 568-569.
Old WM, et al. Comparison of label-free methods for quantifying human proteins by shotgun proteomics. Molecular & Cellular Proteomics. Jun. 2005;4(10):1487-502.
Omenn GS, et al. Overview of the HUPO Plasma Proteome Project: results from the pilot phase with 35 collaborating laboratories and multiple analytical groups, generating a core dataset of 3020 proteins and a publicly-available database. Proteomics. May 2005;5(13):3226-45.
Paweletz CP, et al. Application of an end-to-end biomarker discovery platform to identify target engagement markers in cerebrospinal fluid by high resolution differential mass spectrometry. Journal of Proteome Research. Mar. 2010;9(3):1392-401. (e-publication Jan. 24, 2010).
Petrova, D.T. et al., Expression of Chloride Intracellular Channel Protein 1 (CLIC1) and Tumor Protein D52 (TPD52) as Potential Biomarkers for Colorectal Cancer, Clinical Biochemistry, Oct. 2008, 41(14-15): 1224-1236.
Piersma SR, et al. Workflow comparison for label-free, quantitative secretome proteomics for cancer biomarker discovery: method evaluation, differential analysis, and verification in serum. Journal of Proteome Research. Apr. 2010;9(4):1913-22. (e-publication Jan. 19, 2010).
Pitteri, S. J. et al, "Integrated proteomic analysis of human cancer cells and plasma from tumor bearing mice for ovarian cancer biomarker discovery", PLoS One, Nov. 2009, p. e7916 vol. 4 No. 11.
Raval, G. N. et al, "Loss of expression of tropomyosin-1, a novel class II tumor suppressor that induces anoikis, in primary breast tumors", Oncogene, Sep. 2003, p. 6194-6203 vol. 22, No. 40.
Rifai N and Gillette MA. Protein biomarker discovery and validation: the long and uncertain path to clinical utility. Nature Biotechnology. Aug. 2006; 24(8):971-83.
Rodriguez-Pineiro, A. M. et al, "Differential expression of serum clusterin isoforms in colorectal cancer", Mol Cell Proteomics, Sep. 2006, p. 1647-1657 vol. 5 No. 9.
Romanuik, T.L. et al., Novel Biomarkers for Prostate Cancer Including Noncoding Transcripts, The American Journal of Pathology, Dec. 2009, 176(6): 2264-2276.
Rostila, A. et al, "Peroxiredoxins and tropomyosins as plasma biomarkers for lung cancer and asbestos exposure", Lung Cancer, Mar. 2012, vol. 77 No. 2, p. 450-459
Scotto, L. et al., Identification of Copy Number Gain and Overexpressed Genes on Chromosome Arm 20q by an Integrative Genomic Approach in Cervical Cancer: Potential Role in Progression, Genes, Chromosomes & Cancer, May 2008, 47(9): 755-765.
Shen, J. et al., Protein Expression Profiles in Pancreatic Adenocarcinoma Compared with Normal Pancreatic Tissue and Tissue Affected by Pancreatitis as Detected by Two-Dimensional Gel Electrophoresis and Mass Spectrometry, Cancer Research, Dec. 2004, 64: 9018-9026.
Sherman, J. et al, "How specific is my SRM?: The issue of precursor and product ion redundancy", Proteomics, Mar. 2009, p. 1120-1123 vol. 9 No. 5.
Shi, Z.H. et al., CLIC1 Protein: A Candidate Prognostic Biomarker for Malignant-Transformed Hydatidiform Moles, International Journal of Gynecological Cancer, Jan. 2011, 21(1): 153-160.
Shukla, A.; Yuspa, S. H., "CLIC4 and Schnurri-2: a dynamic duo in TGF-beta signaling with broader implications in cellular homeostasis and disease", Nucleus, Mar.-Apr. 2010, p. 144-149 vol. 1 No. 2.
Siegel, R et al, "Cancer statistics", CA Cancer J Clin, Jan. 2012, p. 10-29 vol. 62 No. 1 (e-published Jan. 4, 2012).
States DJ, et al. Challenges in deriving high-confidence protein identifications from data gathered by a HUPO plasma proteome collaborative study. Nature Biotechnology. Mar. 2006;24(3):333-8.
Steen H, et al. The ABC's (and XYZ's) of peptide sequencing. Nature Reviews Molecular Cell Biology. Sep. 2004;5(9):699-711.
Suh, K.S. et al., CLIC4, an Intracellular Chloride Channel Protein, Is a Novel.
Suh, K.S. et al., Reciprocal Modifications of CLIC4 in Tumor Epithelium and Stroma Mark Malignant Progression of Multiple Human Cancers, Human Cancer Biology, Jan. 2007, 13(1): 121-131.
Tang HY, et al. A novel four-dimensional strategy combining protein and peptide separation methods enables detection of low-abundance proteins in human plasma and serum proteomes. Proteomics. Feb. 2005;5(13):3329-42.
Tang, H. Y. et al, "A xenograft mouse model coupled with in-depth plasma proteome analysis facilitates identification of novel serum biomarkers for human ovarian cancer", J Proteome Res, Feb. 2012, p. 678-691 vol. 11 No. 2.
Tang, H. Y. et al, "Rapid Verification of Candidate Serological Biomarkers Using Gel-based, Label-free Multiple Reaction Monitoring", J Proteome Res, Sep. 2011, p. 4005-4017 vol. 10 No. 9.
Tong YK and Dennis Lo YM. Diagnostic developments involving cell-free (circulating) nucleic acids. Clinica Chimica Acta, Jan. 2006;363(1-2):187-96.
Vickers, I. et al, "Isolation, activity and immunological characterization of a secreted aspartic protease, CtsD, from Aspergillus fumigatus", Protein Expression and Purification, Feb. 2007, p. 216-224 vol. 53 No. 1.
Wang H, et al. Comparison of extensive protein fractionation and repetitive LC-MS/MS analyses on depth of analysis for complex proteomes. Journal of Proteome Research. Dec. 2009;9(2):1032-40
Wang, H. et al, "Data analysis strategy for maximizing high-confidence protein identifications in complex proteomes such as human tumor secretomes and human serum", J Proteome Res, Nov. 2011, p. 4993-5005 vol. 10 No. 11.
Wang, J.W. et al., Identification of Metastasis-Associated Proteins Involved in Gallbladder Carcinoma Metastasis by Proteomic Analysis and Functional Exploration of Chloride Intracellular Channel 1, Cancer Letters, Dec. 2008, 281(1): 71-81.
Wang, W. et al., The Expression and Clinical Significance of CLIC1 and HSP27 in Lung Adenocarcinoma, Tumour Biology, Aug. 2011, 32(6): 1199-1208.
Wei, B. R. et al, "Serum S100A6 concentration predicts peritoneal tumor burden in mice with epithelial ovarian cancer and is associated with advanced stage in patients", PLoS One, Oct. 2009, p. e7670 vol. 4 No. 10.
Wu, C. et al, "Proteomic assessment of a cell model of spinal muscular atrophy", BMC Neuroscience, Mar. 2011, p. 1-13 vol. 12 No. 1.
Yao, Q. et al., CLIC4 Mediates TGF-β1-Induced Fibroblast-To-Myofibroblast Transdifferentiation in Ovarian Cancer, Oncology Reports, Sep. 2009, 22: 541-548.
Zhang, J. et al., Using Proteomic Approach to Identify Tumor-Associated Proteins as Biomarkers in Human Esophageal Squamous Cell Carcinoma, Journal of Proteome, Apr. 2011, 10(6): 2863-2872.
Zhang, Z. et al, "Three biomarkers identified from serum proteomic analysis for the detection of early stage ovarian cancer", Cancer Res, Aug. 2004, p. 5882-5890 vol. 64 No. 16.
Zhu W, et al. Mass spectrometry-based label-free quantitative proteomics. Journal of Biomedicine & Biotechnology. Nov. 2009;2010:840518.
Zhu, Y. et al, "Classifications of ovarian cancer tissues by proteomic patterns", Proteomics, Jul. 2006, vol. 6 No. 21, p. 5846-5856.
International Search Report from related International Application No. PCT/US2012/054136 dated Mar. 14, 2013.
Office Action dated Mar. 26, 2013 from related U.S. Appl. No. 13/397,442, filed Feb. 15, 2012.
Response filed Jul. 1, 2013 to Office Action in related U.S. Appl. No. 13/397,442, filed Feb. 15, 2012.

(56) References Cited

OTHER PUBLICATIONS

Final Office Action dated Oct. 28, 2013 in related U.S. Appl. No. 13/397,442, filed Feb. 15, 2012.
Advisory Action dated Jan. 14, 2014 in related U.S. Appl. No. 13/397,442.
Response to Final Office Action dated Jan. 27, 2014 in related U.S. Appl. No. 13/397,442.
Non-Final Office Action dated Dec. 23, 2014 in related U.S. Appl. No. 13/397,442.
Response to Non-Final Office Action dated Mar. 24, 2015 in related U.S. Appl. No. 13/397,442.
Response to the Final Office Action dated Dec. 30, 2013 in related U.S. Appl. No. 13/397,442, filed Feb. 15, 2012.
Response to the Non-Final Office Action dated Mar. 23, 2015 in related U.S. Appl. No. 13/397,442, filed Feb. 15, 2012.
Final Office Action dated Aug. 3, 2015 in related U.S. Appl. No. 13/397,442, filed Feb. 15, 2012.
Final Office Action dated May 29, 2015 in related U.S. Appl. No. 14/065,923, filed Oct. 29, 2013.
Appeal Brief dated Jul. 17, 2017 filed in parent U.S. Appl. No. 14/045,452.
Advisory Action dated Jan. 27, 2017 issued in parent U.S. Appl. No. 14/045,452.
Office action dated Sep. 16, 2016 and response thereto dated Jan. 17, 2017 from parent U.S. Appl. No. 14/045,452.
Office action dated Feb. 19, 2016 and response thereto dated Mary 17, 2016 from parent U.S. Appl. No. 14/045,452.

\* cited by examiner

FIG. 5A 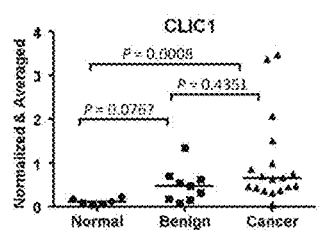 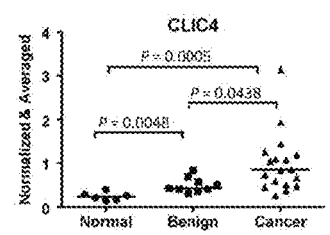 FIG. 5B
FIG. 5C 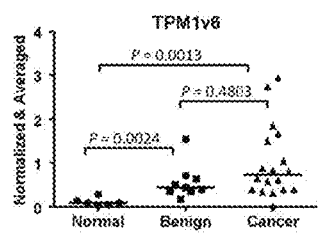 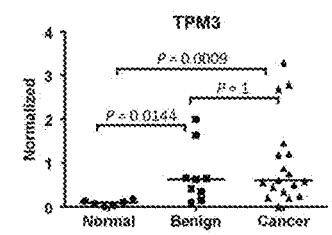 FIG. 5D
FIG. 5E 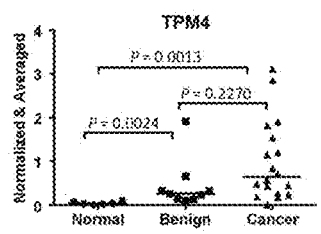 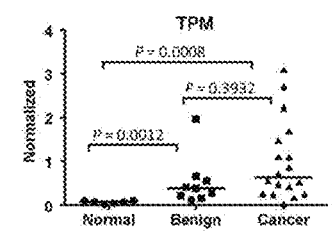 FIG. 5F

SEQUENCE LISTING

```
<160> NUMBER OF SEQ ID NOS: 80

<210> SEQ ID NO 1
<211> LENGTH: 253
<212> TYPE: PRT
<213> ORGANISM: Homo sapiens

<400> SEQUENCE: 1

Met Ala Leu Ser Met Pro Leu Asn Gly Leu Lys Glu Glu Asp Lys Glu
1               5                   10                  15

Pro Leu Ile Glu Leu Phe Val Lys Ala Gly Ser Asp Gly Glu Ser Ile
            20                  25                  30

Gly Asn Cys Pro Phe Ser Gln Arg Leu Phe Met Ile Leu Trp Leu Lys
        35                  40                  45

Gly Val Val Phe Ser Val Thr Thr Val Asp Leu Lys Arg Lys Pro Ala
    50                  55                  60

Asp Leu Gln Asn Leu Ala Pro Gly Thr His Pro Pro Phe Ile Thr Phe
65                  70                  75                  80

Asn Ser Glu Val Lys Thr Asp Val Asn Lys Ile Glu Glu Phe Leu Glu
```

```
                85                  90                  95
Glu Val Leu Cys Pro Pro Lys Tyr Leu Lys Leu Ser Pro Lys His Pro
                100                 105                 110

Glu Ser Asn Thr Ala Gly Met Asp Ile Phe Ala Lys Phe Ser Ala Tyr
            115                 120                 125

Ile Lys Asn Ser Arg Pro Glu Ala Asn Glu Ala Leu Glu Arg Gly Leu
        130                 135                 140

Leu Lys Thr Leu Gln Lys Leu Asp Glu Tyr Leu Asn Ser Pro Leu Pro
145                 150                 155                 160

Asp Glu Ile Asp Glu Asn Ser Met Glu Asp Ile Lys Phe Ser Thr Arg
                165                 170                 175

Lys Phe Leu Asp Gly Asn Glu Met Thr Leu Ala Asp Cys Asn Leu Leu
                180                 185                 190

Pro Lys Leu His Ile Val Lys Val Val Ala Lys Lys Tyr Arg Asn Phe
                195                 200                 205

Asp Ile Pro Lys Glu Met Thr Gly Ile Trp Arg Tyr Leu Thr Asn Ala
            210                 215                 220

Tyr Ser Arg Asp Glu Phe Thr Asn Thr Cys Pro Ser Asp Lys Glu Val
225                 230                 235                 240

Glu Ile Ala Tyr Ser Asp Val Ala Lys Arg Leu Thr Lys
                245                 250
```

<210> SEQ ID NO 2
<211> LENGTH: 253
<212> TYPE: PRT
<213> ORGANISM: Mus musculus

<400> SEQUENCE: 2

```
Met Ala Leu Ser Met Pro Leu Asn Gly Leu Lys Glu Glu Asp Lys Glu
1               5                   10                  15

Pro Leu Ile Glu Leu Phe Val Lys Ala Gly Ser Asp Gly Glu Ser Ile
                20                  25                  30

Gly Asn Cys Pro Phe Ser Gln Arg Leu Phe Met Ile Leu Trp Leu Lys
            35                  40                  45

Gly Val Val Phe Ser Val Thr Thr Val Asp Leu Lys Arg Lys Pro Ala
        50                  55                  60

Asp Leu Gln Asn Leu Ala Pro Gly Thr His Pro Pro Phe Ile Thr Phe
65                  70                  75                  80

Asn Ser Glu Val Lys Thr Asp Val Asn Lys Ile Glu Glu Phe Leu Glu
                85                  90                  95

Glu Val Leu Cys Pro Pro Lys Tyr Leu Lys Leu Ser Pro Lys His Pro
                100                 105                 110

Glu Ser Asn Thr Ala Gly Met Asp Ile Phe Ala Lys Phe Ser Ala Tyr
            115                 120                 125

Ile Lys Asn Ser Arg Pro Glu Ala Asn Glu Ala Leu Glu Arg Gly Leu
        130                 135                 140

Leu Lys Thr Leu Gln Lys Leu Asp Glu Tyr Leu Asn Ser Pro Leu Pro
145                 150                 155                 160

Asp Glu Ile Asp Glu Asn Ser Met Glu Asp Ile Lys Phe Ser Thr Arg
                165                 170                 175

Arg Phe Leu Asp Gly Asp Glu Met Thr Leu Ala Asp Cys Asn Leu Leu
                180                 185                 190

Pro Lys Leu His Ile Val Lys Val Val Ala Lys Lys Tyr Arg Asn Phe
                195                 200                 205
```

```
Asp Ile Pro Lys Gly Met Thr Gly Ile Trp Arg Tyr Leu Thr Asn Ala
    210                 215                 220
Tyr Ser Arg Asp Glu Phe Thr Asn Thr Cys Pro Ser Asp Lys Glu Val
225                 230                 235                 240
Glu Ile Ala Tyr Ser Asp Val Ala Lys Arg Leu Thr Lys
                245                 250

<210> SEQ ID NO 3
<211> LENGTH: 241
<212> TYPE: PRT
<213> ORGANISM: Homo sapiens

<400> SEQUENCE: 3

Met Ala Glu Glu Gln Pro Gln Val Glu Leu Phe Val Lys Ala Gly Ser
1               5                   10                  15
Asp Gly Ala Lys Ile Gly Asn Cys Pro Phe Ser Gln Arg Leu Phe Met
            20                  25                  30
Val Leu Trp Leu Lys Gly Val Thr Phe Asn Val Thr Thr Val Asp Thr
        35                  40                  45
Lys Arg Arg Thr Glu Thr Val Gln Lys Leu Cys Pro Gly Gly Gln Leu
    50                  55                  60
Pro Phe Leu Leu Tyr Gly Thr Glu Val His Thr Asp Thr Asn Lys Ile
65                  70                  75                  80
Glu Glu Phe Leu Glu Ala Val Leu Cys Pro Pro Arg Tyr Pro Lys Leu
                85                  90                  95
Ala Ala Leu Asn Pro Glu Ser Asn Thr Ala Gly Leu Asp Ile Phe Ala
            100                 105                 110
Lys Phe Ser Ala Tyr Ile Lys Asn Ser Asn Pro Ala Leu Asn Asp Asn
        115                 120                 125
Leu Glu Lys Gly Leu Leu Lys Ala Leu Lys Val Leu Asp Asn Tyr Leu
    130                 135                 140
Thr Ser Pro Leu Pro Glu Glu Val Asp Glu Thr Ser Ala Glu Asp Glu
145                 150                 155                 160
Gly Val Ser Gln Arg Lys Phe Leu Asp Gly Asn Glu Leu Thr Leu Ala
                165                 170                 175
Asp Cys Asn Leu Leu Pro Lys Leu His Ile Val Gln Val Val Cys Lys
            180                 185                 190
Lys Tyr Arg Gly Phe Thr Ile Pro Glu Ala Phe Arg Gly Val His Arg
        195                 200                 205
Tyr Leu Ser Asn Ala Tyr Ala Arg Glu Glu Phe Ala Ser Thr Cys Pro
    210                 215                 220
Asp Asp Glu Glu Ile Glu Leu Ala Tyr Glu Gln Val Ala Lys Ala Leu
225                 230                 235                 240
Lys

<210> SEQ ID NO 4
<211> LENGTH: 247
<212> TYPE: PRT
<213> ORGANISM: Homo sapiens

<400> SEQUENCE: 4

Met Ser Gly Leu Arg Pro Gly Thr Gln Val Asp Pro Glu Ile Glu Leu
1               5                   10                  15
Phe Val Lys Ala Gly Ser Asp Gly Glu Ser Ile Gly Asn Cys Pro Phe
            20                  25                  30
Cys Gln Arg Leu Phe Met Ile Leu Trp Leu Lys Gly Val Lys Phe Asn
```

```
            35                  40                  45
Val Thr Thr Val Asp Met Thr Arg Lys Pro Glu Glu Leu Lys Asp Leu
 50                  55                  60

Ala Pro Gly Thr Asn Pro Pro Phe Leu Val Tyr Asn Lys Glu Leu Lys
 65                  70                  75                  80

Thr Asp Phe Ile Lys Ile Glu Glu Phe Leu Glu Gln Thr Leu Ala Pro
                 85                  90                  95

Pro Arg Tyr Pro His Leu Ser Pro Lys Tyr Lys Glu Ser Phe Asp Val
            100                 105                 110

Gly Cys Asn Leu Phe Ala Lys Phe Ser Ala Tyr Ile Lys Asn Thr Gln
        115                 120                 125

Lys Glu Ala Asn Lys Asn Phe Glu Lys Ser Leu Leu Lys Glu Phe Lys
    130                 135                 140

Arg Leu Asp Asp Tyr Leu Asn Thr Pro Leu Leu Asp Glu Ile Asp Pro
145                 150                 155                 160

Asp Ser Ala Glu Glu Pro Pro Val Ser Asx Asx Leu Phe Leu Asp Gly
                165                 170                 175

Asp Gln Leu Thr Leu Ala Asp Cys Ser Leu Leu Pro Lys Leu Asn Ile
            180                 185                 190

Ile Lys Val Ala Ala Lys Lys Tyr Arg Asp Phe Asp Ile Pro Ala Glu
        195                 200                 205

Phe Ser Gly Val Trp Arg Tyr Leu His Asn Ala Tyr Ala Arg Glu Glu
    210                 215                 220

Phe Thr His Thr Cys Pro Glu Asp Lys Glu Ile Glu Asn Thr Tyr Ala
225                 230                 235                 240

Asn Val Ala Lys Gln Lys Ser
                245

<210> SEQ ID NO 5
<211> LENGTH: 236
<212> TYPE: PRT
<213> ORGANISM: Homo sapiens

<400> SEQUENCE: 5

Met Ala Glu Thr Lys Leu Gln Leu Phe Val Lys Ala Ser Glu Asp Gly
  1               5                  10                  15

Glu Ser Val Gly His Cys Pro Ser Cys Gln Arg Leu Phe Met Val Leu
             20                  25                  30

Leu Leu Lys Gly Val Pro Phe Thr Leu Thr Thr Val Asp Thr Arg Asx
         35                  40                  45

Ser Pro Asp Val Leu Lys Asp Phe Ala Pro Gly Ser Gln Leu Pro Ile
 50                  55                  60

Leu Leu Tyr Asp Ser Asp Ala Lys Thr Asp Thr Leu Gln Ile Glu Asp
 65                  70                  75                  80

Phe Leu Glu Glu Thr Leu Gly Pro Pro Asp Phe Pro Ser Leu Ala Pro
                 85                  90                  95

Arg Tyr Asx Glu Ser Asn Thr Ala Gly Asn Asp Val Phe His Lys Phe
            100                 105                 110

Ser Ala Phe Ile Lys Asn Pro Val Pro Ala Gln Asp Glu Ala Leu Tyr
        115                 120                 125

Gln Gln Leu Leu Arg Ala Leu Ala Arg Leu Asp Ser Tyr Leu Arg Ala
    130                 135                 140

Pro Leu Glu His Glu Leu Ala Gly Glu Pro Gln Leu Arg Glu Ser Arg
145                 150                 155                 160
```

```
Arg Arg Phe Leu Asp Gly Asp Arg Leu Thr Leu Ala Asp Cys Ser Leu
                165                 170                 175

Leu Pro Lys Leu His Ile Val Asp Thr Val Cys Ala His Phe Arg Gln
            180                 185                 190

Ala Pro Ile Pro Ala Glu Leu Arg Gly Val Arg Arg Tyr Leu Asp Ser
        195                 200                 205

Ala Met Gln Glu Lys Glu Phe Lys Tyr Thr Cys Pro His Ser Ala Glu
    210                 215                 220

Ile Leu Ala Ala Tyr Arg Pro Ala Val His Pro Arg
225                 230                 235
```

<210> SEQ ID NO 6
<211> LENGTH: 245
<212> TYPE: PRT
<213> ORGANISM: Homo sapiens

<400> SEQUENCE: 6

```
Met Ala Gly Ser Ser Leu Glu Ala Val Arg Arg Lys Ile Arg Ser
1               5                   10                  15

Leu Gln Glu Gln Ala Asp Ala Ala Glu Glu Arg Ala Gly Thr Leu Gln
            20                  25                  30

Arg Glu Leu Asp His Glu Arg Lys Leu Arg Glu Thr Ala Glu Ala Asp
        35                  40                  45

Val Ala Ser Leu Asn Arg Arg Ile Gln Leu Val Glu Glu Glu Leu Asp
    50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Ser
                85                  90                  95

Arg Ala Gln Lys Asp Glu Glu Lys Met Glu Ile Gln Glu Ile Gln Leu
            100                 105                 110

Lys Glu Ala Lys His Ile Ala Glu Asp Ala Asp Arg Lys Tyr Glu Glu
        115                 120                 125

Val Ala Arg Lys Leu Val Ile Ile Glu Ser Asp Leu Glu Arg Ala Glu
    130                 135                 140

Glu Arg Ala Glu Leu Ser Glu Gly Lys Cys Ala Glu Leu Glu Glu Glu
145                 150                 155                 160

Leu Lys Thr Val Thr Asn Asn Leu Lys Ser Leu Glu Ala Gln Ala Glu
                165                 170                 175

Lys Tyr Ser Gln Lys Glu Asp Arg Tyr Glu Glu Glu Ile Lys Val Leu
            180                 185                 190

Ser Asp Lys Leu Lys Glu Ala Glu Thr Arg Ala Glu Phe Ala Glu Arg
        195                 200                 205

Ser Val Thr Lys Leu Glu Lys Ser Ile Asp Asp Leu Glu Asp Gln Leu
    210                 215                 220

Tyr Gln Gln Leu Glu Gln Asn Arg Arg Leu Thr Asn Glu Leu Lys Leu
225                 230                 235                 240

Ala Leu Asn Glu Asp
                245
```

<210> SEQ ID NO 7
<211> LENGTH: 245
<212> TYPE: PRT
<213> ORGANISM: Homo sapiens

<400> SEQUENCE: 7

```
Met Ala Gly Ser Ser Ser Leu Glu Ala Val Arg Arg Lys Ile Arg Ser
1               5                   10                  15

Leu Gln Glu Gln Ala Asp Ala Ala Glu Glu Arg Ala Gly Thr Leu Gln
            20                  25                  30

Arg Glu Leu Asp His Glu Arg Lys Leu Arg Glu Thr Ala Glu Ala Asp
        35                  40                  45

Val Ala Ser Leu Asn Arg Arg Ile Gln Leu Val Glu Glu Glu Leu Asp
50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Ser
                85                  90                  95

Arg Ala Gln Lys Asp Glu Glu Lys Met Glu Ile Gln Glu Ile Gln Leu
            100                 105                 110

Lys Glu Ala Lys His Ile Ala Glu Asp Ala Asp Arg Lys Tyr Glu Glu
            115                 120                 125

Val Ala Arg Lys Leu Val Ile Ile Glu Ser Asp Leu Glu Arg Ala Glu
        130                 135                 140

Glu Arg Ala Glu Leu Ser Glu Gly Lys Cys Ala Glu Leu Glu Glu Glu
145                 150                 155                 160

Leu Lys Thr Val Thr Asn Asn Leu Lys Ser Leu Glu Ala Gln Ala Glu
                165                 170                 175

Lys Tyr Ser Gln Lys Glu Asp Arg Tyr Glu Glu Glu Ile Lys Val Leu
            180                 185                 190

Ser Asp Lys Leu Lys Glu Ala Glu Thr Arg Ala Glu Phe Ala Glu Arg
        195                 200                 205

Ser Val Thr Lys Leu Glu Lys Ser Ile Asp Asp Leu Glu Asp Gln Leu
210                 215                 220

Tyr Gln Gln Leu Glu Gln Asn Arg Arg Leu Thr Asn Glu Leu Lys Leu
225                 230                 235                 240

Ala Leu Asn Glu Asp
            245

<210> SEQ ID NO 8
<211> LENGTH: 303
<212> TYPE: PRT
<213> ORGANISM: Homo sapiens

<400> SEQUENCE: 8

Gly Gly Arg Asp Phe Arg Thr Ala Pro Gly Arg Arg Gly Arg Arg Arg
1               5                   10                  15

Arg Thr Glu Arg Pro Gly Arg Gly Pro Ala Leu Gly Ser Gln Asp
            20                  25                  30

Ser Arg Gly Ser Arg Val Arg Ala Ala Ala Gly Leu Ser His Cys
        35                  40                  45

Ser Pro Pro Ala Arg Leu Pro Ser Gly Ala Met Ala Gly Ser Ser Ser
50                  55                  60

Leu Glu Ala Val Arg Arg Lys Ile Arg Ser Leu Gln Glu Gln Ala Asp
65                  70                  75                  80

Ala Ala Glu Glu Arg Ala Gly Thr Leu Gln Arg Glu Leu Asp His Glu
                85                  90                  95

Arg Lys Leu Arg Glu Thr Ala Glu Ala Asp Val Ala Ser Leu Asn Arg
            100                 105                 110

Arg Ile Gln Leu Val Glu Glu Glu Leu Asp Arg Ala Gln Glu Arg Leu
        115                 120                 125
```

```
Ala Thr Ala Leu Gln Lys Leu Glu Glu Ala Glu Lys Ala Ala Asp Gly
        130                 135                 140

Ser Glu Arg Gly Met Lys Val Ile Glu Ser Arg Ala Gln Lys Asp Glu
145                 150                 155                 160

Glu Lys Met Glu Ile Gln Glu Ile Gln Leu Lys Glu Ala Lys His Ile
                165                 170                 175

Ala Glu Asp Ala Asp Arg Lys Tyr Glu Glu Val Ala Arg Lys Leu Val
            180                 185                 190

Ile Ile Glu Ser Asp Leu Glu Arg Ala Glu Glu Arg Ala Glu Leu Ser
        195                 200                 205

Glu Gly Lys Cys Ala Glu Leu Glu Glu Glu Leu Lys Thr Val Thr Asn
210                 215                 220

Asn Leu Lys Ser Leu Glu Ala Gln Ala Glu Lys Tyr Ser Gln Lys Glu
225                 230                 235                 240

Asp Arg Tyr Glu Glu Glu Ile Lys Val Leu Ser Asp Lys Leu Lys Glu
                245                 250                 255

Ala Glu Thr Arg Ala Glu Phe Ala Glu Arg Ser Val Thr Lys Leu Glu
            260                 265                 270

Lys Ser Ile Asp Asp Leu Glu Asp Gln Leu Tyr Gln Gln Leu Glu Gln
        275                 280                 285

Asn Arg Arg Leu Thr Asn Glu Leu Lys Leu Ala Leu Asn Glu Asp
290                 295                 300

<210> SEQ ID NO 9
<211> LENGTH: 248
<212> TYPE: PRT
<213> ORGANISM: Homo sapiens

<400> SEQUENCE: 9

Met Ala Gly Ser Ser Leu Glu Ala Val Arg Arg Lys Ile Arg Ser
1               5                   10                  15

Leu Gln Glu Gln Ala Asp Ala Ala Glu Glu Arg Ala Gly Thr Leu Gln
            20                  25                  30

Arg Glu Leu Asp His Glu Arg Lys Leu Arg Glu Thr Ala Glu Ala Asp
        35                  40                  45

Val Ala Ser Leu Asn Arg Arg Ile Gln Leu Val Glu Glu Glu Leu Asp
    50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Ser
                85                  90                  95

Arg Ala Gln Lys Asp Glu Glu Lys Met Glu Ile Gln Glu Ile Gln Leu
            100                 105                 110

Lys Glu Ala Lys His Ile Ala Glu Asp Ala Asp Arg Lys Tyr Glu Glu
        115                 120                 125

Val Ala Arg Lys Leu Val Ile Ile Glu Ser Asp Leu Glu Arg Ala Glu
    130                 135                 140

Glu Arg Ala Glu Leu Ser Glu Gly Lys Cys Ala Glu Leu Glu Glu Glu
145                 150                 155                 160

Leu Lys Thr Val Thr Asn Asn Leu Lys Ser Leu Glu Ala Gln Ala Glu
                165                 170                 175

Lys Tyr Ser Gln Lys Glu Asp Arg Tyr Glu Glu Glu Ile Lys Val Leu
            180                 185                 190

Ser Asp Lys Leu Lys Glu Ala Glu Thr Arg Ala Glu Phe Ala Glu Arg
```

```
            195                 200                 205
Ser Val Thr Lys Leu Glu Lys Ser Ile Asp Asp Leu Glu Glu Lys Val
    210                 215                 220

Ala His Ala Lys Glu Glu Asn Leu Ser Met His Gln Met Leu Asp Gln
225                 230                 235                 240

Thr Leu Leu Glu Leu Asn Asn Met
                245

<210> SEQ ID NO 10
<211> LENGTH: 245
<212> TYPE: PRT
<213> ORGANISM: Homo sapiens

<400> SEQUENCE: 10

Met Ala Gly Ser Ser Leu Glu Ala Val Arg Arg Lys Ile Arg Ser
1               5                   10                  15

Leu Gln Glu Gln Ala Asp Ala Ala Glu Glu Arg Ala Gly Thr Leu Gln
                20                  25                  30

Arg Glu Leu Asp His Glu Arg Lys Leu Arg Glu Thr Ala Glu Ala Asp
            35                  40                  45

Val Ala Ser Leu Asn Arg Arg Ile Gln Leu Val Glu Glu Glu Leu Asp
        50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Ser
                85                  90                  95

Arg Ala Gln Lys Asp Glu Glu Lys Met Glu Ile Gln Glu Ile Gln Leu
            100                 105                 110

Lys Glu Ala Lys His Ile Ala Glu Asp Ala Asp Arg Lys Tyr Glu Glu
        115                 120                 125

Val Ala Arg Lys Leu Val Ile Ile Glu Ser Asp Leu Glu Arg Ala Glu
    130                 135                 140

Glu Arg Ala Glu Leu Ser Glu Gly Gln Val Arg Gln Leu Glu Glu Gln
145                 150                 155                 160

Leu Arg Ile Met Asp Gln Thr Leu Lys Ala Leu Met Ala Ala Glu Asp
                165                 170                 175

Lys Tyr Ser Gln Lys Glu Asp Arg Tyr Glu Glu Glu Ile Lys Val Leu
            180                 185                 190

Ser Asp Lys Pro Lys Glu Ala Glu Thr Arg Ala Glu Phe Ala Glu Arg
        195                 200                 205

Ser Val Thr Lys Leu Glu Lys Ser Ile Asp Asp Leu Glu Asp Gln Leu
    210                 215                 220

Tyr Gln Gln Leu Glu Gln Asn Arg Arg Leu Thr Asn Glu Leu Lys Leu
225                 230                 235                 240

Ala Leu Asn Glu Asp
                245

<210> SEQ ID NO 11
<211> LENGTH: 275
<212> TYPE: PRT
<213> ORGANISM: Homo sapiens

<400> SEQUENCE: 11

Met Ala Gly Ser Ser Leu Glu Ala Val Arg Arg Lys Ile Arg Ser
1               5                   10                  15

Leu Gln Glu Gln Ala Asp Ala Ala Glu Glu Arg Ala Gly Thr Leu Gln
```

```
                       20                  25                  30
Arg Glu Leu Asp His Glu Arg Lys Leu Arg Glu Thr Ala Glu Ala Asp
                35                  40                  45
Val Ala Ser Leu Asn Arg Arg Ile Gln Leu Val Glu Glu Glu Leu Asp
            50                  55                  60
Arg Ala Gln Glu Arg Leu Ala Thr Ala Leu Gln Lys Leu Glu Glu Ala
65                  70                  75                  80
Glu Lys Ala Ala Asp Glu Ser Glu Arg Gly Met Lys Val Ile Glu Ser
                85                  90                  95
Arg Ala Gln Lys Asp Glu Glu Lys Met Glu Ile Gln Glu Ile Gln Leu
                100                 105                 110
Lys Glu Ala Lys His Ile Ala Glu Asp Ala Asp Arg Lys Tyr Glu Glu
                115                 120                 125
Val Ala Arg Lys Leu Val Ile Ile Glu Ser Asp Leu Glu Arg Ala Glu
            130                 135                 140
Glu Arg Ala Glu Leu Ser Glu Gly Gln Val Arg Gln Leu Glu Glu Gln
145                 150                 155                 160
Leu Arg Ile Met Asp Gln Thr Leu Lys Ala Leu Met Ala Ala Glu Asp
                165                 170                 175
Lys Tyr Ser Gln Lys Glu Asp Arg Tyr Glu Glu Glu Ile Lys Val Leu
                180                 185                 190
Ser Asp Lys Leu Lys Glu Ala Glu Thr Arg Ala Glu Phe Ala Glu Arg
                195                 200                 205
Ser Val Thr Lys Leu Glu Lys Ser Ile Asp Asp Leu Glu Gly Lys Ile
            210                 215                 220
Leu Ser Ser Val Phe Ser Leu Ile Leu Met Val Glu Tyr Gln Pro Gly
225                 230                 235                 240
Lys Thr Ile Phe Gln Phe Lys Gly Ile His Ile Asp Thr Leu Leu Cys
                245                 250                 255
Thr Cys Thr Phe Phe Leu Cys Val Leu Trp Gly Phe Ser Leu Trp Leu
                260                 265                 270
Leu Asn Ser
        275

<210> SEQ ID NO 12
<211> LENGTH: 14
<212> TYPE: PRT
<213> ORGANISM: Homo sapiens

<400> SEQUENCE: 12

Ile Gln Val Leu Gln Gln Gln Ala Asp Asp Ala Glu Glu Arg
1               5                   10

<210> SEQ ID NO 13
<211> LENGTH: 10
<212> TYPE: PRT
<213> ORGANISM: Homo sapiens

<400> SEQUENCE: 13

Ala Glu Gly Asp Val Ala Ala Leu Asn Arg
1               5                   10

<210> SEQ ID NO 14
<211> LENGTH: 14
<212> TYPE: PRT
<213> ORGANISM: Homo sapiens

<400> SEQUENCE: 14
```

Ile Gln Ala Leu Gln Gln Ala Asp Glu Ala Glu Asp Arg
1               5                   10

<210> SEQ ID NO 15
<211> LENGTH: 11
<212> TYPE: PRT
<213> ORGANISM: Homo sapiens

<400> SEQUENCE: 15

Lys Leu Val Ile Leu Glu Gly Glu Leu Glu Arg
1               5                   10

<210> SEQ ID NO 16
<211> LENGTH: 11
<212> TYPE: PRT
<213> ORGANISM: Homo sapiens

<400> SEQUENCE: 16

Arg Ile Gln Leu Val Glu Glu Glu Leu Asp Arg
1               5                   10

<210> SEQ ID NO 17
<211> LENGTH: 13
<212> TYPE: PRT
<213> ORGANISM: Homo sapiens

<400> SEQUENCE: 17

Ala Thr Asp Ala Glu Ala Asp Val Ala Ser Leu Asn Arg
1               5                   10

<210> SEQ ID NO 18
<211> LENGTH: 11
<212> TYPE: PRT
<213> ORGANISM: Homo sapiens

<400> SEQUENCE: 18

Lys Leu Val Ile Leu Glu Gly Glu Leu Glu Arg
1               5                   10

<210> SEQ ID NO 19
<211> LENGTH: 13
<212> TYPE: PRT
<213> ORGANISM: Homo sapiens

<400> SEQUENCE: 19

Arg Lys Leu Val Ile Leu Glu Gly Glu Leu Glu Arg Ser
1               5                   10

<210> SEQ ID NO 20
<211> LENGTH: 9
<212> TYPE: PRT
<213> ORGANISM: Homo sapiens

<400> SEQUENCE: 20

Met Glu Leu Gln Glu Met Gln Leu Lys
1               5

<210> SEQ ID NO 21
<211> LENGTH: 12
<212> TYPE: PRT
<213> ORGANISM: Homo sapiens

<400> SEQUENCE: 21

Ser Leu Met Ala Ser Glu Glu Glu Tyr Ser Thr Lys

```
1               5                    10

<210> SEQ ID NO 22
<211> LENGTH: 9
<212> TYPE: PRT
<213> ORGANISM: Homo sapiens

<400> SEQUENCE: 22

Glu Asp Lys Tyr Glu Glu Glu Ile Lys
1               5

<210> SEQ ID NO 23
<211> LENGTH: 9
<212> TYPE: PRT
<213> ORGANISM: Homo sapiens

<400> SEQUENCE: 23

Cys Gly Asp Leu Glu Glu Glu Leu Lys
1               5

<210> SEQ ID NO 24
<211> LENGTH: 15
<212> TYPE: PRT
<213> ORGANISM: Homo sapiens

<400> SEQUENCE: 24

Lys Ile Gln Val Leu Gln Gln Gln Ala Asp Asp Ala Glu Glu Arg
1               5                   10                  15

<210> SEQ ID NO 25
<211> LENGTH: 9
<212> TYPE: PRT
<213> ORGANISM: Homo sapiens

<400> SEQUENCE: 25

Met Glu Leu Gln Glu Ile Gln Leu Lys
1               5

<210> SEQ ID NO 26
<211> LENGTH: 11
<212> TYPE: PRT
<213> ORGANISM: Homo sapiens

<400> SEQUENCE: 26

Lys Leu Val Ile Ile Glu Gly Asp Leu Glu Arg
1               5                   10

<210> SEQ ID NO 27
<211> LENGTH: 8
<212> TYPE: PRT
<213> ORGANISM: Homo sapiens

<400> SEQUENCE: 27

His Ile Ala Glu Glu Ala Asp Arg
1               5

<210> SEQ ID NO 28
<211> LENGTH: 12
<212> TYPE: PRT
<213> ORGANISM: Homo sapiens

<400> SEQUENCE: 28

Met Leu Asp Gln Thr Leu Leu Asp Leu Asn Glu Met
1               5                   10
```

```
<210> SEQ ID NO 29
<211> LENGTH: 8
<212> TYPE: PRT
<213> ORGANISM: Homo sapiens

<400> SEQUENCE: 29

Cys Leu Ser Ala Ala Glu Glu Lys
1               5

<210> SEQ ID NO 30
<211> LENGTH: 13
<212> TYPE: PRT
<213> ORGANISM: Homo sapiens

<400> SEQUENCE: 30

Ala Ala Asp Ala Glu Ala Glu Val Ala Ser Leu Asn Arg
1               5                   10

<210> SEQ ID NO 31
<211> LENGTH: 15
<212> TYPE: PRT
<213> ORGANISM: Homo sapiens

<400> SEQUENCE: 31

Lys Ile Gln Ala Leu Gln Gln Gln Ala Asp Glu Ala Glu Asp Arg
1               5                   10                  15

<210> SEQ ID NO 32
<211> LENGTH: 20
<212> TYPE: PRT
<213> ORGANISM: Homo sapiens

<400> SEQUENCE: 32

Glu Glu Asn Val Gly Leu His Gln Thr Leu Asp Gln Thr Leu Asn Glu
1               5                   10                  15

Leu Asn Cys Ile
            20

<210> SEQ ID NO 33
<211> LENGTH: 9
<212> TYPE: PRT
<213> ORGANISM: Homo sapiens

<400> SEQUENCE: 33

Met Glu Ile Gln Glu Met Gln Leu Lys
1               5

<210> SEQ ID NO 34
<211> LENGTH: 13
<212> TYPE: PRT
<213> ORGANISM: Homo sapiens

<400> SEQUENCE: 34

Tyr Ser Glu Lys Glu Asp Lys Tyr Glu Glu Glu Ile Lys
1               5                   10

<210> SEQ ID NO 35
<211> LENGTH: 12
<212> TYPE: PRT
<213> ORGANISM: Homo sapiens

<400> SEQUENCE: 35

Glu Lys Ala Glu Gly Asp Val Ala Ala Leu Asn Arg
1               5                   10
```

<210> SEQ ID NO 36
<211> LENGTH: 8
<212> TYPE: PRT
<213> ORGANISM: Homo sapiens

<400> SEQUENCE: 36

Thr Ile Asp Asp Leu Glu Glu Lys
1               5

<210> SEQ ID NO 37
<211> LENGTH: 13
<212> TYPE: PRT
<213> ORGANISM: Homo sapiens

<400> SEQUENCE: 37

Ala Ser Asp Ala Glu Gly Asp Val Ala Ala Leu Asn Arg
1               5                   10

<210> SEQ ID NO 38
<211> LENGTH: 19
<212> TYPE: PRT
<213> ORGANISM: Homo sapiens

<400> SEQUENCE: 38

Lys Phe Leu Asp Gly Asn Glu Leu Thr Leu Ala Asp Cys Asn Leu Leu
1               5                   10                  15

Pro Lys Leu

<210> SEQ ID NO 39
<211> LENGTH: 14
<212> TYPE: PRT
<213> ORGANISM: Homo sapiens

<400> SEQUENCE: 39

Lys Gly Val Thr Phe Asn Val Thr Thr Val Asp Thr Lys Arg
1               5                   10

<210> SEQ ID NO 40
<211> LENGTH: 20
<212> TYPE: PRT
<213> ORGANISM: Homo sapiens

<400> SEQUENCE: 40

Lys Leu Ala Ala Leu Asn Pro Glu Ser Asn Thr Ala Gly Leu Asp Ile
1               5                   10                  15

Phe Ala Lys Phe
            20

<210> SEQ ID NO 41
<211> LENGTH: 29
<212> TYPE: PRT
<213> ORGANISM: Homo sapiens

<400> SEQUENCE: 41

Lys Val Leu Asp Asn Tyr Leu Thr Ser Pro Leu Pro Glu Glu Val Asp
1               5                   10                  15

Glu Thr Ser Ala Glu Asp Glu Gly Val Ser Gln Arg Lys
            20                  25

<210> SEQ ID NO 42
<211> LENGTH: 14
<212> TYPE: PRT

-continued

```
<213> ORGANISM: Homo sapiens

<400> SEQUENCE: 42

Lys Asn Ser Asn Pro Ala Leu Asn Asp Asn Leu Glu Lys Gly
1               5                   10

<210> SEQ ID NO 43
<211> LENGTH: 11
<212> TYPE: PRT
<213> ORGANISM: Homo sapiens

<400> SEQUENCE: 43

Lys Leu His Ile Val Gln Val Val Cys Lys Lys
1               5                   10

<210> SEQ ID NO 44
<211> LENGTH: 10
<212> TYPE: PRT
<213> ORGANISM: Homo sapiens

<400> SEQUENCE: 44

Arg Leu Phe Met Val Leu Trp Leu Lys Gly
1               5                   10

<210> SEQ ID NO 45
<211> LENGTH: 24
<212> TYPE: PRT
<213> ORGANISM: Homo sapiens

<400> SEQUENCE: 45

Arg Glu Glu Phe Ala Ser Thr Cys Pro Asp Asp Glu Glu Ile Glu Leu
1               5                   10                  15

Ala Tyr Glu Gln Val Ala Lys Ala
            20

<210> SEQ ID NO 46
<211> LENGTH: 20
<212> TYPE: PRT
<213> ORGANISM: Homo sapiens

<400> SEQUENCE: 46

Arg Lys Phe Leu Asp Gly Asn Glu Leu Thr Leu Ala Asp Cys Asn Leu
1               5                   10                  15

Leu Pro Lys Leu
            20

<210> SEQ ID NO 47
<211> LENGTH: 15
<212> TYPE: PRT
<213> ORGANISM: Homo sapiens

<400> SEQUENCE: 47

Lys Ile Glu Glu Phe Leu Glu Ala Val Leu Cys Pro Pro Arg Tyr
1               5                   10                  15

<210> SEQ ID NO 48
<211> LENGTH: 11
<212> TYPE: PRT
<213> ORGANISM: Homo sapiens

<400> SEQUENCE: 48

Lys Ile Gly Asn Cys Pro Phe Ser Gln Arg Leu
1               5                   10
```

<210> SEQ ID NO 49
<211> LENGTH: 11
<212> TYPE: PRT
<213> ORGANISM: Homo sapiens

<400> SEQUENCE: 49

Lys Ile Gly Asn Cys Pro Phe Ser Gln Arg Leu
1               5                   10

<210> SEQ ID NO 50
<211> LENGTH: 12
<212> TYPE: PRT
<213> ORGANISM: Homo sapiens

<400> SEQUENCE: 50

Arg Ile Gln Leu Val Glu Glu Glu Leu Asp Arg Ala
1               5                   10

<210> SEQ ID NO 51
<211> LENGTH: 13
<212> TYPE: PRT
<213> ORGANISM: Homo sapiens

<400> SEQUENCE: 51

Arg Arg Ile Gln Leu Val Glu Glu Glu Leu Asp Arg Ala
1               5                   10

<210> SEQ ID NO 52
<211> LENGTH: 12
<212> TYPE: PRT
<213> ORGANISM: Homo sapiens

<400> SEQUENCE: 52

Lys Leu Val Ile Leu Glu Gly Glu Leu Glu Arg Ser
1               5                   10

<210> SEQ ID NO 53
<211> LENGTH: 15
<212> TYPE: PRT
<213> ORGANISM: Homo sapiens

<400> SEQUENCE: 53

Lys Ala Thr Asp Ala Glu Ala Asp Val Ala Ser Leu Asn Arg Arg
1               5                   10                  15

<210> SEQ ID NO 54
<211> LENGTH: 11
<212> TYPE: PRT
<213> ORGANISM: Homo sapiens

<400> SEQUENCE: 54

Lys Met Glu Leu Gln Glu Met Gln Leu Lys Glu
1               5                   10

<210> SEQ ID NO 55
<211> LENGTH: 11
<212> TYPE: PRT
<213> ORGANISM: Homo sapiens

<400> SEQUENCE: 55

Lys Cys Gly Asp Leu Glu Glu Glu Leu Lys Ile
1               5                   10

<210> SEQ ID NO 56

```
<211> LENGTH: 8
<212> TYPE: PRT
<213> ORGANISM: Homo sapiens

<400> SEQUENCE: 56

Lys Tyr Glu Glu Glu Ile Lys Leu
1               5

<210> SEQ ID NO 57
<211> LENGTH: 14
<212> TYPE: PRT
<213> ORGANISM: Homo sapiens

<400> SEQUENCE: 57

Lys Ser Leu Met Ala Ser Glu Glu Glu Tyr Ser Thr Lys Glu
1               5                   10

<210> SEQ ID NO 58
<211> LENGTH: 11
<212> TYPE: PRT
<213> ORGANISM: Homo sapiens

<400> SEQUENCE: 58

Lys Glu Asp Lys Tyr Glu Glu Glu Ile Lys Leu
1               5                   10

<210> SEQ ID NO 59
<211> LENGTH: 11
<212> TYPE: PRT
<213> ORGANISM: Homo sapiens

<400> SEQUENCE: 59

Lys Met Glu Leu Gln Glu Ile Gln Leu Lys Glu
1               5                   10

<210> SEQ ID NO 60
<211> LENGTH: 13
<212> TYPE: PRT
<213> ORGANISM: Homo sapiens

<400> SEQUENCE: 60

Arg Lys Leu Val Ile Ile Glu Gly Asp Leu Glu Arg Thr
1               5                   10

<210> SEQ ID NO 61
<211> LENGTH: 12
<212> TYPE: PRT
<213> ORGANISM: Homo sapiens

<400> SEQUENCE: 61

Lys Leu Val Ile Ile Glu Gly Asp Leu Glu Arg Thr
1               5                   10

<210> SEQ ID NO 62
<211> LENGTH: 10
<212> TYPE: PRT
<213> ORGANISM: Homo sapiens

<400> SEQUENCE: 62

Lys His Ile Ala Glu Glu Ala Asp Arg Lys
1               5                   10

<210> SEQ ID NO 63
<211> LENGTH: 15
<212> TYPE: PRT
```

<213> ORGANISM: Homo sapiens

<400> SEQUENCE: 63

Lys Ala Asp Ala Glu Ala Glu Val Ala Ser Leu Asn Arg Arg
1               5                   10                  15

<210> SEQ ID NO 64
<211> LENGTH: 8
<212> TYPE: PRT
<213> ORGANISM: Homo sapiens

<400> SEQUENCE: 64

Lys Tyr Glu Glu Glu Ile Lys Ile
1               5

<210> SEQ ID NO 65
<211> LENGTH: 11
<212> TYPE: PRT
<213> ORGANISM: Homo sapiens

<400> SEQUENCE: 65

Lys Glu Asp Lys Tyr Glu Glu Glu Ile Lys Ile
1               5                   10

<210> SEQ ID NO 66
<211> LENGTH: 16
<212> TYPE: PRT
<213> ORGANISM: Homo sapiens

<400> SEQUENCE: 66

Lys Ile Gln Val Leu Gln Gln Gln Ala Asp Asp Ala Glu Glu Arg Ala
1               5                   10                  15

<210> SEQ ID NO 67
<211> LENGTH: 17
<212> TYPE: PRT
<213> ORGANISM: Homo sapiens

<400> SEQUENCE: 67

Arg Lys Ile Gln Val Leu Gln Gln Gln Ala Asp Asp Ala Glu Glu Arg
1               5                   10                  15

Ala

<210> SEQ ID NO 68
<211> LENGTH: 11
<212> TYPE: PRT
<213> ORGANISM: Homo sapiens

<400> SEQUENCE: 68

Lys Met Glu Leu Gln Glu Ile Gln Leu Lys Glu
1               5                   10

<210> SEQ ID NO 69
<211> LENGTH: 13
<212> TYPE: PRT
<213> ORGANISM: Homo sapiens

<400> SEQUENCE: 69

Arg Met Leu Asp Gln Thr Leu Leu Asp Leu Asn Glu Met
1               5                   10

<210> SEQ ID NO 70
<211> LENGTH: 10
<212> TYPE: PRT

```
<213> ORGANISM: Homo sapiens

<400> SEQUENCE: 70

Lys Cys Leu Ser Ala Ala Glu Glu Lys Tyr
1               5                   10

<210> SEQ ID NO 71
<211> LENGTH: 16
<212> TYPE: PRT
<213> ORGANISM: Homo sapiens

<400> SEQUENCE: 71

Lys Ile Gln Ala Leu Gln Gln Gln Ala Asp Glu Ala Glu Asp Arg Ala
1               5                   10                  15

<210> SEQ ID NO 72
<211> LENGTH: 17
<212> TYPE: PRT
<213> ORGANISM: Homo sapiens

<400> SEQUENCE: 72

Arg Lys Ile Gln Ala Leu Gln Gln Gln Ala Asp Glu Ala Glu Asp Arg
1               5                   10                  15

Ala

<210> SEQ ID NO 73
<211> LENGTH: 13
<212> TYPE: PRT
<213> ORGANISM: Homo sapiens

<400> SEQUENCE: 73

Arg Lys Leu Val Ile Leu Glu Gly Glu Leu Glu Arg Ala
1               5                   10

<210> SEQ ID NO 74
<211> LENGTH: 21
<212> TYPE: PRT
<213> ORGANISM: Homo sapiens

<400> SEQUENCE: 74

Lys Glu Glu Asn Val Gly Leu His Gln Thr Leu Asp Gln Thr Leu Asn
1               5                   10                  15

Glu Leu Asn Cys Leu
            20

<210> SEQ ID NO 75
<211> LENGTH: 14
<212> TYPE: PRT
<213> ORGANISM: Homo sapiens

<400> SEQUENCE: 75

Arg Glu Lys Ala Glu Gly Asp Val Ala Ala Leu Asn Arg Arg
1               5                   10

<210> SEQ ID NO 76
<211> LENGTH: 11
<212> TYPE: PRT
<213> ORGANISM: Homo sapiens

<400> SEQUENCE: 76

Lys Met Glu Ile Gln Glu Met Gln Leu Lys Glu
1               5                   10
```

```
<210> SEQ ID NO 77
<211> LENGTH: 15
<212> TYPE: PRT
<213> ORGANISM: Homo sapiens

<400> SEQUENCE: 77

Lys Tyr Ser Glu Lys Glu Asp Lys Tyr Glu Glu Glu Ile Lys Leu
1               5                   10                  15

<210> SEQ ID NO 78
<211> LENGTH: 11
<212> TYPE: PRT
<213> ORGANISM: Homo sapiens

<400> SEQUENCE: 78

Lys Cys Gly Asp Leu Glu Glu Glu Leu Lys Asn
1               5                   10

<210> SEQ ID NO 79
<211> LENGTH: 10
<212> TYPE: PRT
<213> ORGANISM: Homo sapiens

<400> SEQUENCE: 79

Lys Thr Ile Asp Asp Leu Glu Glu Lys Leu
1               5                   10

<210> SEQ ID NO 80
<211> LENGTH: 15
<212> TYPE: PRT
<213> ORGANISM: Homo sapiens

<400> SEQUENCE: 80

Lys Ala Ser Asp Ala Glu Gly Asp Val Ala Ala Leu Asn Arg Arg
1               5                   10                  15
```

METHODS AND COMPOSITIONS FOR THE DIAGNOSIS OF OVARIAN CANCER

CROSS-REFERENCE TO RELATED APPLICATIONS

This application is a divisional of U.S. patent application Ser. No. 14/045,452, filed Oct. 3, 2013, which claims the benefit of the priority of US Provisional Patent Application No. 61/709,695, filed Oct. 4, 2012. These applications are incorporated herein by reference in their entirety.

STATEMENT REGARDING FEDERALLY SPONSORED RESEARCH OR DEVELOPMENT

This invention was made with government support under Grant Nos. CA131582 and CA10815, awarded by the National Institutes of Health. The government has certain rights in this invention.

BACKGROUND OF THE INVENTION

Epithelial ovarian cancer (EOC) is the most lethal gynecological cancer in the United States and the fifth-leading cause of cancer-related death in women in the United States. An estimated 22,280 new cases were detected and 15,500 deaths occurred in the US in 2012. When diagnosed early (Stages I/II), treatment is generally successful, with a five-year survival rate of up to 90%. Unfortunately, most cases are not detected until after the cancer has spread, resulting in a dismal five-year survival rate for patients with advanced disease (stages III and IV) of 30% or less. The high mortality rate of ovarian cancer is due largely to the lack of effective screening tests for early detection or diagnosis of EOC.

Current screening methods for ovarian cancer typically use a combination of pelvic examination, transvaginal ultrasonography, and assays for protein biomarkers, such as serum cancer antigen 125 (CA-125). CA125 is recognized as a poor protein biomarker for early detection due to its high false positive rate and poor sensitivity and specificity. Assays for human epididymis protein-4 (HE4), or multivariate OVA1 are only approved for monitoring disease recurrence, therapeutic response, or for use in managing women with an ovarian adnexal mass.

A recently completed study comparing many of these protein biomarkers showed that none of them performed better than CA125 as a biomarker for ovarian cancer. A few groups also have used panels of biomarkers and obtained better sensitivity and specificity than CA125 alone when used in diagnostic samples. However, a recent study found that available biomarker panels did not outperform CA125 when used in prediagnostic samples.

Compositions and methods are urgently needed to diagnose early-stage EOC with high sensitivity and specificity and for clinical management of the disease after initial diagnosis.

SUMMARY OF THE INVENTION

In one aspect, a diagnostic reagent or device comprises the biomarker chloride intracellular channel protein 4 (CLIC4) or an isoform, pro-form, modified molecular form, or unique peptide fragment or nucleic acid fragment thereof. In another aspect, a diagnostic reagent or device comprises a ligand capable of specifically complexing with, binding to, or quantitatively detecting or identifying the biomarker chloride intracellular channel protein 4 (CLIC4) or an isoform, pro-form, modified molecular form, or unique peptide fragment or nucleic acid fragment thereof. In certain embodiments, the biomarker sequence or ligand in the reagent or device is associated with a molecule or moiety capable alone or in combination with one or more additional molecules of generating a detectable signal. In other embodiments, the biomarker sequence or ligand in the reagent or device is associated with a substrate on which the sequence or ligand is immobilized.

In another aspect, a diagnostic reagent or device comprises one or more tropomyosin proteins, e.g., TPM1, TPM2, TPM3, TPM4, or a common or shared sequence formed of two or more TPM proteins or an isoform, pro-form, modified molecular form, unique peptide fragment or nucleic acid fragment thereof, or proteins in the same biomarker family or expressed from a related gene, having at least 20% sequence homology or sequence identity with any tropomyosin biomarker. In another aspect, a diagnostic reagent or device comprises a ligand capable of specifically complexing with, binding to, or quantitatively detecting one or more tropomyosin proteins, e.g., TPM1, TPM2, TPM3, TPM4, or a common or shared sequence in two or more TPM proteins or an isoform, pro-form, modified molecular form, or unique peptide fragment or nucleic acid fragment thereof or proteins in the same biomarker family or expressed from a related gene, having at least 20% sequence homology or sequence identity with any tropomyosin biomarker. In certain embodiments, the biomarker sequences or ligand(s) in the reagent or device are associated with a molecule or moiety capable alone or in combination with one or more additional molecules of generating a detectable signal. In other embodiments, the biomarker sequences or ligand(s) in the reagent or device are associated with a substrate on which the ligand is immobilized.

In still a further aspect, the diagnostic reagent or device comprises a set of multiple biomarkers or multiple ligands to biomarkers, each ligand individually capable of specifically complexing with, binding to, or quantitatively detecting or identifying a single biomarker. In one embodiment of such diagnostic reagents or devices, one required biomarker is CLIC4. In another embodiment of such diagnostic reagents or devices, required biomarkers are one or more tropomyosin proteins, e.g., TPM1, TPM2, TPM3, TPM4, or a common or shared sequence in two or more TPM proteins, as defined herein.

In still another aspect, the diagnostic reagent or devices described above further comprise a set of multiple biomarkers or multiple ligands, each ligand individually capable of specifically complexing with, binding to, or quantitatively detecting or identifying a single biomarker, depending upon whether the reagent is formed of biomarker sequences or ligands to biomarker sequences. The additional biomarker is one that indicates the presence of ovarian cancer in a human subject. The biomarker sequences or fragments are derived from the selected additional biomarker. Each additional ligand is capable of specifically complexing with, binding to, or quantitatively detecting, or identifying the additional biomarker. In one embodiment, the additional marker is chloride intracellular channel protein 1 (CLIC1) or an isoform, pro-form, modified molecular form, or unique peptide fragment or unique nucleic acid fragment of the additional biomarker or proteins in the same biomarker family or expressed from a related gene, having at least 20% sequence homology or sequence identity with any tropomyosin biomarker.

In one embodiment in which at least a required biomarker is CLIC4, the additional biomarker is one or more tropomyosin proteins, e.g., TPM1, TPM2, TPM3, TPM4, or a common or shared sequence within two or more TPM proteins, or an isoform, pro-form, modified molecular form, or unique peptide fragment or unique nucleic acid fragment thereof, proteins in the same biomarker family or expressed from a related gene, having at least 20% sequence homology or sequence identity with any tropomyosin biomarker. In another embodiment, the biomarkers are CLIC4 and at least one or more additional biomarkers selected from one or multiple tropomyosin biomarker proteins 1 through 4, and/or CLIC1. Still additional ovarian cancer biomarkers can form part of the set of multiple markers.

In yet another aspect, a kit, panel or microarray comprising at least one diagnostic reagent with is a biomarker CLIC4 and/or one or more tropomyosins, or ligands capable of binding thereto, and optionally one or more reagents that are different ovarian cancer biomarkers discussed herein or ligands capable of binding thereto.

In a further aspect, a method for diagnosing or detecting or monitoring the progress of ovarian cancer in a subject is provided. In one embodiment, the method comprises contacting a sample obtained from a test subject with a diagnostic reagent or device comprising a ligand capable of specifically complexing with, binding to, or quantitatively detecting or identifying the biomarker chloride intracellular channel protein 4 (CLIC4) or an isoform, pro-form, modified molecular form, or unique peptide fragment or nucleic acid fragment thereof. The protein levels of CLIC4 (or peptides of CLIC4 serving as surrogates of the CLIC4 protein) are then detected or measured in the sample or from a protein level profile generated from the sample. The protein levels of the CLIC4 biomarker in the subject's are compared with the level of the same biomarker in a reference standard. A significant change in protein level of the subject's sample from that in the reference standard indicates a diagnosis, risk, or the status of progression or remission of ovarian cancer in the subject. In one embodiment of this method, an additional step involves detecting or measuring in the sample or from a protein level profile generated from the sample, the protein levels of one or more additional ovarian cancer biomarkers; and comparing the protein levels of the CLIC4 biomarker in relation to the levels of the additional biomarkers in the subject's sample with the same biomarkers in a reference standard or profile. Analogous methods are provided for other biomarkers or biomarker sets described herein.

In another aspect, use of any of the diagnostic reagents described herein in a method for the diagnosis of ovarian cancer is provided.

Other aspects and advantages of these compositions and methods are described further in the following detailed description of the preferred embodiments thereof.

BRIEF DESCRIPTION OF THE DRAWINGS

FIG. 2A is a sequence alignment of CLIC4 human (SwissProt Ref: Q9Y696; SEQ ID NO: 1) and 99% identical mouse (SwissProt Ref: Q9QYB1; SEQ ID NO: 2) CLIC4 sequence.

FIG. 2B is a sequence alignment of four human CLIC biomarkers expressed from different genes in the CLIC family. These biomarker gene products are of similar size and located in the 25-50 kDa region (CLIC1—SwissProt Ref: O00299; SEQ ID NO: 3; CLIC2—SwissProt Ref: O15247; SEQ ID NO: 4; CLIC3—SwissProt Ref: O95833; SEQ ID NO: 5; and CLIC4—SwissProt Ref: Q9Y696; SEQ ID NO: 1). Database identifiers are from the Swiss-Prot database. Tryptic sites (K or R) are indicated in bold—underlined sequences—peptides identified in the xenograft mouse serum. Grey highlight—peptides identified only in the patient serum pools. Lower case sequences—peptides identified in both the xenograft mouse and patient serum. Boxed sequences—peptides used for MRM quantitation.

FIG. 3 is a sequence alignment of selected isoforms of the biomarker TPM1, i.e., TPM1 isoform 5 SEQ ID NO: 6, TPM1 isoform 6 SEQ ID NO: 7, TPM1 variant SEQ ID NO: 8, TPM1 isoform CRA_i SEQ ID NO: 9, TPM1 variant 6 SEQ ID NO: 10, and TPM1 cDNA FLJ55130 SEQ ID NO: 11. TPM1 isoforms that contain all five xenograft-identified peptides (lower case sequences) were aligned using the Clustal algorithm. Two additional peptides (grey highlight) were subsequently identified in analyses of ovarian cancer patient sample pools. Inclusion of these peptides suggests the presence of TPM1 Q1ZYL5 or B7Z596. The database type (SP, Swiss-Prot entry; TR, TrEMBL entry), identifier, and brief description are indicated for each sequence. Tryptic sites (K or R) are indicated in bold. Boxed sequences—peptides used for MRM quantitation.

TABLE 1

Peptides represented in FIG. 4

| Biomarker | Peptide | SEQ ID NO: |
|---|---|---|
| TPM1 variant 6A (FIG. 4A) | ETAEADVASLNR | AA43-54 of SEQ ID NO: 10 |
| | SLQEQADAAEER | AA16-27 of SEQ ID NO: 10 |
| | LVIIESDLER | AA133-142 of SEQ ID NO: 10 |
| | AELSEGQVR | AA147-155 of SEQ ID NO: 10 |
| TPM3 (FIG. 4B) | IQVLQQQADDAEER | 12 |

TABLE 1-continued

Peptides represented in FIG. 4

| Biomarker | Peptide | SEQ ID NO: |
|---|---|---|
| TPM4 (FIG. 4C) | AEGDVAALNR | 13 |
|  | IQALQQQADEAEDR | 14 |
|  | [K]LVILEGELER | 15 |
| TPM (common) (FIG. 4D) | [R]IQLVEEELDR | 16 |

FIG. 5A is a scatter plot showing GeLC-MRM quantitation of the CLIC1 biomarker in serum of normal (n=6), benign (n=9), and ovarian cancer patients (15 Stage III, 3 Stage IV). P-values were calculated using the Mann-Whitney test with Bonferroni adjustment. Horizontal bars in each group indicate the median serum level of the protein. Peptides associated with this biomarker are shown in Table 5.

FIG. 5B is a scatter plot showing GeLC-MRM quantitation of the CLIC4 biomarker as described in FIG. 5A. Peptides associated with this biomarker are shown in Table 4.

FIG. 5C is a scatter plot showing GeLC-MRM quantitation of the TPM1, variant 6 biomarker as described in FIG. 5A. Peptides associated with this biomarker are shown in Table 6.

FIG. 5D is a scatter plot showing GeLC-MRM quantitation of the TPM3 biomarker as described in FIG. 5A. Peptides associated with this biomarker are shown in Table 7.

FIG. 5E is a scatter plot showing GeLC-MRM quantitation of the TPM4 biomarker as described in FIG. 5A. Peptides associated with this biomarker are shown in Table 7.

FIG. 5F is a scatter plot showing GeLC-MRM quantitation of the TPM family of biomarkers as described in FIG. 5A. The peptide common to all four gene products and used for this quantitation is shown in Table 8.

Figure 6A:
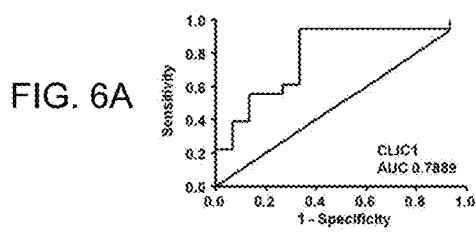

FIG. 6A is a ROC curve of the CLIC1 biomarker generated from Control (6 normal, 9 benign) and Cancer (15 Stage III, 3 Stage IV) datasets. The area under the ROC curve is indicated for each biomarker. The peptides associated with each biomarker are shown in Tables 4-8.

Figure 6B:
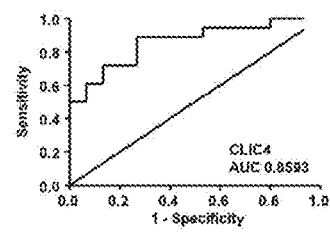

FIG. 6B is a ROC curve of the CLIC4 biomarker, as described in FIG. 6A.

Figure 6C:
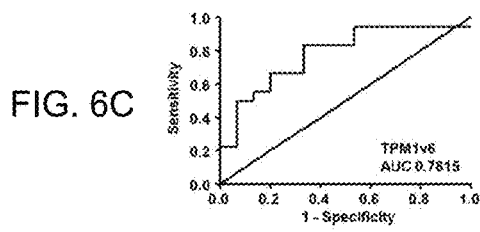

FIG. 6C is a ROC curve of the TPM1, variant 6 biomarker, as described in FIG. 6A.

Figure 6D:
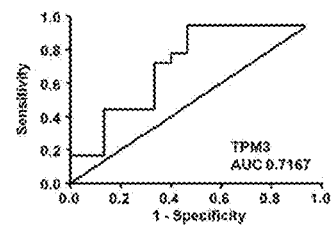

FIG. 6D is a ROC curve of the TPM3 biomarker, as described in FIG. 6A.

Figure 6E:
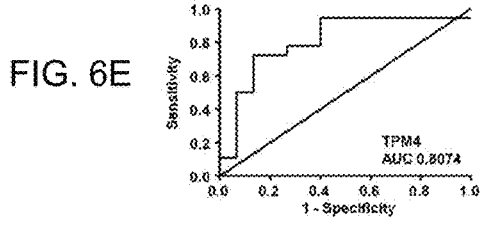

FIG. 6E is a ROC curve of the TPM4 biomarker, as described in FIG. 6A.

Figure 6F:
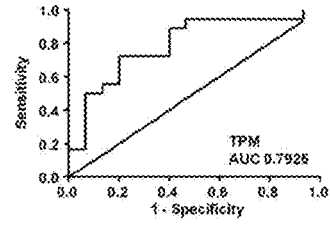

FIG. 6F is a ROC curve of the TPM family, as described in FIG. 6A.

DETAILED DESCRIPTION OF THE INVENTION

New serological biomarkers for early detection and clinical management of ovarian cancer are urgently needed, and many candidates have been reported. A major challenge frequently encountered when validating candidates in patients is establishing quantitative assays that distinguish between highly homologous proteins. It is important to differentiate between protein isoforms as well as related protein members of a family because these sequence differences are often associated with a vital distinct role that is critical to the protein structure or function. In this regard, any assay, including sandwich ELISA assays, could give misleading results if the biomarker specificity is unknown or if multiple related biomarker proteins are quantitated as a group.

The present inventors developed a gel-based, label-free MRM quantitation approach (GeLC-MRM) as a rapid, first-level biomarker verification strategy using human plasma or serum samples. As disclosed in the examples below, the inventors used in-depth GeLC-MS/MS analysis of patient serum pools and isoform-specific MRM assays (Tang et al, 2012, cited above; Tang, H. Y et al, *J Proteome Res* 2011, 10, (9), 4005-17; and Beer, L. A et al, *J Proteome Res* 2011, 10, (3), 1126-38) to identify and quantitate additional EOC biomarkers. Related proteins in two protein families were detected that significantly distinguished between cancer and control patients to a high sensitivity.

The inventors were able to use quantitative MRM assays to distinguish between all related protein members and the isoforms of certain members that were detectable in low abundance in pools of ovarian cancer patient sera. By using a combination of unique and shared peptides together with correlation and factor analysis, the inventors determined that such unidentified related proteins either do not occur at a significant level or change in parallel with the proteins explicitly defined by unique peptides. In summary, the inventors found that the CLIC4 biomarker and at least four tropomyosins biomarker proteins (TPM1 variant 6, TPM2, TPM3, and TPM4) are significantly elevated in ovarian cancer patients compared with non-cancer controls. These proteins, as well as the previously identified biomarkers CLIC1, PRDX6, and CTSD, among others identified in PCT/US2012/54136, are promising new EOC biomarkers for distinguishing between patient cohorts and diagnosing ovarian cancer from non-cancer controls. As such, they form the basis of novel diagnostic reagents and devices, as well as methods for diagnosing or detecting the existence or absence of, or monitoring the progress of, ovarian cancer in a subject. Such compositions and method use one or more of the biomarkers, e.g., CLIC4 in optional combination with one or more other ovarian cancer-associated biomarkers, or CLIC4 in combination with multiple related TPM proteins, to diagnose and monitor the progression and treatment of EOC.

Protein abundance levels of biomarkers in blood, in some embodiments, are dependent upon expression levels in tissues of origin (e.g., ovarian tumors), as well as rate of shedding into the blood and rate of clearance from the blood. While increased expression in a tumor often will correlate with increased abundance levels being observed in the blood, this is not necessarily always true. Therefore, the methods and compositions in one aspect refer to compositions that detect protein biomarkers and to protein assay methods. However, one of skill in the art, given the teachings contained herein, would readily understand that nucleic acid expression levels of the biomarkers and reagents and methods for their detections may be similarly practiced, without undue experimentation.

Diagnostic reagents that can detect and measure the target biomarkers and sets of biomarkers identified herein and methods for evaluating the level or ratios of these target biomarkers vs. their level(s) in a variety of reference standards or controls of different conditions or stages in ovarian cancer are valuable tools in the early detection and monitoring of ovarian cancer.

I. Definitions

"Patient" or "subject" as used herein means a female mammalian animal, including a human, a veterinary or farm animal, a domestic animal or pet, and animals normally used for clinical research. In one embodiment, the subject of these methods and compositions is a human.

By "biomarker" or "biomarker signature" as used herein is meant a single protein or a combination of proteins or peptide fragments thereof, the protein levels or relative protein levels or ratios of which significantly change (either in an increased or decreased manner) from the level or relative levels present in a subject having one physical condition or disease or disease stage from that of a reference standard representative of another physical condition or disease stage. Throughout this specification, wherever a particular biomarker is identified by name, it should be understood that the term "biomarker" includes CLIC4 and/or multiple related proteins of the tropomyosin families. These biomarkers may be combined to form certain sets of biomarkers or ligands to biomarkers in diagnostic reagents. Still other "additional" biomarkers are mentioned specifically herein in combination with CLIC4 and/or the multiple tropomyosin protein members. Biomarkers described in this specification include any physiological molecular forms, or modified physiological molecular forms, isoforms, proforms, and peptide fragments thereof, unless otherwise specified. It is understood that all molecular forms useful in this context are physiological, e.g., naturally occurring in the species. Preferably the peptide fragments obtained from the biomarkers are unique sequences, such as those exemplified below. However, it is understood that fragments other than those explicitly identified may be obtained readily by one of skill in the art in view of the teachings provided herein.

By "isoform" or "multiple molecular form" is meant an alternative expression product or variant of a single gene in a given species, including forms generated by alternative splicing, single nucleotide polymorphisms, alternative promoter usage, alternative translation initiation small genetic differences between alleles of the same gene, and posttranslational modifications (PTMs) of these sequences.

By "related proteins" or "proteins of the same family" are meant expression products of different genes or related genes identified as belonging to a common family. Related proteins in the same biomarker family may or may not share related functions. Related proteins can be readily identified as having significant sequence identity either over the entire protein or a significant part of the protein that is typically referred to as a "domain"; typically proteins with at least 20% sequence homology or sequence identity can be readily identified as belonging to the same protein family.

By "homologous protein" is meant an alternative form of a related protein produced from a related gene having a percent sequence similarity or identity of greater than 20%, greater than 30%, greater than 40%, greater than 50%, greater than 60%, greater than 70%, greater than 75%, greater than 80%, greater than 85%, greater than 90%, greater than 95%, greater than 97%, or greater than 99%.

"Reference standard" as used herein refers to the source of the reference biomarker levels. The "reference standard" is preferably provided by using the same assay technique as is used for measurement of the subject's biomarker levels in the reference subject or population, to avoid any error in standardization. The reference standard is, alternatively, a numerical value, a predetermined cutpoint, a mean, an average, a numerical mean or range of numerical means, a numerical pattern, a ratio, a graphical pattern or a protein abundance profile or protein level profile derived from the same biomarker or biomarkers in a reference subject or reference population. In an embodiment, in which expression of nucleic acid sequences encoding the biomarkers is desired to be evaluated, the reference standard can be an expression level of one or more biomarkers or an expression profile.

"Reference subject" or "Reference Population" defines the source of the reference standard. In one embodiment, the reference is a human subject or a population of subjects having no ovarian cancer, i.e., healthy controls or negative controls. In yet another embodiment, the reference is a human subject or population of subjects with one or more clinical indicators of ovarian cancer, but who did not develop ovarian cancer. In still another embodiment, the reference is a human subject or a population of subjects having benign ovarian nodules or cysts. In still another embodiment, the reference is a human subject or a population of subjects who had ovarian cancer, following surgical removal of an ovarian tumor. In another embodiment, the reference is a human subject or a population of subjects who had ovarian cancer and were evaluated for biomarker levels prior to surgical removal of an ovarian tumor. Similarly, in another embodiment, the reference is a human subject or a population of subjects evaluated for biomarker levels following therapeutic treatment for ovarian cancer. In still another embodiment, the reference is a human subject or a population of subjects prior to therapeutic treatment for an ovarian cancer. Similarly, in another embodiment, the reference human subject or a population of subjects without ovarian cancer but which tests positive for a protein level of CA-125 or HE4. Similarly, in another embodiment, the reference human subject or a population of subjects with ovarian cancer but which tests negative for a protein level of CA125 or HE4. In still other embodiments of methods described herein, the reference is obtained from the same test subject who provided a temporally earlier biological sample. That sample can be pre- or post-therapy or pre- or post-surgery.

Other potential reference standards are obtained from a reference that is a human subject or a population of subjects having early stage ovarian cancer. In another embodiment the reference is a human subject or a population of subjects having advanced stage ovarian cancer. In still another embodiment, the reference is a human subject or a population of subjects having a subtype of epithelial ovarian cancer. In still another embodiment, the reference is a human subject or a population of subjects having serous ovarian cancer or serous papillary adenocarcinoma. In still another embodiment, the reference is a human subject or a population of subjects having mucinous ovarian cancer. In still another embodiment, the reference is a human subject or a population of subjects having clear cell ovarian cancer. In still another embodiment, the reference is a subject or a population of subjects having endometrioid ovarian cancer. In another embodiment, the reference is a human subject or a population of subjects having Mullerian ovarian cancer. In another embodiment, the reference is a human subject or a population of subjects having undifferentiated ovarian cancer or an ovarian sarcoma. In another embodiment, the reference standard is a combination of two or more of the above reference standards.

Selection of the particular class of reference standards, reference population, biomarker levels or profiles depends upon the use to which the diagnostic/monitoring methods and compositions are to be put by the physician and the desired result, e.g., initial diagnosis of ovarian cancer or other ovarian condition, clinical management of patients with ovarian cancer after initial diagnosis, including, but not limited to, monitoring for reoccurrence of disease or monitoring remission or progression of the cancer and either before, during or after therapeutic or surgical intervention, selecting among therapeutic protocols for individual patients, monitoring for development of toxicity or other complications of therapy, predicting development of therapeutic resistance, and the like. Such reference standards or controls are the types that are commonly used in similar diagnostic assays for other biomarkers.

"Sample" as used herein means any biological fluid or tissue that contains the ovarian cancer biomarkers identified herein. The most suitable samples for use in the methods and with the compositions are samples which require minimal invasion for testing, e.g., blood samples, including serum, plasma, whole blood, and circulating tumor cells. It is also anticipated that other biological fluids, such as saliva or urine, vaginal or cervical secretions, and ascites fluids or peritoneal fluid may be similarly evaluated by the methods described herein. Also, circulating tumor cells or fluids containing them are also suitable samples for evaluation in certain embodiments of this invention. The samples may include biopsy tissue, tumor tissue, surgical tissue, circulating tumor cells, or other tissue. Such samples may further be diluted with saline, buffer or a physiologically acceptable diluent. Alternatively, such samples are concentrated by conventional means. In certain embodiments, e.g., those in which expression levels of nucleic acid sequences encoding the biomarkers are desired to be evaluated, the samples may include biopsy tissue, surgical tissue, circulating tumor cells, or other tissue. In one embodiment, the sample is a tumor secretome, i.e., any fluid or medium containing the proteins secreted from the tumor. These shed proteins may be unassociated, associated with other biological molecules, or enclosed in a lipid membrane such as an exosome. In another embodiment, the sample is plasma.

By "significant change in protein level" is meant an increased protein level of a selected biomarker in comparison to that of the selected reference standard or control or relative to a predetermined cutpoint; a decreased protein level of a selected biomarker in comparison to that of the selected reference or control or relative to a predetermined cutpoint; or a combination of a pattern or relative pattern of certain increased and/or decreased biomarkers.

The degree of change in biomarker protein level can vary with each individual and is subject to variation with each population. For example, in one embodiment, a large change, e.g., 2-3 fold increase or decrease in protein levels of a small number of biomarkers, e.g., from 1 to 9 characteristic biomarkers, is statistically significant. In another embodiment, a smaller relative change in 10 or more (i.e., about 10, 20, 24, 29, or 30 or more biomarkers) is statistically significant. The degree of change in any biomarker(s) expression varies with the condition, such as type of ovarian cancer and with the size or spread of the cancer or solid tumor. The degree of change also varies with the immune response of the individual and is subject to variation with each individual. For example, in one embodiment of this invention, a change at or greater than a 1.2 fold increase or decrease in protein level of a biomarker or more than two such biomarkers, or even 3 or more biomarkers, is statistically significant. In another embodiment, a larger change, e.g., at or greater than a 1.5 fold, greater than 1.7 fold or greater than 2.0 fold increase or a decrease in expression of a biomarker(s) is statistically significant. This is particularly true for cancers without solid tumors. Still alternatively, if a single biomarker protein level is significantly increased in biological samples which normally do not contain measurable protein levels of the biomarker, such increase in a single biomarker level may alone be statistically significant. Conversely, if a single biomarker protein level is normally decreased or not significantly measurable in certain biological samples which normally do contain measurable protein levels of the biomarker, such decrease in protein level of a single biomarker may alone be statistically significant.

A change in protein level of a biomarker required for diagnosis or detection by the methods described herein refers to a biomarker whose protein level is increased or decreased in a subject having a condition or suffering from a disease, specifically ovarian cancer, relative to its expression in a reference subject or reference standard. Biomarkers may also be increased or decreased in protein level at different stages of the same disease or condition. The protein levels of specific biomarkers differ between normal subjects and subjects suffering from a disease, benign ovarian nodules, or cancer, or between various stages of the same disease. Protein levels of specific biomarkers differ between pre-surgery and post-surgery patients with ovarian cancer. Such differences in biomarker levels include both quantitative, as well as qualitative, differences in the temporal or relative protein level or abundance patterns among, for example, biological samples of normal and diseased subjects, or among biological samples which have undergone different disease events or disease stages. For the purpose of this invention, a significant change in biomarker protein levels when compared to a reference standard is considered to be present when there is a statistically significant ($p<0.05$) difference in biomarker protein level between the subject and reference standard or profile, or significantly different relative to a predetermined cut-point.

For example, in one embodiment, the test subject's biomarker(s) levels are compared with a healthy reference standard. If the subject has ovarian cancer, the selected EOC biomarker(s), e.g., CLIC 4 and/or TPM1, 2, 3, and/or 4, will typically show a change in protein level from the levels in the healthy reference standard, thus permitting diagnosis of ovarian cancer. In another example, these biomarker(s) differentially change in protein level (either by increased or decreased protein level) when the biomarker levels or relative levels from the sample of a subject having one of the following conditions is compared to a reference subject or population having another of the following physical conditions. These "conditions" include no ovarian cancer, the presence of benign ovarian nodules, the presence of an ovarian cancer or subtype, the condition following surgical removal of an ovarian tumor; the condition prior to surgical removal of an ovarian tumor; the condition following a specific therapeutic treatment for an ovarian tumor; the condition prior to a specific therapeutic treatment for an ovarian tumor. It is further anticipated that the biomarker(s) expression levels may change and the changes may be detected during treatment for ovarian cancer. In another embodiment, a condition includes that of a subject having undiagnosed clinical symptoms of abdominal pain or other abdominal condition of unknown origin. Still other embodiments of "conditions" as defined above include early stage ovarian cancer; advanced stage ovarian cancer, a subtype of epithelial ovarian cancer, serous ovarian cancer; mucinous ovarian cancer, clear cell ovarian cancer, endometrioid ovarian cancer, Mullerian ovarian cancer; undifferentiated ovarian cancer, serous papillary adenocarcinoma; and sarcoma.

The term "ligand" refers with regard to protein biomarkers to a molecule that binds or complexes, with a biomarker protein, molecular form or peptide, such as an antibody, antibody mimic or equivalent that binds to or complexes with a biomarker identified herein, a molecular form or fragment thereof. In certain embodiments, in which the biomarker expression is to be evaluated, the ligand can be a nucleotide sequence, e.g., polynucleotide or oligonucleotide, primer or probe.

As used herein, the term "antibody" refers to an intact immunoglobulin having two light and two heavy chains or fragments thereof capable of binding to a biomarker protein or a fragment of a biomarker protein. Thus a single isolated antibody or fragment may be a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, an Fv construct, a Fab construct, an Fc construct, a light chain variable or complementarity determining region (CDR) sequence, etc.

As used herein, "labels" or "reporter molecules" are chemical or biochemical moieties useful for labeling a ligand, e.g., amino acid, peptide sequence, protein, or antibody. "Labels" and "reporter molecules" include fluorescent agents, chemiluminescent agents, chromogenic agents, quenching agents, radionucleotides, enzymes, substrates, cofactors, inhibitors, radioactive isotopes, magnetic particles, and other moieties known in the art. "Labels" or "reporter molecules" are capable of generating a measurable signal and may be covalently or noncovalently joined to a ligand.

As used herein the term "cancer" refers to or describes the physiological condition in mammals that is typically characterized by unregulated cell growth. More specifically, as used herein, the term "cancer" means any ovarian cancer. In one embodiment, the ovarian cancer is an epithelial ovarian cancer or subtype as referred to in "conditions" above. In still an alternative embodiment, the cancer is an "early stage" (I or II) ovarian cancer. In still another embodiment, the cancer is a "late stage" (III or IV) ovarian cancer.

The term "tumor," as used herein, refers to all neoplastic cell growth and proliferation, whether malignant or benign, and all pre-cancerous and cancerous cells and tissues.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

The term "microarray" refers to an ordered arrangement of binding/complexing array elements or ligands, e.g. antibodies, on a substrate.

In the context of the compositions and methods described herein, reference to "at least two," "at least five," etc. of the biomarkers listed in any particular biomarker set means any and all combinations of the biomarkers identified. Specific biomarkers for the biomarker profile do for use in this invention include CLIC4, but may also include any biomarker, fragment or molecular form, as discussed herein.

By "significant change in expression" is meant an upregulation in the expression level of a nucleic acid sequence, e.g., genes or transcript, encoding a selected biomarker, in comparison to the selected reference standard or control; a downregulation in the expression level of a nucleic acid sequence, e.g., genes or transcript, encoding a selected biomarker, in comparison to the selected reference standard or control; or a combination of a pattern or relative pattern of certain upregulated and/or down regulated biomarker genes. The degree of change in biomarker expression can vary with each individual as stated above for protein biomarkers.

The term "polynucleotide," when used in singular or plural form, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The term "polynucleotide" specifically includes cDNAs. The term includes DNAs (including cDNAs) and RNAs that contain one or more modified bases. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide of less than 20 bases, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

One skilled in the art may readily reproduce the compositions and methods described herein by use of the amino acid sequences of the biomarkers and other molecular forms, which are publicly available from conventional sources.

It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" is used interchangeably herein.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

II. Biomarkers and Biomarker Signatures Useful in the Methods and Compositions

The "targets" of the compositions and methods of these inventions include, in one aspect, CLIC4, optionally with other biomarkers identified herein, fragments, particularly unique fragments thereof, and molecular forms thereof. In certain embodiments, superior diagnostic tests for diagnosing the existence of ovarian cancer utilize at least one of the ligands that bind or complex with CLIC4, or one of the fragments or molecular forms thereof. In other embodiments, superior diagnostic tests for distinguishing ovarian cancer from one of the conditions recited above utilize multiple ligands, each individually detecting a different specific target biomarker identified herein, or isoform, modified form or peptide thereof. In still other methods, no ligand is necessary, e.g., MRM assays.

Thus, in one aspect, the target biomarker of the methods and compositions described herein is chloride intracellular channel protein 4 (CLIC4) or an isoform, pro-form, modified molecular form, or unique peptide fragment or nucleic acid fragment thereof. The amino acid sequences for CLIC4 and its molecular forms are publically available, such as in GENBANK. In one embodiment, the biomarker CLIC4 is Uniprot ID no. Z9Y696 or a peptide fragment thereof. Certain fragments of CLIC4 that may be useful as targets in the methods and compositions described herein include one or more peptide fragments, such as, but not limited to, those identified below. It should be understood that, depending upon the context, any reference to CLIC4 herein also refers to a peptide and the molecular form thereof, as well as the nucleotide sequences encoding CLIC4 and/or any of its unique peptides or forms. Among such fragments useful for detection of CLIC4 are

```
(a)
aa 49-60 of SEQ ID NO: 1
GVVFSVTTVDLK, (b)
aa 151-172 of SEQ ID NO: 1
LDEYLNSPLPDEIDENSMEDIK, (c)
aa 131-142 of SEQ ID NO: 1
NSRPEANEALER, (d)
aa 20-27 of SEQ ID NO: 1
YLTNAYSR, (d)
aa 139-249 of SEQ ID NO: 1
EVEIAYSDVAK, (e)
aa 41-48 of SEQ ID NO: 1
LFMILWLK, (f)
aa 228-238 of SEQ ID NO: 1
DEFTNTCPSDK, (g)
aa 91-103 of SEQ ID NO: 1
IEEFLEEVLCPPK, (h)
aa 178-194 of SEQ ID NO: 1
FLDGNEMTLADCNLLPK, (i)
aa 12-24 of SEQ ID NO: 1
EEDKEPLIELFVK,
or (j)
aa 111-124 of SEQ ID NO: 1
HPESNTAGMDIFAK, .
```

In some embodiments, the methionine in each sequence is the oxidized form; in other embodiments, the methionine in each sequence is in the unoxidized form.

In another embodiment the target biomarker of the methods and compositions described herein is Tropomyosin 1 (TPM1), as described in International Patent Application No. PCT/US12/54136. The amino acid sequence for TPM1 is publically available, such as in GENBANK. In one embodiment, an isoform of TPM1 is TPM1, variant 6 (UniProt ID No. Q1ZYL5) or TPM1, variant 8 (UniProt ID No. B7Z596). Certain fragments of TPM1 may also be useful as targets in the methods and compositions described herein. It should be understood that, depending upon the context, any reference to TPM1 herein also refers to any of its peptides or molecular forms, as well as the nucleotide sequences encoding TPM1 and/or any of the peptides.

In another embodiment the target biomarker of the methods and compositions described herein is Tropomyosin 2 (TPM2). The amino acid sequence for TPM2 is publically available, such as in GENBANK. In another embodiment, an isoform of TPM2 is TPM2 beta chain (UniProt ID No. UR1H_P07951, UR1H_Q5TCU3, or UR1H_Q5TCU8) or TPM2, isoform 2 (UniProt ID No. P07951-2, A7XZE4). Certain fragments of TPM2 may also be useful as targets in the methods and compositions described herein. It should be understood that, depending upon the context, any reference to TPM2 herein also refers to any of its peptides or molecular forms, as well as the nucleotide sequences encoding TPM2 and/or any of the peptides.

In another embodiment the target biomarker of the methods and compositions described herein is Tropomyosin 3 (TPM3). The amino acid sequence for TPM3 is publically available, such as in GENBANK. In still another embodiment, an isoform of TPM3 is TPM3 alpha-3 chain (UniProt ID No. P06753, Q5VU59, Q5HYB6, B2RDE1, or E2RB38). Certain fragments of TPM3 may also be useful as targets in the methods and compositions described herein. It should be understood that, depending upon the context, any reference to TPM3 herein also refers to any of its peptides or molecular forms, as well as the nucleotide sequences encoding TPM3 and/or any of the peptides.

In another embodiment the target biomarker of the methods and compositions described herein is Tropomyosin 4 (TPM4). The amino acid sequence for TPM4 is publically available, such as in GENBANK. In a further embodiment, an isoform of TPM4 is TPM4 alpha-4 chain (UniProt ID No. P6736), or TPM4, Isoform 2 (UniProt ID No. P67936-2). Certain fragments of TPM4 may also be useful as targets in the methods and compositions described herein, e.g., Table 3. It should be understood that, depending upon the context, any reference to TPM4 herein also refers to any of its peptides or molecular forms, as well as the nucleotide sequences encoding TPM4 and/or any of the peptides.

In another embodiment the target biomarker of the methods and compositions described herein is a peptide sequence shared by two or more members of the related family of tropomyosin proteins TPM1, TPM2, TPM3 and TPM4. A common amino acid sequence for TPM or fragments thereof can be readily generated using and aligning the publically known sequences for the native TPM family members. It should be understood that, depending upon the context, any reference to common TPM herein also refers to any of its fragments or peptides derived therefrom or the common sequence generated by use of 2 or more of the TPM related proteins to generate the alignment.

In still other embodiments, the target biomarker(s) are multiple members of the related family of tropomyosin proteins, such as tropomyosin 1 (TPM1); tropomyosin 2 (TPM2); tropomyosin 3 (TPM3); tropomyosin 4 (TPM4); or a common sequence shared by two or more of these related proteins.

In still another embodiment, the target biomarker is actually a set of targets, which set contains CLIC4 (as defined above) and one or more additional EOC target biomarkers. In still another embodiment, the target biomarker is actually a set of targets, which set contains two or more related TPM family proteins or a TPM common or shared peptide or protein (as defined above) and one or more additional EOC target biomarkers. It should be understood that wherever in a following list of biomarker sets, a TPM biomarker is identified, it could be replaced or used with a common or shared TPM sequence.

Thus, among other embodiments, a set of biomarkers can be one of the following sets: CLIC4, TPM1 or CLIC4, TPM2 or CLIC4, TPM3 or CLIC4, TPM4, or CLIC4, TPM1, TPM2, or CLIC4, TPM1, TPM2, TPM3, or CLIC4, TPM1, TPM2, TPM3, TPM4, or CLIC4, TPM2, TPM3 or CLIC4, TPM2, TPM3, TPM4, or CLIC4, TPM3, TPM4, or CLIC4, TPM2, TPM4, or CLIC4, TPM1, TPM3.

However, still other additional biomarkers can include any of the biomarkers identified in International Patent Application No. PCT/US12/54136, such as CLIC 1 or an isoform, pro-form, modified molecular form, or unique peptide fragment or unique nucleic acid fragment thereof. The amino acid sequence for CLIC1 is publically available, such as in GENBANK. Certain fragments of CLIC1 that may be useful as targets in the methods and compositions described herein include one or more peptide fragments, such as, but not limited to, those identified herein. It should be understood that, depending upon the context, any reference to CLIC1 herein also refers to any of these peptides, or any molecular form of the biomarker, as well as the nucleotide sequences encoding CLIC1 and/or any of the peptides. Among useful fragments of CLIC1 include

```
(a)
aa38-49 of SEQ ID NO: 3
GVTFNVTTVDTK, ;

(b)
aa96-113 of SEQ ID NO: 3
LAALNPESNTAGLDIFAK, ;
or (c)
aa120-131 of SEQ ID NO: 3
NSNPALNDNLEK, .
```

Thus, in another embodiment, a desirable set of target biomarkers includes, without limitation: CLIC4 and CLIC1, or CLIC4, CLIC1, TPM1, or CLIC4, CLIC1, TPM2, or CLIC4, CLIC1, TPM3, or CLIC4, CLIC1, TPM4, or CLIC4, CLIC1, TPM1, TPM2, or CLIC4, CLIC1, TPM1, TPM2, TPM3, or CLIC4, CLIC1, TPM1, TPM2, TPM3, TPM4 or CLIC4, CLIC1, TPM2, TPM3, or CLIC4, CLIC1, TPM2, TPM3, TPM4, or CLIC4, CLIC1, TPM3, TPM4, or CLIC4, CLIC1, TPM1, TPM3, or CLIC4, CLIC1, TPM2, TPM4. In another embodiment, a desirable set of target biomarkers includes, without limitation: CLIC1, TPM2, or CLIC1, TPM3, or CLIC1, TPM4, or CLIC1, TPM1, TPM2, or CLIC1, TPM1, TPM2, TPM3, or CLIC1, TPM1, TPM2, TPM3, TPM4 or CLIC1, TPM2, TPM3, or CLIC1, TPM2, TPM3, TPM4, or CLIC1, TPM3, TPM4, or CLIC1, TPM1, TPM3, or CLIC1, TPM2, TPM4.

Still other sets of target biomarkers that include either CLIC4 and/or multiple TPM biomarkers as described above, can further include other known EOC biomarkers, which may be added to the above-identified sets either individually or in groups. In certain embodiments, the additional biomarker is cathepsin D-30 kDa (CTSD-30) or an isoform, pro-form, modified molecular form, or unique peptide fragment or unique nucleic acid fragment thereof, proteins in the same biomarker family or expressed from a related gene, having at least 20% sequence homology or sequence identity with CTSD-30. In other embodiments, the additional biomarker is peroxieredoxin-6 (PRDX6) or an isoform, pro-form, modified molecular form, or unique peptide fragment or unique nucleic acid fragment thereof, or proteins in the same biomarker family or expressed from a related gene, having at least 20% sequence homology or sequence identity with PRDX6. In still other embodiments, the additional biomarker is the known EOC biomarker CA125, or an isoform, pro-form, modified molecular form, or unique peptide fragment therefrom or proteins in the same biomarker family or expressed from a related gene, having at least 20% sequence homology or sequence identity with CA125. In still other embodiments, the additional biomarker is the known EOC biomarker HE4, or an isoform, pro-form, modified molecular form, or unique peptide fragment therefrom or proteins in the same biomarker family or expressed from a related gene, having at least 20% sequence homology or sequence identity with HE4. In other embodiments, the additional biomarker is bisphosphoglycerate mutase (BPGM) or an isoform, pro-form, modified molecular form, or unique peptide fragment or unique nucleic acid fragment thereof, or proteins in the same biomarker family or expressed from a related gene, having at least 20% sequence homology or sequence identity with BPGM. In other embodiments, the additional biomarker is proteasome subunit alpha type-7 (PSMA7) or an isoform, pro-form, modified molecular form, or unique peptide fragment or unique nucleic acid fragment thereof, or proteins in the same biomarker family or expressed from a related gene, having at least 20% sequence homology or sequence identity with PSMA7. In other embodiments, the additional biomarker is aldose reductase (AKR1B1) or an isoform, pro-form, modified molecular form, or unique peptide fragment or unique nucleic acid fragment thereof, or proteins in the same biomarker family or expressed from a related gene, having at least 20% sequence homology or sequence identity with AKR1B1. In other embodiments, the additional biomarker is homeobox protein (HMX1) or an isoform, pro-form, modified molecular form, or unique peptide fragment or unique nucleic acid fragment thereof, or proteins in the same biomarker family or expressed from a related gene, having at least 20% sequence homology or sequence identity with HMX1. In other embodiments, the additional biomarker is melastatin 1 (TRPM1) or an isoform, pro-form, modified molecular form, or unique peptide fragment or unique nucleic acid fragment thereof, or proteins in the same biomarker family or expressed from a related gene, having at least 20% sequence homology or sequence identity with TRPM1. In other embodiments, the additional biomarker is protein CutA (CUTA) or an isoform, pro-form, modified molecular form, or unique peptide fragment or unique nucleic acid fragment thereof, or proteins in the same biomarker family or expressed from a related gene, having at least 20% sequence homology or sequence identity with CUTA. In other embodiments, the additional biomarker is SERPINB12 protein (SERPINB12), or an isoform, pro-form, modified molecular form, or unique peptide fragment or unique nucleic acid fragment thereof, or proteins in the same biomarker family or expressed from a related gene, having at least 20% sequence homology or sequence identity with SERPINB12. In other embodiments, the additional biomarker is cathepsin D-52 kDa (CTSD-52) or an isoform, pro-form, modified molecular form, or unique peptide fragment or unique nucleic acid fragment thereof, or proteins in the same biomarker family or expressed from a related gene, having at least 20% sequence homology or sequence identity with CTSD-52.

In still other multiple biomarker combinations with either CLIC4 and/or multiple TPM biomarkers or a TPM common or shared biomarker, include, without limitation, or consist of, the following exemplary combinations of biomarkers or combinations that include different molecular forms of the same biomarker, for diagnosis of ovarian cancer or for monitoring the progression of the severity of disease or remission of disease:

CLIC4 with one or more of CLIC1, PRDX6, BPGM, PSMA7, AKRIB1, HMX1, TRPM1, CUTA, SERPINB12, CTSD-30 kDa or CTSD-52 kDa; or CLIC4 and one or multiple TPM 1-4, as above, with one or more of CLIC1, PRDX6, BPGM, PSMA7, AKRIB1, HMX1, TRPM1, CUTA, SERPINB12, CTSD-30 kDa or CTSD-52 kDa; or CLIC4 with one or more of CLIC1, PRDX6, BPGM, PSMA7, AKRIB1, HMX1, TRPM1, CUTA, SERPINB12, CTSD-30 kDa or CTSD-52 kDa, and CA125 and/or HE4; or CLIC4 and one or multiple TPM 1-4, as above, with CLIC1, PRDX6, BPGM, PSMA7, AKRIB1, HMX1, TRPM1, CUTA, SERPINB12, CTSD-30 kDa or CTSD-52 kDa, and CA125 and/or HE4.

In still another aspect, a biomarker combination includes, without limitation, or consists of, the following exemplary combinations of biomarkers for diagnosis of ovarian cancer or for monitoring the progression of the severity of disease or remission of disease:

CLIC4, CTSD-30 kDa, and/or CLIC1, and/or PRDX6, or CLIC4, CTSD-30 kDa, CLIC1, and PRDX6;

CLIC4, CTSD-30 kDa, CLIC1, PRDX6 and at least two TPM proteins selected from TPM1, TPM2, TPM3, TPM4 or common or shared TPM;

CLIC4, CTSD-30 kDa, CLIC1, PRDX6 and BPGM,

CLIC4, CTSD-30 kDa, CLIC1, PRDX6 and PSMA7,

CLIC4, CTSD-30 kDa, CLIC1, PRDX6, BPGM, and at least two TPM proteins selected from TPM1, TPM2, TPM3, TPM4 or common or shared TPM;

CLIC4, CTSD-30 kDa, CLIC1, PRDX6, PSMA7, and at least two TPM proteins selected from TPM1, TPM2, TPM3, TPM4 or common or shared TPM;

CLIC4, CTSD-30 kDa, CLIC1, PRDX6, BPGM and PSMA7, and at least two TPM proteins selected from TPM1, TPM2, TPM3, TPM4 or common or shared TPM.

Still other permutations of the biomarkers listed herein may form the multiple biomarker targets or an isoform, pro-form, modified molecular form, or peptide fragment thereof in the compositions and methods of this invention. One of skill in the art may readily form appropriate combinations from the biomarkers listed herein, and from any isoform, pro-form, modified molecular form, posttranslational modification, or unique peptide fragment or unique nucleic acid fragment thereof, proteins in the same biomarker family or expressed from a related gene, having at least 20% sequence homology or sequence identity with a specifically named biomarker herein. It is further anticipated that CLIC4 alone, multiple tropomyosins (TPM1, TPM2, TPM3, TPM4 or common or shared TPM) alone, or CLIC4 in concert with multiple tropomyosins may be further combined with other known EOC markers to form desirable target sets.

For example, among desirable biomarker signatures are signatures that comprise, or consist of, at least 2, 3, 4, 5, 6, 7, 8, 9, 10, 15, 20, 25 or more of the biomarkers described herein or any other known ovarian cancer biomarker or molecular forms or peptides thereof. It is contemplated that even higher abundance biomarkers (including some identified in PCT/US12/54136) may be useful when combined in a panel or signature with the low abundance biomarker CLIC4 and/or multiple TPMs.

As further stated above, the biomarkers/biomarker signatures described above, can in another embodiment, refer to nucleic acid sequences, genes and transcripts encoding the biomarkers and expression profiles thereof.

III. Diagnostic Reagents, Devices and Kits

A. Labeled or Immobilized Biomarkers or Peptides or Molecular Forms

Thus, in one aspect, a diagnostic reagent or device comprises the biomarker chloride intracellular channel protein 4 (CLIC4) or an isoform, pro-form, modified molecular form, or unique peptide fragment or nucleic acid fragment thereof. In one embodiment, the biomarker protein or nucleic acid is associated with a molecule or moiety capable alone or in combination with one or more additional molecules of generating a detectable signal. In another embodiment, the biomarker protein or nucleic acid is associated with a substrate and is immobilized.

In another embodiment, a diagnostic reagent or device comprises multiple members of the related family of tropomyosin proteins, such as tropomyosin 1 (TPM1); tropomyosin 2 (TPM2); tropomyosin 3 (TPM3); tropomyosin 4 (TPM4); or a common or shared sequence formed of two or more of these related proteins, or multiple isoforms, pro-forms, modified molecular forms, or unique peptide fragments or nucleic acid fragments thereof. In one embodiment, the biomarker protein or nucleic acid is associated with a molecule or moiety capable alone or in combination with one or more additional molecules of generating a detectable signal. In another embodiment, the biomarker protein or nucleic acid is associated with a substrate and is immobilized.

In another embodiment, a diagnostic reagent or device comprises a CLIC4 and one or multiple members of the related family of tropomyosin proteins, or the TPM common or shared sequence, or multiple isoforms, pro-forms, modified molecular forms, or unique peptide fragments or nucleic acid fragments thereof. In one embodiment, the biomarker proteins or nucleic acid sequences are each associated with a molecule or moiety capable alone or in combination with one or more additional molecules of generating a detectable signal. In another embodiment, the biomarker protein or nucleic acid is associated with a substrate and is immobilized. Where the reagent or device contains multiple biomarker sequences, the detectable moieties and signals can each be different, so as to identify different results.

In still other embodiments, the device or reagent designed to identify CLIC4 and/or multiple TPMs can include additional EOC biomarker proteins, fragments or nucleic acid sequences, such as the disclosed in International Patent Application No. PCT/US12/54136, incorporated by reference herein. Thus, a diagnostic reagent or device as described herein can comprise 1 to 2, 3, 4, 5, 6, 7, 8, 10, 15 or 20 or more biomarker sequences.

In still other embodiments, diagnostic reagents or devices for use in the methods of diagnosing ovarian cancer include CLIC4 and/or multiple TPMs and one or more additional target biomarkers or peptide fragments identified herein, including, but not limited to, isoforms or molecular forms thereof, pro-form, modified molecular form, or unique peptide fragment or nucleic acid fragment thereof, or proteins in the same biomarker family or expressed from a related gene, having at least 20% sequence homology or sequence identity with the identified biomarker.

In still another embodiment of these sets can include one or more additional biomarker that indicates the presence of ovarian cancer in a human subject. In certain embodiments, the additional biomarker is cathepsin D-30 kDa (CTSD-30) or an isoform, pro-form, modified molecular form, or unique peptide fragment or unique nucleic acid fragment thereof, proteins in the same biomarker family or expressed from a related gene, having at least 20% sequence homology or sequence identity with CTSD-30. In other embodiments, the additional biomarker is peroxieredoxin-6 (PRDX6) or an isoform, pro-form, modified molecular form, or unique peptide fragment or unique nucleic acid fragment thereof, or proteins in the same biomarker family or expressed from a related gene, having at least 20% sequence homology or sequence identity with PRDX6. In still other embodiments, the additional biomarker is CA125, or an isoform, pro-form, modified molecular form, or unique peptide fragment therefrom or proteins in the same biomarker family or expressed from a related gene, having at least 20% sequence homology or sequence identity with CA125. In other embodiments, the additional biomarker is bisphosphoglycerate mutase (BPGM) or an isoform, pro-form, modified molecular form, or unique peptide fragment or unique nucleic acid fragment thereof, or proteins in the same biomarker family or expressed from a related gene, having at least 20% sequence homology or sequence identity with BPGM. In other embodiments, the additional biomarker is proteasome subunit alpha type-7 (PSMA7) or an isoform, pro-form, modified molecular form, or unique peptide fragment or unique nucleic acid fragment thereof, or proteins in the same biomarker family or expressed from a related gene, having at least 20% sequence homology or sequence identity with PSMA7. In other embodiments, the additional biomarker is aldose reductase (AKR1B1) or an isoform, pro-form, modified molecular form, or unique peptide fragment or unique nucleic acid fragment thereof, or proteins in the same biomarker family or expressed from a related gene, having at least 20% sequence homology or sequence identity with AKR1B1. In other embodiments, the additional biomarker is homeobox protein (HMX1) or an isoform, pro-form, modified molecular form, or unique peptide fragment or unique nucleic acid fragment thereof, or proteins in the same biomarker family or expressed from a related gene, having at least 20% sequence homology or sequence identity with HMX1. In other embodiments, the additional biomarker is melastatin 1 (TRPM1) or an isoform, pro-form, modified molecular form, or unique peptide fragment or unique nucleic acid fragment thereof, or proteins in the same biomarker family or expressed from a related gene, having at least 20% sequence homology or sequence identity with TRPM1. In other embodiments, the additional biomarker is protein CutA (CUTA) or an isoform, pro-form, modified molecular form, or unique peptide fragment or unique nucleic acid fragment thereof, or proteins in the same biomarker family or expressed from a related gene, having at least 20% sequence homology or sequence identity with CUTA. In other embodiments, the additional biomarker is SERPINB12 protein (SERPINB12), or an isoform, pro-form, modified molecular form, or unique peptide fragment or unique nucleic acid fragment thereof, or proteins in the same biomarker family or expressed from a related gene, having at least 20% sequence homology or sequence identity with SERPINB12. In other embodiments, the additional biomarker is cathepsin D-52 kDa (CTSD-52) or an isoform, pro-form, modified molecular form, or unique peptide fragment or unique nucleic acid fragment thereof, or proteins in the same biomarker family or expressed from a related gene, having at least 20% sequence homology or sequence identity with CTSD-52.

In such embodiments of the diagnostic reagents and devices, at least one of the biomarkers is associated with a detectable label or portion of a detectable label system. In another embodiment, a diagnostic reagent includes one or more target biomarker or peptide fragment identified herein, immobilized on a substrate. In still another embodiment, combinations of such labeled or immobilized biomarkers are suitable reagents and components of a diagnostic kit or device. In another aspect, suitable embodiments of such labeled or immobilized reagents include at least one, 2, 3, 4, 5, 6, 7, 8, 9, 10 or all 20 or more biomarkers identified herein or their unique peptide fragments.

In one aspect the reagent, device or kit as described above further comprises or consists of ligands that individually specifically complex with, bind to, or quantitatively detect or identify multiple isoforms or multiple related proteins of any of biomarkers mentioned herein. In another aspect, the reagent, device or kit comprises or consists of ligands that individually specifically complex with, bind to, or quantitatively detect or identify two or more biomarkers identified in the groups specifically discussed above. Still other diagnostic reagents are the surrogate peptides used for the MRM assays, such as, but not limited to, the peptides disclosed herein.

Any combination of labeled or immobilized biomarkers as described above can be assembled in a diagnostic kit or device for the purposes of diagnosing ovarian cancer, such as those combinations of biomarkers discussed herein.

For these reagents, the labels may be selected from among many known diagnostic labels, including those described above. Similarly, the substrates for immobilization in a device may be any of the common substrates, glass, plastic, a microarray, a microfluidics card, a chip, a bead or a chamber.

B. Labeled or Immobilized Ligands that Bind or Complex with the Biomarkers

In another aspect, a diagnostic reagent or device comprises a ligand capable of specifically complexing with, binding to, or quantitatively detecting or identifying the biomarker chloride intracellular channel protein 4 (CLIC4) or an isoform, pro-form, modified molecular form, or unique peptide fragment or nucleic acid fragment thereof. In one embodiment, the ligand is associated with a molecule or moiety capable alone or in combination with one or more additional molecules of generating a detectable signal. In another embodiment, the ligand is associated with a substrate on which the ligand is immobilized.

In still other embodiments, the diagnostic reagent or device comprises a set of multiple ligands, each ligand individually capable of specifically complexing with, binding to, or quantitatively detecting or identifying a single biomarker or an isoform, pro-form, modified molecular form, or unique peptide fragment or nucleic acid fragment thereof. In another embodiment, a diagnostic reagent or device comprises a ligand capable of specifically complexing with, binding to, or quantitatively detecting or identifying multiple members of the related family of tropomyosin proteins, such as tropomyosin 1 (TPM1); tropomyosin 2 (TPM2); tropomyosin 3 (TPM3); tropomyosin 4 (TPM4); or a common or shared sequence within two or more of these related proteins. In another embodiment, a diagnostic reagent or device comprises multiple ligands, each ligand capable of identifying a different TPM family member.

In another embodiment, a diagnostic reagent or device comprises a ligand capable of specifically complexing with, binding to, or quantitatively detecting or identifying CLIC4 and one or more ligands capable of specifically complexing with, binding to, or quantitatively detecting or identifying individually one or multiple members of the related family of tropomyosin proteins, or the TPM common or shared sequence. In still other embodiments, the device or reagent designed to identify CLIC4 and/or multiple TPMs can contain ligand capable of specifically complexing with, binding to, or quantitatively detecting or identifying other additional EOC biomarkers, such as the unique peptides directed to the above biomarkers and as disclosed in International Patent Application No. PCT/US12/54136, incorporated by reference herein.

Thus, a diagnostic reagent or device as described herein can comprise 1 to 2, 3, 4, 5, 6, 7, 8, 10, 15 or 20 or more such ligands to identify an equivalent number of biomarkers. In still other embodiments, diagnostic reagents or devices for use in the methods of diagnosing ovarian cancer include ligand capable of specifically complexing with, binding to, or quantitatively detecting or identifying CLIC4 and/or multiple TPMs and one or more additional target biomarkers or peptide fragments identified herein, including, but not limited to, isoforms or molecular forms thereof, pro-form, modified molecular form, or unique peptide fragment or nucleic acid fragment thereof, or proteins in the same biomarker family or expressed from a related gene, having at least 20% sequence homology or sequence identity with the identified biomarker.

In still another embodiment, one or more of said ligands in the diagnostic reagent or device is associated with a molecule or moiety capable alone or in combination with one or more additional molecules of generating a detectable signal, a detectable label or portion of a detectable label system. In another embodiment, a diagnostic reagent includes one or more ligand capable of specifically complexing with, binding to, or quantitatively detecting or identifying target biomarker or peptide fragment identified herein, immobilized on a substrate. In still another embodiment, combinations of such labeled or immobilized ligands are suitable reagents and components of a diagnostic kit or device.

In one aspect the reagent, device or kit comprises or consists of ligands that complex with, bind to, or quantitatively detect or identify multiple isoforms or multiple related proteins of any of biomarkers mentioned herein. In another aspect, the reagent, device or kit comprises or consists of ligands that individually specifically complex with, bind to, or quantitatively detect or identify two or more biomarkers in a biomarker family. Still other diagnostic reagents are the ligands to the surrogate peptides used for the MRM assays, such as, but not limited to, the peptides disclosed herein.

Any combination of labeled or immobilized ligands can be assembled in a diagnostic kit or device for the purposes of diagnosing ovarian cancer, such as those combinations of ligands to target biomarker sets discussed herein.

For these reagents, the labels may be selected from among many known diagnostic labels, including those described above. Similarly, the substrates for immobilization in a device may be any of the common substrates, glass, plastic, a microarray, a microfluidics card, a chip, a bead or a chamber.

In another embodiment, the diagnostic reagent or device includes a ligand that binds to or complexes with a biomarker as identified above or a unique peptide thereof, or a molecular form thereof, or a related protein family member expressed by a different, related gene, or a combination of such ligands. In certain aspects, the diagnostic reagent or device includes ligands which can include an antibody or fragment of an antibody, an antibody mimic, a synthetic antibody, a single chain antibody or an equivalent that binds to or complexes with a single biomarker, said ligand optionally associated with a detectable label or with a substrate. Such antibodies may be presently extant in the art or presently used commercially, such as those available as part of commercial antibody sandwich ELISA assay kits or that may be developed by techniques now common in the field of immunology. A recombinant molecule bearing the binding portion of a biomarker antibody, e.g., carrying one or more variable chain CDR sequences that bind e.g., CLIC4, TPM1, TPM2, TPM3, TPM4, PRDX6, CTSD-30, CDSD-52, CLIC1, etc. may also be used in a diagnostic assay. As used herein, the term "antibody" may also refer, where appropriate, to a mixture of different antibodies or antibody fragments that bind to the selected biomarker. Such different antibodies may bind to different biomarkers or different portions of the same biomarker protein than the other antibodies in the mixture. Such differences in antibodies used in the assay may be reflected in the CDR sequences of the variable regions of the antibodies. Such differences may also be generated by the antibody backbone, for example, if the antibody itself is a non-human antibody containing a human CDR sequence, or a chimeric antibody or some other recombinant antibody fragment containing sequences from a non-human source. Antibodies or fragments useful in the compositions or methods described herein may be generated synthetically or recombinantly, using conventional techniques or may be isolated and purified from plasma or further manipulated to increase the binding affinity thereof. It should be understood that any antibody, antibody fragment, or mixture thereof that binds one of the biomarkers described herein or a particular sequence of the selected biomarker or peptide fragment thereof may be employed in the compositions and methods, regardless of how the antibody or mixture of antibodies was generated. Various forms of antibody, e.g., polyclonal, monoclonal, recombinant, chimeric, as well as fragments and components (e.g., CDRs, single chain variable regions, etc.) or antibody mimics or equivalents may be used in place of antibodies. The ligand itself may be labeled or immobilized.

In another embodiment, the reagent ligands are nucleotide sequences, the diagnostic reagent is a polynucleotide or oligonucleotide sequence that hybridizes to gene, gene fragment, gene transcript or nucleotide sequence encoding a biomarker discussed herein or encoding a unique peptide thereof. Such a polynucleotide/oligonucleotide can be a probe or primer, and may itself be labeled or immobilized. In one embodiment, ligand-hybridizing polynucleotide or oligonucleotide reagent(s) are part of a primer-probe set, and the kit comprises both primer and probe. Each said primer-probe set amplifies a different gene, gene fragment or gene expression product that encodes a different biomarker discussed herein, optionally including one or more additional known biomarkers, also as described above. For use in the compositions the PCR primers and probes are preferably designed based upon intron sequences present in the biomarker gene(s) to be amplified selected from the gene expression profile. The design of the primer and probe sequences is within the skill of the art once the particular gene target is selected. The particular methods selected for the primer and probe design and the particular primer and probe sequences are not limiting features of these compositions. A ready explanation of primer and probe design techniques available to those of skill in the art is summarized in U.S. Pat. No. 7,081,340, with reference to publically available tools such as DNA BLAST software, the Repeat Masker program (Baylor College of Medicine), Primer Express (Applied Biosystems); MGB assay-by-design (Applied Biosystems); Primer3 (Steve Rozen and Helen J. Skaletsky (2000) Primer3 on the WWW for general users and for biologist programmers and other publications.

In general, optimal PCR primers and probes used in the compositions described herein are generally 17-30 bases in length, and contain about 20-80%, such as, for example, about 50-60% G+C bases. Melting temperatures of between 50 and 80° C., e.g. about 50 to 70° C. are typically preferred.

In one embodiment, such a ligand binding to a protein biomarker or a unique peptide contained therein, can be an antibody which specifically binds a single biomarker such as CLIC4, or a unique peptide in that single biomarker or a nucleic acid sequence which hybridizes to the nucleic acid sequence encoding CLIC4 or its unique peptide. In one embodiment, such a ligand desirably binds to a protein biomarker or a unique peptide contained therein, and can be an antibody which specifically binds to one or more of the TPM family members, e.g., TPM1, 2, 3, or 4 individually, collectively, or individually to a unique peptide in that single TPM biomarker, or to a TPM common or shared biomarker. In another embodiment, such a ligand can hybridize to the nucleic acid sequence encoding the protein biomarker or a unique peptide contained therein, where the biomarker is one or more of the TPM family members, e.g., TPM1, 2, 3, or 4 individually, collectively, or individually to a nucleic acid encoding a unique peptide in that single TPM biomarker, or to a TPM common or shared biomarker.

In another embodiment, suitable labeled or immobilized reagents include at least 2, 3, 4, 5, 6, 7 8, 9, 10 or 11 or more ligands or antibodies, in which each ligand binds to or complexes with a single biomarker protein/peptide, fragment, or molecular form of the biomarker(s) listed in detail above. In some of the embodiments in which the combination of biomarkers including those listed specifically above or another known additional biomarker that may be in higher abundance in serum, ligands to each of these additional biomarkers may be employed in the diagnostic reagent.

Any combination of labeled or immobilized biomarker ligands can be assembled in a diagnostic kit or device for the purposes of diagnosing ovarian cancer.

Thus, a kit or device can contain multiple reagents or one or more individual reagents. For example, one embodiment of a composition includes a substrate upon which the biomarkers or ligands are immobilized. In another embodiment, the kit also contains optional detectable labels, immobilization substrates, optional substrates for enzymatic labels, as well as other laboratory items.

The diagnostic reagents, devices, or kits compositions based on the biomarkers or fragments described herein or including the ligands thereto, optionally associated with detectable labels, can be presented in the format of a microfluidics card, a chip or chamber, a bead or a kit adapted for use with assays formats such as sandwich ELISAs, multiple protein assays, platform multiplex ELISAs, such as the BioRad Luminex platform, mass spectrometry quantitative assays, or PCR, RT-PCR or Q PCR techniques.

The selection of the ligands, biomarker sequences, their length, suitable labels and substrates used in the reagents and kits are routine determinations made by one of skill in the art in view of the teachings herein of which biomarkers form signatures suitable for the diagnosis of ovarian cancer. Assembly of the ligands and biomarkers discussed herein, attachment to a substrate, and assembly into the form of a microarray, a microfluidics card, a chip, a bead, or a chamber employ techniques known in the art.

IV. Methods for Diagnosing or Monitoring Ovarian Cancer

In another embodiment, a method for diagnosing or detecting or monitoring the progress of ovarian cancer and treatment of ovarian cancer in a subject comprises, or consists of, a variety of steps.

A. Sample Preparation

The test sample is obtained from a human subject who is to undergo the treatment or is in the process of being treated. The subject's sample can in one embodiment be provided before initial diagnosis, so that the method is performed to diagnose the existence of an ovarian cancer. In another embodiment, depending upon the reference standard and markers used, the method is performed to diagnosis the stage of ovarian cancer. In another embodiment, depending upon the reference standard and markers used, the method is performed to diagnosis the type or subtype of ovarian cancer from the types and subtypes identified above. In another embodiment, the subject's sample can be provided after a diagnosis, so that the method is performed to monitor progression of an ovarian cancer. In another embodiment, the sample can be provided prior to surgical removal of an ovarian tumor or prior to therapeutic treatment of a diagnosed ovarian cancer and the method used to thereafter monitor the effect of the treatment or surgery, and to check for relapse. In another embodiment, the sample can be provided following surgical removal of an ovarian tumor or following therapeutic treatment of a diagnosed ovarian cancer, and the method performed to ascertain efficacy of treatment or relapse. In yet another embodiment the sample may be obtained from the subject periodically during therapeutic treatment for an ovarian cancer, and the method employed to track efficacy of therapy or relapse. In yet another embodiment the sample may be obtained from the subject periodically during therapeutic treatment to enable the physician to change therapies or adjust dosages. In one or more of these embodiments, the subject's own prior sample can be employed in the method as the reference standard.

Preferably where the sample is a fluid, e.g., blood, serum or plasma, obtaining the sample involves simply withdrawing and preparing the sample in traditional fashion for contact with the diagnostic reagent. Where the sample is a tissue or tumor sample, it may be prepared in conventional manner for contact with the diagnostic reagent.

The method further involves contacting the sample obtained from a test subject with a diagnostic reagent as described above under conditions that permit the reagent to bind to or complex with one or more biomarker(s), e.g., CLIC4 and/or multiple TPM biomarkers, and/or additional biomarkers which may be present in the sample. This method may employ any of the suitable diagnostic reagents or kits or compositions described above.

B. Measuring Biomarker Levels

Thereafter, a suitable assay is employed to detect or measure in the sample the protein level (actual or relative) of one or more biomarker(s), including CLIC4 and/or multiple TPMs, and/or additional biomarkers discussed herein. Alternatively, a suitable assay is employed to generate a protein abundance profile (actual or relative or ratios thereof) of multiple biomarkers discussed herein from the sample or of multiple different molecular forms of the same biomarker or both. In another embodiment, the above method further includes measuring in the biological sample of the subject the protein level of one or more additional biomarkers, such as CTSD-30 kDa, CA125 or other known ovarian cancer biomarker identified herein or other known EOC biomarker known in the art.

In another embodiment, the above method further includes measuring in the biological sample of the subject the protein levels of two or more additional biomarkers which form with CLIC4 and/or multiple or common or shared TPMs, a biomarker protein abundance signature for ovarian cancer. In one embodiment, the measurement of all target biomarkers occurs in a single sample. In another embodiment, the measurement of all target biomarkers occurs in a multiple samples from a single patient. It should be understood that the measurement of all biomarkers need not occur simultaneously or in the same assay. Results from multiple assays may be combined providing that they are performed within a reasonable time for comparison with the other target biomarker levels.

The measurement of the biomarker(s) in the biological sample may employ any suitable ligand, e.g., antibody, antibody mimic or equivalent (or antibody to any second biomarker) to detect the biomarker protein, as described above. Similarly, the antibodies may be tagged or labeled with reagents capable of providing a detectable signal, depending upon the assay format employed. Such labels are capable, alone or in concert with other compositions or compounds, of providing a detectable signal. Where more than one antibody is employed in a diagnostic method for a single biomarker, e.g., such as in a sandwich ELISA, the labels are desirably interactive to produce a detectable signal. Most desirably, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength.

Other label systems that may be utilized in the methods and devices of this invention are detectable by other means, e.g., colored latex microparticles (Bangs Laboratories, Indiana) in which a dye is embedded may be used in place of enzymes to provide a visual signal indicative of the presence of the resulting selected biomarker-antibody complex in applicable assays. Still other labels include fluorescent compounds, radioactive compounds or elements. Preferably, an anti-biomarker antibody is associated with, or conjugated to a fluorescent detectable fluorochromes, e.g., fluorescein isothiocyanate (FITC), phycoerythrin (PE), allophycocyanin (APC), coriphosphine-O (CPO) or tandem dyes, PE-cyanin-5 (PC5), and PE-Texas Red (ECD). Commonly used fluorochromes include fluorescein isothiocyanate (FITC), phycoerythrin (PE), allophycocyanin (APC), and also include the tandem dyes, PE-cyanin-5 (PC5), PE-cyanin-7 (PC7), PE-cyanin-5.5, PE-Texas Red (ECD), rhodamine, PerCP, fluorescein isothiocyanate (FITC) and Alexa dyes. Combinations of such labels, such as Texas Red and rhodamine, FITC+PE, FITC+PECy5 and PE+PECy7, among others may be used depending upon assay method.

Detectable labels for attachment to antibodies useful in diagnostic assays and devices of this invention may be easily selected from among numerous compositions known and readily available to one skilled in the art of diagnostic assays. The biomarker-antibodies or fragments useful in this invention are not limited by the particular detectable label or label system employed. Thus, selection and/or generation of suitable biomarker antibodies with optional labels for use in this invention is within the skill of the art, provided with this specification, the documents incorporated herein, and the conventional teachings of immunology.

Similarly the particular assay format used to measure the selected biomarker in a biological sample may be selected from among a wide range of protein assays, such as described in the examples below. Suitable assays include enzyme-linked immunoassays, sandwich immunoassays, homogeneous assays, immunohistochemistry formats, or other conventional assay formats. In one embodiment, a serum/plasma sandwich ELISA is employed in the method. In another embodiment, a mass spectrometry-based assay is employed. In another embodiment, a MRM assay is employed, in which antibodies are used to enrich the biomarker in a manner analogous to the capture antibody in sandwich ELISAs. One of skill in the art may readily select from any number of conventional immunoassay formats to perform this invention.

Other reagents for the detection of protein in biological samples, such as peptide mimetics, synthetic chemical compounds capable of detecting the selected biomarker may be used in other assay formats for the quantitative detection of biomarker protein in biological samples, such as high pressure liquid chromatography (HPLC), immunohistochemistry, etc.

Employing ligand binding to the biomarker proteins or multiple biomarkers forming the signature enables more precise quantitative assays, as illustrated by the multiple reaction monitoring (MRM) mass spectrometry (MS) assays. As an alternative to specific peptide-based MRM-MS assays that can distinguish specific protein isoforms and proteolytic fragments, the knowledge of specific molecular forms of biomarkers allows more accurate antibody-based assays, such as sandwich ELISA assays or their equivalent. Frequently, the isoform specificity, protein domain specificity and affects of posttranslational modifications on binding of immune reagents used in pre-clinical (and some clinical) diagnostic tests are not well defined. MRM-MS assays were used to quantitative the levels of a number of the low abundance biomarkers in samples, as discussed in the examples.

In one embodiment, suitable assays for use in these methods include immunoassays using antibodies or ligands to the above-identified biomarkers and biomarker signatures. In another embodiment, a suitable assay includes a multiplexed MRM based assay for two more biomarkers that include one or more of the proteins/unique peptides described herein. It is anticipated that ultimately the platform most likely to be used in clinical assays will be multi-plexed or parallel sandwich ELISA assays or their equivalent, primarily because this platform is the technology most commonly used to quantify blood proteins in clinical laboratories. MRM MS assays may continue to be used productively to help evaluate the isoform/molecular form specificity of any existing immunoassays or those developed in the future. In addition, multiplexed quantitative MS assays such as MRM MS may replace ELISA assays in clinical laboratories in some situations.

C. Detection of a Change in Biomarker Abundance Level and Diagnosis

The protein level of the one or more biomarker(s) in the subject's sample or the protein abundance profile of multiple said biomarkers as detected by the use of the assays described above is then compared with the level of the same biomarker or biomarkers in a reference standard or reference profile. In one embodiment, the comparing step of the method is performed by a computer processor or computerprogrammed instrument that generates numerical or graphical data useful in the appropriate diagnosis of the condition. Optionally, the comparison may be performed manually.

The detection or observation of a change in the protein level of a biomarker or biomarkers in the subject's sample from the same biomarker or biomarkers in the reference standard can indicate an appropriate diagnosis. An appropriate diagnosis can be identifying a risk of developing ovarian cancer, a diagnosis of ovarian cancer (or stage or type thereof), a diagnosis or detection of the status of progression or remission of ovarian cancer in the subject following therapy or surgery, a determination of the need for a change in therapy or dosage of therapeutic agent. The method is thus useful for early diagnosis of disease, for monitoring response or relapse after initial diagnosis and treatment or to predict clinical outcome or determine the best clinical treatment for the subject.

In one embodiment, the change in protein level of each biomarker can involve an increase of a biomarker or multiple biomarkers in comparison to the specific reference standard. In one embodiment, the biomarker CLIC4 is increased in a subject sample from a patient having ovarian cancer when compared to the levels of these biomarkers from a healthy reference standard. In another embodiment, the biomarkers are increased in a subject sample from a patient having ovarian cancer prior to therapy or surgery, when compared to the levels of these biomarkers from a post-surgery or post-therapy reference standard.

In another embodiment, the change in protein level of each biomarker can involve a decrease of a biomarker or multiple biomarkers in comparison to the specific reference standard. In one embodiment, the biomarkers are decreased in a subject sample from a patient having ovarian cancer following surgical removal of a tumor or following chemotherapy/radiation when compared to the levels of these biomarkers from a pre-surgery/pre-therapy ovarian cancer reference standard or a reference standard which is a sample obtained from the same subject pre-surgery or pre-therapy.

In still other embodiments, the changes in protein levels of the biomarkers may be altered in characteristic ways if the reference standard is a particular type of ovarian cancer, e.g., serous, epithelial, mucinous or clear cell, or if the reference standard is derived from benign ovarian cysts or nodules.

The results of the methods and use of the compositions described herein may be used in conjunction with clinical risk factors to help physicians make more accurate decisions about how to manage patients with ovarian cancers. Another advantage of these methods and compositions is that diagnosis may occur earlier than with more invasive diagnostic measures.

D. Alternative Assay Embodiments

In an alternative embodiment, the method of diagnosis or risk of diagnosis involves using the nucleic acid hybridizing reagent ligands described above to detect a significant change in expression level of the subject's sample biomarker or biomarkers from that in a reference standard or reference expression profile which indicates a diagnosis, risk, or the status of progression or remission of ovarian cancer in the subject. These methods may be performed in other biological samples, e.g., biopsy tissue samples, tissue removed by surgery, or tumor cell samples, including circulating tumor cells isolated from the blood, to detect or analyze a risk of developing an ovarian cancer, as well as a diagnosis of same. Such methods are also known in the art and include contacting a sample obtained from a test subject with a diagnostic reagent comprising a ligand which is a nucleotide sequence capable of hybridizing to a nucleic acid sequence encoding a biomarker or biomarker combination described herein, e.g., CLIC4 and/or multiple TPM proteins, said ligand associated with a detectable label or with a substrate. Thereafter one would detect or measure in the sample or from an expression profile generated from the sample, the expression levels of one or more of the biomarkers or ratios thereof. The expression level(s) of the biomarker(s) in the subject's sample or from an expression profile or ratio of multiple said biomarkers are then compared with the expression level of the same biomarker or biomarkers in a reference standard. A significant change in expression level of the subject's sample biomarker or biomarkers from that in the reference standard indicates a diagnosis, risk, or the status of progression or remission of ovarian cancer in the subject.

Suitable assay methods include methods based on hybridization analysis of polynucleotides, methods based on sequencing of polynucleotides, proteomics-based methods or immunochemistry techniques. The most commonly used methods known in the art for the quantification of mRNA expression in a sample include northern blotting and in situ hybridization; RNAse protection assays; and PCR-based methods, such as reverse transcription polymerase chain reaction (RT-PCR) or qPCR. Alternatively, antibodies may be employed that can recognize specific DNA-protein duplexes. The methods described herein are not limited by the particular techniques selected to perform them. Exemplary commercial products for generation of reagents or performance of assays include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test), the MassARRAY-based method (Sequenom, Inc., San Diego, Calif.), differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) and high coverage expression profiling (HiCEP) analysis.

The comparison of the quantitative or relative expression levels of the biomarkers may be done analogously to that described above for the comparison of protein levels of biomarkers.

E. Non-Ligand-Based Analysis

In another aspect, a method for diagnosing or detecting or monitoring the progress of ovarian cancer in a subject involves non-ligand based methods, such as mass spectrometry. For example, proteins in a biological sample obtained from a test subject may be contacted with a chemical or enzymatic agent and the proteins, including the biomarkers contained therein fragmented in the sample. The digested sample or portions thereof are injected into a mass spectrometer and the protein levels or ratios of one or more of the biomarker or biomarker combinations described herein, optionally with other known biomarkers, modified molecular forms, peptides and unique peptides or ratios thereof, are quantitatively identified or measured by mass spectrometry. The protein levels of the biomarkers in the subject's sample are then compared with the level of the same biomarker or biomarkers in a reference standard or to a predetermined cutoff derived from the reference standard. In one embodiment, the agent is a proteolytic enzyme. In another embodiment, the agent is trypsin.

A significant change in protein level of the subject's sample biomarker or biomarkers from that in the reference standard or from a predetermined cutoff indicates a diagnosis, risk, or the status of progression or remission of ovarian cancer in the subject.

Thus, the various methods, devices and steps described above can be utilized in an initial diagnosis of ovarian cancer or other ovarian condition, as well as in clinical management of patients with ovarian cancer after initial diagnosis. Uses in clinical management of the various devices, reagents and assay methods, include without limitation, monitoring for reoccurrence of disease or monitoring remission or progression of the cancer and either before, during or after therapeutic or surgical intervention, selecting among therapeutic protocols for individual patients, monitoring for development of toxicity or other complications of therapy, and predicting development of therapeutic resistance.

In one embodiment, the method involves enriching the biomarker protein or one or more peptides produced by specific proteolysis in the sample by contacting the sample with an antibody prior to injecting into a mass spectrometer in a manner analogous to a capture antibody in a conventional sandwich ELISA. In another embodiment, the method involves depleting the sample of non-target proteins prior to injecting sample into a mass spectrometer. The depletion may also be performed using antibodies to the non-targets. The method described herein may use liquid chromatographic mass spectrometry, such as HPLC. One such method is described in detail in the Examples below.

F. Illustrative Embodiments

In one embodiment, a method for diagnosing or detecting or monitoring the progress of ovarian cancer in a subject comprises contacting a sample obtained from a test subject with a diagnostic reagent or device comprising a ligand capable of specifically complexing with, binding to, or quantitatively detecting or identifying the biomarker chloride intracellular channel protein 4 (CLIC4) or an isoform, pro-form, modified molecular form, or unique peptide fragment or nucleic acid fragment thereof. Thereafter, the method involves detecting or measuring in the sample or from a protein level profile generated from the sample, the protein levels of the CLIC4 biomarker. Another step includes comparing the protein levels of the CLIC4 biomarker in the subject's with the level of the same biomarker in a reference standard. A significant change in protein level of the subject's sample from that in the reference standard indicates a diagnosis, risk, or the status of progression or remission of ovarian cancer in the subject.

In another aspect, the method comprises detecting or measuring in the sample or from a protein level profile generated from the sample, the protein levels of one or more additional ovarian cancer biomarkers; and comparing the protein levels of the CLIC4 biomarker in relation to the levels of the additional biomarkers in the subject's sample with the same biomarkers in a reference standard or profile.

In another aspect, the method uses as a reference standard a mean, an average, a numerical mean or range of numerical means, a numerical pattern, a ratio, a graphical pattern or a protein level profile derived from the same biomarker or biomarkers in a reference subject or reference population. In certain embodiments, the change in protein level of each biomarker comprises an increase in comparison to said reference or control or a decrease in comparison to said reference or control.

Use of such methods permits early diagnosis of disease, monitoring relapse after initial diagnosis and treatment, predicting clinical outcome, or determining the best clinical treatment.

IV. Examples

As discussed in detail in the examples below, it was discovered that a single member of the chloride intracellular channel proteins, CLIC4, which is expressed from a related but different gene than CLIC1, was readily and with great sensitivity, detectable in ovarian cancer patient sera. In additional aspects, related tropomyosin proteins expressed from a gene other than the gene expressing TPM1 and its isoforms, were also detectable in ovarian cancer patent sera. A multiplexed, label-free multiple reaction monitoring (MRM) assay was established to target peptides specific to the detected CLIC and TPM biomarkers, and were quantitated for ovarian cancer patients, patients with benign disease, and normal donors. In addition to CLIC1 and TPM1, which were biomarker proteins discovered in a xenograft mouse model (see PCT/US12/54136, cited above), CLIC4, TPM2, TPM3, and TPM4 were present in ovarian cancer patient sera at significantly elevated levels compared with controls. These additional biomarkers may be superior to the previously identified biomarkers at discriminating between cancer and noncancer patients.

The invention is now described with reference to the following examples. These examples are provided for the purpose of illustration only and the invention should in no way be construed as being limited to these examples but rather should be construed to encompass any and all variations that become evident as a result of the teaching provided herein.

Example 1

Materials and Methods

A. Human Serum Collection and Processing

Sera from patients with benign ovarian tumors and from late-stage ovarian cancer patients were collected at the University of Turin, Turin, Italy, at the time of diagnosis and have been previously described (Tang et al, 2012, cited above). Control serum samples were collected from healthy, post-menopausal female donors at The Wistar Institute, Philadelphia, Pa. All specimens were processed in compliance with Institutional Review Board (IRB) and Health Insurance Portability and Accountability Act (HIPAA) requirements. Control and patient serum samples were processed for MS analysis either individually or as pools, as previously described.[21] Dithiothreitol (DTT) was obtained from GE Healthcare (Piscataway, N.J.); and iodoacetamide from Sigma-Aldrich (St. Louis, Mo.).

B. LC-MS/MS of Patient Sample Pools

To identify all CLIC and TPM isoforms that could be detected in ovarian cancer patient sera, label-free comparisons of pooled sera were performed. One pool of serum from benign patients and three pools of advanced ovarian cancer patient serum samples were made. Serum pools were immunodepleted, separated on a 1D SDS gel for 4 cm, sliced into 40 fractions, and digested with trypsin (sequencing-grade, modified trypsin from Promega, Madison, Wis.) as described in Tang et al, 2012, cited above and incorporated herein by reference). Tryptic digests were analyzed using an LTQ Orbitrap XL mass spectrometer (Thermo Scientific, Waltham, Mass.) connected to a NanoACQUITY UPLC system (Waters, Milford, Mass.). Peptides were eluted at 200 nL/min using a 229 min gradient consisting of 5-28% B over 168 min, 28-50% B over 51.5 min, 50-80% B over 5 min, 80% B for 4.5 min, before returning to 5% B over 0.5 min. A short blank gradient was run before injecting the next sample. The mass spectrometer was set to scan m/z from 400 to 2000. The full MS scan was collected at 60,000 resolution in the Orbitrap in profile mode followed by data-dependent MS/MS scans on the six-most-abundant ions exceeding a minimum threshold of 1000, collected in the linear trap.

Monoisotopic precursor selection was enabled and charge-state screening was enabled to reject z=1 ions. Ions subjected to MS/MS were excluded from repeated analysis for 60 s.

C. Data Processing

MS/MS spectra were extracted and searched using the SEQUEST algorithm (v. 28, rev. 13, University of Washington, Seattle, Wash.) in Bioworks (v. 3.3.1, Thermo Scientific) against the human UniRef100 protein sequence database (v. June 2011) plus common contaminants A decoy database was produced by reversing the protein sequence of each database entry, and the entire reversed database was appended in front of the forward database. Spectra were searched with a partial tryptic constraint with up to two missed cleavages, 100 ppm precursor mass tolerance, 1 Da fragment ion mass tolerance, static modification of Cys (+57.0215 Da), and variable modification of Methionine (+15.9949 Da). Common or shared protein lists were created using DTASelect (v. 2.0, licensed from Scripps Research Institute, La Jolla, Calif.).

The following filters were applied: remove proteins that are subsets of others, full tryptic constraint, a minimum of two peptides, mass accuracy ≤10 ppm, and $\Delta Cn \geq 0.05$ (Wang, H et al., *J Proteome Res* 2011, 10, (11), 4993-5005). The peptide false discovery rate in the resulting dataset was less than 1%. Quantitative comparisons of all detected CLIC and TPM (related proteins from different genes and isoforms of a single gene) across serum pools were performed using Rosetta Elucidator software to compare peptide signal intensities in full MS scans. Retention time alignment, feature identification (discrete ion signals), feature extraction, and protein identifications were performed by the Elucidator system as previously described in Tang et al, 2012, Tang, et al, 2011; and Beer et al, 2011, all cited above.

D. Label-free MRM Analysis

MRM experiments were performed on a 5500 QTRAP hybrid triple quadrupole/linear ion trap mass spectrometer (AB SCIEX, Foster City, Calif.) interfaced with a NanoAC-QUITY UPLC system. Eight µL of tryptic digests were injected using the partial loop injection mode onto a UPLC Symmetry trap column (180 µm i.d.×2 cm packed with 5 µm C18 resin; Waters) and then separated by RP-HPLC on a BEH C18 nanocapillary analytical column (75 µm i.d.×25 cm, 1.7 µm particle size; Waters) at 45° C. Chromatography was performed with Solvent A, which contained Milli-Q water with 0.1% formic acid, and Solvent B, which contained HPLC-grade acetonitrile (Thomas Scientific, Swedesboro, N.J.) and 0.1% formic acid. Peptides were eluted at 400 nL/min for 5-35% B over 24 min, 35% B for 3 min before returning to 5% B in 0.5 min.

To minimize sample carryover, a fast blank gradient was run between each sample. An identical reference sample was run at the beginning of each set of samples and was used to normalize variation in MRM signals caused by changes in performance of the HPLC, reverse phase column or mass spectrometer. MRM data were acquired with a spray voltage of 3300 V, curtain gas of 20 p.s.i., nebulizer gas of 10 p.s.i., interface heater temperature of 150° C., and a pause time of 3 ms. Multiple MRM transitions were monitored using unit resolution in both Q1 and Q3 quadrupoles to maximize specificity. Scheduled MRM was used to reduce the number of concurrent transitions and maximize the dwell time for each transition. The detection window was set at 3 min, and the target scan time was set at 1.8 s. Data analyses were performed using MultiQuant version 2.1 software (AB SCIEX). The most abundant transition for each peptide was used for quantitation unless interference from the matrix was observed. In these cases, another transition free of interference was chosen for quantitation.

E. Statistical Analyses

Serum levels of candidate biomarkers were compared across patient groups using the Mann-Whitney test, and Bonferroni-adjusted P-values were reported in scatter plots. Results were considered statistically significant if the Bonferroni-adjusted P-value of the test was less than 0.05. Spearman's correlation coefficients were calculated to examine correlations among all tested tropomyosin peptides. For each candidate biomarker, a receiver operator characteristic (ROC) curve was generated and the area under the curve was calculated to reflect biomarker specific potential sensitivity and specificity for distinguishing non-cancer and cancer patients.

Example 2

Ambiguities in Identification of EOC Candidate Biomarkers and Isoforms from Analysis of Xenograft Mouse Serum We previously identified 106 human proteins with at least two peptides from the serum of a xenograft mouse model of human ovarian endometrioid cancer (TOV-112D tumors) using a gel based, multidimensional protein profiling strategy.[21] In that study, GeLC-MRM quantitation of several candidate biomarkers in the 20-55 kDa region showed that CLIC1, PRDX6, and the mature form of CTSD were significantly elevated in ovarian cancer patients compared with noncancer (normal and benign disease) individuals.

Tropomyosin 1 (TPM1) isoform 6 was initially identified as a human protein in the xenograft mouse serum based upon the detection of two human-specific peptides and four peptides common to human and mouse. Changes of species specificity due to database updates was not a widespread problem, because reexamination of the species specificity of our previously identified putative human peptides revealed that only seven peptides (approximately 1%) were identical to new mouse entries in the 2011 database. Since both human and mouse TPM1 are also highly homologous (98 to 99% identical, depending on specific isoforms used for comparison), it is extremely challenging to distinguish between the two species.

The confident identification of specific biomarkers proteins within proteins families is often ambiguous when using shotgun proteomics, because protease digestion destroys the connectivity between proteins and detected peptides. Inferring the correct peptide-protein association is often confounded by the presence of shared peptides from homologous proteins that are not isoforms from the same gene, alternative splice variants, or redundant database entries (Nesvizhskii, A. I.; Aebersold, R., *Mol Cell Proteomics* 2005, 4, (10), 1419-40). But for MRM quantitation, it is important to accurately determine the peptide-protein relationship to ensure the correct form of a protein is being quantitated.

In order to determine all potential peptide-protein associations for the observed TPM peptides, each peptide identified in the xenograft mouse was searched against the human UniProtKB database (February, 2012) using the BLAST algorithm. All database entries containing the peptide sequence were identified and redundant entries were manually removed. When available, gene names associated with each database entry were also extracted (see Table 2).

TABLE 2

Peptides identified in TOV-112D xenograft mouse serum and human serum pools

| Sequence[a] | SEQ ID NO | # Unique Database Entries | Gene |
|---|---|---|---|
| TPM1 Peptides Identified in Xenograft Mouse Serum | | | |
| ETAEADVASLN[b] | aa43-53 of SEQ ID NO. 6 | 6 | TPM1 |
| SLQEQADAAEER[b] | aa16-27 of SEQ ID NO. 10 | 7 | TPM1 |
| (K)LVIIESDLER[b], | aa132-142 of SEQ ID NO: 10 | 18 | TPM1 |
| MEIQEIQLK | aa105-113 of SEQ ID NO. 6 | 38 | TPM1, TPM3 |
| IQLVEEELDR[b], | aa43-53 of SEQ ID NO. 6 | 43 | TPM1, TPM2, TPM3, TPM4 |
| TPM1 Peptides Detected in Patient Serum Pools | | | |
| ETAEADVASLNR[b] | aa43-54 of SEQ ID NO. 6 | 6 | TPM1 |
| SLQEQADAAEER[b], | aa16-27 of SEQ ID NO. 10 | 7 | TPM1 |
| (K)LVIIESDLER[b] | aa132-142 of SEQ ID NO. 6 | 18 | TPM1 |
| MEIQEIQLK | aa105-113 of SEQ ID NO. 6 | 38 | TPM1, TPM3 |
| (R)IQLVEEELDR[b] | aa55-65 of SEQ ID NO. 6 | 43 | TPM1, TPM2, TPM3, TPM4 |
| AELSEGQVR[b] | aa147-155 of SEQ ID NO: 10 | 10 | TPM1 |
| YEEEIK[c] | aa185-190 of SEQ ID NO. 6 | 57 | TPM1, TPM2, TPM3, TPM4 |
| ATDAEADVASLNR[c,d] | 17 | 19 | TPM1, TPM2 |
| TPM2 Peptides Detected in Patient Serum Pools | | | |
| (K)LVILEGELER[b] | 18 | 11 | TPM2, TPM4 |
| (R)IQLVEEELDR[b] | aa55-65 of SEQ ID NO: 10 | 43 | TPM1, TPM2, TPM3, TPM4 |
| ATDAEADVASLNR[c] | 17 | 19 | TPM1, TPM2 |
| MELQEMQLK | 20 | 8 | TPM2 |
| SLMASEEEYSTK | 21 | 3 | TPM2 |
| YEEEIK[c], | aa185-190 of SEQ ID NO. 6 | 57 | TPM1, TPM2, TPM3, TPM4 |
| EDKYEEEIK | 22 | 31 | TPM2, TPM3, TPM4 |
| CGDLEEELK[c] | 23 | 6 | TPM2, TPM4 |
| TPM3 Peptides Detected in Patient Serum Pools | | | |
| (K)IQVLQQQADDAEER[b] | 24 | 16 | TPM3 |
| (R)IQLVEEELDR[b], | aa55-65 of SEQ ID NO: 10 | 43 | TPM1, TPM2, TPM3, TPM4 |
| MELQEIQLK | 25 | 38 | TPM1, TPM3 |
| (K)LVIIEGDLER | 26 | 19 | TPM3 |
| HIAEEADR | 27 | 22 | TPM3, TPM4 |
| MLDQTLLDLNEM | 28 | 12 | TPM3 |
| YEEEIK[c], | aa185-190 of SEQ ID NO. 6 | 57 | TPM1, TPM2, TPM3, TPM4 |
| EDKYEEEIK | 22 | 31 | TPM2, TPM3, |

TABLE 2-continued

Peptides identified in TOV-112D
xenograft mouse serum and human serum pools

| Sequence[a] | SEQ ID NO | # Unique Database Entries | Gene |
|---|---|---|---|
| | | | TPM4 |
| CLSAAEEK | 29 | 14 | TPM3 |
| AADAEAEVASLNR | 30 | 1 | TPM3 |
| TPM4 Peptides Detected in Patient Serum Pools | | | |
| (K)IQALQQQADEAEDR[b] | 31 | 3 | TPM4 |
| (K)LVILEGELER[b] | 18 | 11 | TPM2, TPM4 |
| EENVGLHQTLDQTLNELNCI | 32 | 4 | TPM4 |
| AEGDVAALNR[b] | 13 | 4 | TPM4 |
| MEIQEMQLK | 33 | 2 | TPM4 |
| YSEKEDKYEEEIK | 34 | 4 | TPM4 |
| CGDLEEELK[c] | 23 | 6 | TPM2, TPM4 |
| (R)IQLVEEELDR[b], | aa55-65 of SEQ ID NO: 10 | 43 | TPM1, TPM2, TPM3, TPM4 |
| HIAEEADR | 27 | 22 | TPM3, TPM4 |
| EKAEGDVAALNR | 35 | 3 | TPM4 |
| YEEEIK[c], | aa185-190 of SEQ ID NO. 6 | 57 | TPM1, TPM2, TPM3, TPM4 |
| EDKYEEEIK | 22 | 31 | TPM2, TPM3, TPM4 |
| TIDDLEEK | 36 | 4 | TPM4 |
| ASDAEGDVAALNR | 37 | 1 | TPM4 |

NOTES
[a]Detected peptides shared by multiple gene products are listed under all matching proteins. Underlined sequences were identified as human in the UniProtKB 2007 database, but also matched a mouse homolog in a later database
[b]Peptide targeted for MRM. Successful quantitation.
[c]Peptide targeted for MRM. Unsuccessful quantitation.
[d]This peptide is not present in the group of TPM1 isoforms (FIG. 3) defined by peptides identified from the xenograft mouse serum.

These peptides, i.e., KLVIIESDLE, aa132-142 of SEQ ID NO: 10, LVIIESDLER, aa133-142 of SEQ ID NO: 10; M*EIQEIQLK, aa105-113 of SEQ ID NO. 6; ETAEADVASLNR, aa43-54 of SEQ ID NO. 6; IQLVEEELDR, aa 43-53 of SEQ ID NO:6; and SLQEQADAAEER, aa16-27 of SEQ ID NO: 10, show a great degree of ambiguity in peptide-protein association due to the large number of TPM family members and the number of known isoforms of several of the family members. Tropomyosin is encoded by four genes (TPM1 to TPM4), and each gene can further generate multiple isoforms by the use of alternative promoters and/or alternative RNA splicing. More than 40 distinct TPM family proteins and isoforms have been reported in vertebrates (Gunning, P. W et al, *Trends Cell Biol* 2005, 15, (6), 333-41; Choi, C et al., *J Struct Biol* 2012, 177, (1), 63-9). The TPM1 peptides identified from the xenograft model were initially assigned to TPM1 isoform 6 (Q7Z6L8) using the parsimony principle to explain all the identified peptides. While BLAST indicates TPM1 is present, the exact TPM1 isoform cannot be ascertained, and the presence of the related proteins, TPM2, TPM3, or TPM4 or the isoforms thereof, cannot be excluded and should be considered.

Example 3

Biomarker Proteins Detectable in Patient Serum Pools that Correlate with EOC

A. Tropomyosin Family Biomarkers

The tropomyosins are a family of actin filament-binding proteins that have a well-defined central role in regulating muscle contraction and cytoskeletal organization in non-muscle cells. Decreased expression of specific tropomyosin isoforms is commonly associated with the transformed phenotype and has been reported for cancer cells and tissues, including EOC (Helfman, D. M. et al, *Adv Exp Med Biol* 2008, 644, 124-31; Raval, G. N. et al, *Oncogene* 2003, 22, (40), 6194-203 and Chow, S. N et al, *Eur J Gynaecol Oncol* 2010, 31, (1), 55-62). The serological level of tropomyosin is not well studied, although high plasma levels of TPM4 have been associated with asbestos exposure, and increased levels of tropomyosin serum antibodies were observed in colorectal cancer patients.

To determine which TPM family protein or isoform is/are detectable in ovarian cancer patient serum, we used an ovarian patient serum protein dataset from in-depth GeLC-MS/MS analysis of the 20-55 kDa region of one benign and three different late-stage ovarian cancer patient immunoaffinity depleted serum pools.

In the case of TPM1, one new TPM1-specific peptide and two shared peptides were discovered in the patient serum in addition to previously identified TPM1 isoform peptides from the xenograft mouse serum (See FIG. 3, Table 1 and Table 3). Table 3 shows high confidence biomarker proteins/peptides detected in patient sera.

TABLE 3

(Part 1)

| # | Uniprot ID | Name | Description | Seq. Count | Spectrum Count |
|---|---|---|---|---|---|
| 1 | O00299 | CLIC1 | Chloride intracellular channel protein 1 | 12 | 67 |
| 1a | Q53FB0 | CLIC1 | Chloride intracellular channel 1 variant | 12 | 67 |
| 2 | Q9Y696 | CLIC4 | Chloride intracellular channel protein 4 | 10 | 24 |
| 3a | Q1ZYL5 | TPM1 | Tropomyosin 1 alpha variant 6 | 9 | 94 |
| 3b | B7Z596 | | cDNA FLJ55130, highly similar to Rattus norvegicus tropomyosin 1, alpha (Tpm1), transcript variant 8, mRNA | 9 | 94 |
| 4a | UR1H_P07951 | TPM2 | Tropomyosin beta chain | 9 | 125 |
| 4b | UR1H_Q5TCU3 | TPM2 | Tropomyosin 2 (beta) | 9 | 125 |
| 4c | UR1H_Q5TCU8 | TPM2 | Tropomyosin 2 (beta) | 9 | 125 |
| 5a | P07951-2 | TPM2 | Isoform 2 of Tropomyosin beta chain | 9 | 107 |
| 5b | A7XZE4 | TPM2 | Beta Troppomyosin isoform | 9 | 107 |
| 6 | P06753 | TPM3 | Tropomyosin alpha-3 chain | 9 | 77 |
| 7a | Q5VU59 | TPM3 | Tropomyosin-3 | 12 | 112 |
| 7b | Q5HYB6 | TPM3 | DKFZp686J1372 | 12 | 112 |
| 7c | B2RDE1 | TPM3 | cDNA, FLJ96568 | 12 | 112 |
| 7d | E2RB38 | TPM3 | Uncharacterized protein | 12 | 112 |
| 8 | P67936 | TPM4 | Tropomyosin alpha-4 chain | 16 | 243 |
| 9 | P67936-2 | TPM4 | Isoform 2 of Tropomyosin alpha-4 chain | 13 | 149 |

(Part 2)

| # | Seq Coverage | MolWt | pI | ObsM+H+ | Ppm | z | XCorr | DeltCN | SpR |
|---|---|---|---|---|---|---|---|---|---|
| 1 | 67.7 | 26923 | 5.2 | 1932.9794 | 3.1 | 2 | 4.4164 | 0.4663 | 1 |
| 1a | 67.7 | 27015 | 5.2 | 1281.67 | 1.3 | 2 | 4.0828 | 0.3965 | 1 |
| | | | | 1844.9752 | 0 | 2 | 4.3773 | 0.5176 | 1 |
| | | | | 2992.3948 | 1.4 | 3 | 5.7564 | 0.546 | 1 |
| | | | | 1328.6461 | 1.6 | 2 | 3.3785 | 0.4031 | 1 |
| | | | | 1095.6344 | 0.2 | 2 | 2.4544 | 0.1432 | 1 |
| | | | | 1065.6228 | 5.9 | 2 | 2.3876 | 0.0719 | 1 |
| | | | | 2573.1345 | 4.3 | 2 | 3.7106 | 0.3711 | 1 |
| | | | | 2061.072 | 1.7 | 3 | 3.2149 | 0.2172 | 2 |
| | | | | 1572.8121 | 2 | 2 | 2.8708 | 0.1944 | 1 |
| | | | | 1078.5076 | -2.1 | 2 | 2.2701 | 0.16 | 6 |
| | | | | 957.4788 | -0.1 | 2 | 2.0529 | 0.062 | 13 |

TABLE 3-continued

| | | | | | | | | | |
|---|---|---|---|---|---|---|---|---|---|
| 2 | 52.6 | 28772 | 5.6 | 1264.7158 | 0.9 | 2 | 3.8998 | 0.3919 | 1 |
| | | | | 2595.1702 | 1.8 | 3 | 4.4279 | 0.3832 | 1 |
| | | | | 1385.6783 | 1.1 | 3 | 3.8417 | 0.2936 | 1 |
| | | | | 1223.6191 | 3.1 | 2 | 3.0191 | 0.2578 | 1 |
| | | | | 1079.6346 | 2.3 | 2 | 2.66 | 0.1121 | 1 |
| | | | | 1313.5336 | 1.7 | 2 | 2.695 | 0.2585 | 1 |
| | | | | 1602.8118 | 2.2 | 2 | 2.3922 | 0.2966 | 1 |
| | | | | 1966.9231 | −0.9 | 2 | 2.6045 | 0.239 | 1 |
| | | | | 1588.8486 | 1.1 | 3 | 2.2303 | 0.1033 | 81 |
| | | | | 1533.7018 | 1 | 2 | 1.9489 | 0.0741 | 34 |
| 3a | 28.6 | 28509 | 4.8 | 1243.6528 | 0 | 2 | 3.6574 | 0.283 | 1 |
| 3b | 25.5 | 31753 | 4.9 | 1346.6198 | 1.1 | 2 | 3.8906 | 0.3488 | 1 |
| | | | | 1186.6775 | 8.3 | 2 | 2.8985 | 0.1839 | 1 |
| | | | | 1147.6036 | 0.8 | 2 | 3.3535 | 0.1265 | 1 |
| | | | | 1275.6222 | 3.7 | 2 | 3.696 | 0.3306 | 1 |
| | | | | 1314.7639 | 0.9 | 3 | 3.8858 | 0.3198 | 1 |
| | | | | 988.5064 | 0.6 | 2 | 2.6379 | 0.1755 | 1 |
| | | | | 1399.7528 | −0.9 | 3 | 3.3619 | 0.2539 | 11 |
| | | | | 810.3899 | 2.3 | 2 | 1.8363 | 0.0982 | 13 |
| 4a | 21.8 | 32851 | 4.7 | 1298.7697 | 1.4 | 3 | 4.5416 | 0.2826 | 1 |
| 4b | 21.8 | 32815 | 4.7 | 1170.6774 | 3.9 | 2 | 3.6614 | 0.2594 | 1 |
| 4c | 19.3 | 36747 | 4.8 | 1243.6528 | 0 | 2 | 3.6574 | 0.283 | 1 |
| | | | | 1332.6372 | −1.3 | 2 | 3.5477 | 0.261 | 1 |
| | | | | 1181.5554 | 1.2 | 2 | 2.9144 | 0.1323 | 3 |
| | | | | 1092.4814 | −5.8 | 2 | 3.0957 | 0.1527 | 2 |
| | | | | 1399.7528 | −0.9 | 3 | 3.3619 | 0.2539 | 11 |
| | | | | 810.3899 | 2.3 | 2 | 1.8363 | 0.0982 | 13 |
| | | | | 1182.5557 | 2.7 | 2 | 2.3489 | 0.1214 | 35 |
| 5a | 22.9 | 32990 | 4.7 | 1298.7697 | 1.4 | 3 | 4.5416 | 0.2826 | 1 |
| 5b | 22.9 | 33026 | 4.7 | 1170.6774 | 3.9 | 2 | 3.6614 | 0.2594 | 1 |
| | | | | 1243.6528 | 0 | 2 | 3.6574 | 0.283 | 1 |
| | | | | 1332.6372 | −1.3 | 2 | 3.5477 | 0.261 | 1 |
| | | | | 1181.5554 | 1.2 | 2 | 2.9144 | 0.1323 | 3 |
| | | | | 1399.7528 | −0.9 | 3 | 3.3619 | 0.2539 | 11 |
| | | | | 1390.6013 | −2.1 | 2 | 2.326 | 0.3071 | 1 |
| | | | | 810.3899 | 2.3 | 2 | 1.8363 | 0.0982 | 13 |
| | | | | 1182.5557 | 2.7 | 2 | 2.3489 | 0.1214 | 35 |
| 6 | 21.5 | 32819 | 4.7 | 1243.6528 | 0 | 2 | 3.6574 | 0.283 | 1 |
| | | | | 1147.6036 | 0.8 | 2 | 3.3535 | 0.1265 | 1 |
| | | | | 1284.7534 | 0.9 | 3 | 3.5549 | 0.2933 | 1 |
| | | | | 1156.6655 | 7.2 | 2 | 3.2166 | 0.1613 | 2 |
| | | | | 1399.7528 | −0.9 | 3 | 3.3619 | 0.2539 | 11 |
| | | | | 940.4491 | 0.8 | 2 | 2.3445 | 0.1573 | 1 |
| | | | | 1316.6499 | 4.4 | 3 | 3.194 | 0.0726 | 2 |
| | | | | 810.3899 | 2.3 | 2 | 1.8363 | 0.0982 | 13 |
| | | | | 1182.5557 | 2.7 | 2 | 2.3489 | 0.1214 | 35 |
| 7a | 35.8 | 27175 | 4.8 | 1642.8102 | 4.3 | 2 | 5.1395 | 0.4843 | 1 |
| 7b | 35.8 | 27176 | 4.7 | 1770.897 | −0.6 | 3 | 4.6197 | 0.4128 | 1 |
| 7c | 33.5 | 29018 | 4.8 | 1243.6528 | 0 | 2 | 3.6574 | 0.283 | 1 |
| 7d | 33.5 | 29033 | 4.8 | 1147.6036 | 0.8 | 2 | 3.3535 | 0.1265 | 1 |
| | | | | 1284.7534 | 0.9 | 3 | 3.5549 | 0.2933 | 1 |
| | | | | 1156.6655 | 7.2 | 2 | 3.2166 | 0.1613 | 2 |
| | | | | 1399.7528 | −0.9 | 3 | 3.3619 | 0.2539 | 11 |
| | | | | 940.4491 | 0.8 | 2 | 2.3445 | 0.1573 | 1 |
| | | | | 1467.6772 | 4.6 | 2 | 2.864 | 0.2482 | 2 |
| | | | | 810.3899 | 2.3 | 2 | 1.8363 | 0.0982 | 13 |
| | | | | 1182.5557 | 2.7 | 2 | 2.3489 | 0.1214 | 35 |
| | | | | 907.4202 | 1.4 | 2 | 1.7519 | 0.0886 | 33 |
| 8 | 46.8 | 28522 | 4.7 | 1614.7726 | 0.5 | 2 | 4.8416 | 0.5205 | 1 |
| | | | | 1742.8723 | 3.2 | 3 | 5.3142 | 0.4742 | 1 |
| | | | | 1298.7697 | 1.4 | 3 | 4.5416 | 0.2826 | 1 |
| | | | | 2340.1206 | 3 | 2 | 5.717 | 0.2539 | 1 |
| | | | | 1170.6774 | 3.9 | 2 | 3.6614 | 0.2594 | 1 |
| | | | | 1243.6528 | 0 | 2 | 3.6574 | 0.283 | 1 |
| | | | | 1015.5159 | −0.8 | 2 | 3.1643 | 0.3492 | 1 |
| | | | | 1181.5554 | 1.2 | 2 | 2.9144 | 0.1323 | 3 |
| | | | | 1689.7849 | −0.3 | 3 | 3.9281 | 0.2333 | 1 |

TABLE 3-continued

|  |  |  |  | 1092.4814 | -5.8 | 2 | 3.0957 | 0.1527 | 2 |
|---|---|---|---|---|---|---|---|---|---|
|  |  |  |  | 1399.7528 | -0.9 | 3 | 3.3619 | 0.2539 | 11 |
|  |  |  |  | 940.4491 | 0.8 | 2 | 2.3445 | 0.1573 | 1 |
|  |  |  |  | 1272.659 | 3.7 | 3 | 3.0739 | 0.2454 | 11 |
|  |  |  |  | 810.3899 | 2.3 | 2 | 1.8363 | 0.0982 | 13 |
|  |  |  |  | 1182.5557 | 2.7 | 2 | 2.3489 | 0.1214 | 35 |
|  |  |  |  | 962.4657 | -2.1 | 2 | 1.5493 | 0.0793 | 90 |
| 9 | 35.9 | 32723 | 4.7 | 1298.7697 | 1.4 | 3 | 4.5416 | 0.2826 | 1 |
|  |  |  |  | 2340.1206 | 3 | 2 | 5.717 | 0.2539 | 1 |
|  |  |  |  | 1170.6774 | 3.9 | 2 | 3.6614 | 0.2594 | 1 |
|  |  |  |  | 1243.6528 | 0 | 2 | 3.6574 | 0.283 | 1 |
|  |  |  |  | 1181.5554 | 1.2 | 2 | 2.9144 | 0.1323 | 3 |
|  |  |  |  | 1689.7849 | -0.3 | 3 | 3.9281 | 0.2333 | 1 |
|  |  |  |  | 1092.4814 | -5.8 | 2 | 3.0957 | 0.1527 | 2 |
|  |  |  |  | 1399.7528 | -0.9 | 3 | 3.3619 | 0.2539 | 11 |
|  |  |  |  | 1288.6102 | -1.9 | 2 | 2.8922 | 0.1827 | 1 |
|  |  |  |  | 940.4491 | 0.8 | 2 | 2.3445 | 0.1573 | 1 |
|  |  |  |  | 810.3899 | 2.3 | 2 | 1.8363 | 0.0982 | 13 |
|  |  |  |  | 1182.5557 | 2.7 | 2 | 2.3489 | 0.1214 | 35 |
|  |  |  |  | 962.4657 | -2.1 | 2 | 1.5493 | 0.0793 | 90 |

(Part 3)

| No | Sequence[b] | SEQ ID NO. |
|---|---|---|
| 1a | K.FLDGNELTLADCNLLPK.L | 38 |
| 1b | K.GVTFNVTTVDTK.R | 39 |
|  | K.LAALNPESNTAGLDIFAK.F | 40 |
|  | K.VLDNYLTSPLPEEVDETSAEDEGVSQR.K | 41 |
|  | K.NSNPALNDNLEK.G | 42 |
|  | K.LHIVQVVCK.K | 43 |
|  | R.LFM*VLWLK.G | 44 |
|  | R.EEFASTCPDDEEIELAYEQVAK.A | 45 |
|  | R.KFLDGNELTLADCNLLPK.L | 46 |
|  | K.IEEFLEAVLCPPR.Y | 47 |
|  | K.IGNCPFSQR.L | 48 |
|  | R.YLSNAYAR.E | 49 |
| 2 | KGVVFSVTTVDLK.R | aa48-61 of SEQ ID NO: 1 |
|  | K.LDEYLNSPLPDEIDENSM*EDIK.F | aa150-173 of SEQ ID NO: 1 |
|  | K.NSRPEANEALER.G | aa130-143 of SEQ ID NO: 1 |
|  | K.EVEIAYSDVAK.R | aa237-250 of SEQ ID NO: 1 |
|  | R.LFM*ILWLK.G[c] | aa40-49 of SEQ ID NO: 1 |
|  | R.DEFTNTCPSDK.E | aa227-239 of SEQ ID NO: 1 |
|  | K.IEEFLEEVLCPPK.Y | aa90-104 of SEQ ID NO: 1 |
|  | K.FLDGNEM*TLADCNLLPK.L | aa177-195 of SEQ ID NO: 1 |
|  | K.EEDKEPLIELFVK.A | aa11-25 of SEQ ID NO: 1 |
|  | K.HPESNTAGM*DIFAK.F | aa110-125 of SEQ ID NO: 1 |
| 3a | R.IQLVEEELDR.A | 50 |
| 3b | R.SLQEQADAAEER.A | aa15-28 of SEQ ID NO: 10 |
|  | K.LVIIESDLER.A | aa132-143 of SEQ ID NO: 10 |
|  | K.M*EIQEIQLK.E | aa104-114 of SEQ ID NO: 6 |
|  | R.ETAEADVASLNR.R | aa42-55 of SEQ ID NO: 6 |
|  | R.KLVIIESDLER.A | aa131-143 of SEQ ID NO: 10 |
|  | R.AELSEGQVR.Q | aa147-156 of SEQ ID NO: 10 |
|  | R.RIQLVEEELDR.A | 51 |
|  | R.YEEEIK.V | aa184-191 of SEQ ID NO: 6 |
| 4a | R.KLVILEGELER.S | 19 |
| 4b | K.LVILEGELER.S | 52 |
| 4c | R.IQLVEEELDR.A | 50 |
|  | K.ATDAEADVASLNR.R | 53 |
|  | K.M*ELQEM*QLK.E | 54 |
|  | K.CGDLEEELK.I | 55 |
|  | R.RIQLVEEELDR.A | 51 |
|  | K.YEEEIK.L | 56 |
|  | K.EDKYEEEIK.L | 58 |
| 5a | R.KLVILEGELER.S | 19 |
| 5b | K.LVILEGELER.S | 52 |
|  | R.IQLVEEELDR.A | 50 |
|  | K.ATDAEADVASLNR.R | 53 |
|  | K.M*ELQEM*QLK.E | 54 |

TABLE 3-continued

|   |   |   |
|---|---|---|
|   | R.RIQLVEEELDR.A | 51 |
|   | K.SLM*ASEEEYSTK.E | 57 |
|   | K.YEEEIK.L | 56 |
|   | K.EDKYEEEIK.L | 58 |
| 6 | R.IQLVEEELDR.A | 50 |
|   | KM*ELQEIQLK.E | 59 |
|   | R.KLVIIEGDLER.T | 60 |
|   | K.LVIIEGDLER.T | 61 |
|   | R.RIQLVEEELDR.A | 51 |
|   | K.HIAEEADR.K | 62 |
|   | K.AADAEAEVASLNR.R | 63 |
|   | K.YEEEIK.I | 64 |
|   | K.EDKYEEEIK.I | 65 |
| 7a | KIQVLQQQADDAEERA | 66 |
| 7b | RKIQVLQQQADDAEER.A | 67 |
| 7c | RIQLVEEELDR.A | 50 |
| 7d | KM*ELQEIQLKE | 68 |
|   | RKLVIIEGDLERT | 60 |
|   | K.LVIIEGDLER.T | 61 |
|   | RRIQLVEEELDRA | 50 |
|   | KHIAEEADRK | 62 |
|   | RM*LDQTLLDLNEM* | 69 |
|   | KYEEEIKI | 64 |
|   | K.EDKYEEEIK.I | 65 |
|   | KCLSAAEEKY | 70 |
| 8 | K.IQALQQQADEAEDRA | 71 |
|   | RKIQALQQQADEAEDR.A | 72 |
|   | RKLVILEGELERA | 73 |
|   | KEENVGLHQTLDQTLNELNCL | 74 |
|   | KLVILEGELERA | aa2-13 of SEQ ID NO: 73 |
|   | RIQLVEEELDRA | aa2-14 of SEQ ID NO: 50 |
|   | KAEGDVAALNR.R | aa3-14 of SEQ ID NO: 75 |
|   | K.M*EIQEM*QLK.E | 76 |
|   | K.YSEKEDKYEEEIK.L | 77 |
|   | K.CGDLEEELKN | 78 |
|   | R.RIQLVEEELDRA | 50 |
|   | K.HIAEEADRK | 62 |
|   | REKAEGDVAALNR.R | 75 |
|   | K.YEEEIK.L | 56 |
|   | K.EDKYEEEIK.L | 58 |
|   | K.TIDDLEEK.L | 79 |
| 9 | RKLVILEGELERA | 73 |
|   | KEENVGLHQTLDQTLNELNCL | 74 |
|   | K.LVILEGELER.A | aa2-13 of SEQ ID NO: 73 |
|   | R.IQLVEEELDR.A | 50 |
|   | K.M*EIQEM*QLK.E | 76 |
|   | K.YSEKEDKYEEEIK.L | 77 |
|   | K.CGDLEEELKN | 78 |
|   | R.RIQLVEEELDR.A | 51 |
|   | KASDAEGDVAALNR.R | 80 |
|   | K.HIAEEADR.K | 62 |
|   | K.YEEEIK.L | 56 |
|   | K.EDKYEEEIK.L | 58 |
|   | K.TIDDLEEK.L | 79 |

[a]All peptides mapping to listed protein isoforms are shown, i.e., peptides shared by multiple protein isoforms are listed for each of these multiple proteins.
[b]Different forms of the same peptide (charge states and methionine oxidation) were collapsed and displayed as a single peptide. M* indicates methionine oxidation.
[c]This peptide is also present in CLIC2, CLIC5, and CLIC6.

Based on the newly identified AELSEGQVR, AA147-155 of SEQ ID NO: 10, peptide, all observed peptides were contained within two TPM1 isoforms, TPM1 variant 6 (Q1ZYL5) or B7Z596. These two sequences share 80% identity and differ from each other at the C-terminus. Distinguishing between these isoforms was not feasible in this study due to the inability to detect any isoform-specific C-terminal peptides. Although no other TPM1 isoforms or TPM family members were conclusively identified in human serum, their presence cannot be ruled out. But the failure to detect any unique peptides to other TPM family members or TPM1 isoforms suggests they are either not present or are present in much lower abundance in human serum.

The TPM family proteins and/or their isoforms identified in the patient sera were quantitated by summing MS intensities for all peptides unique to a specific gene product (see FIGS. 1A through 1D). There was evidence of protein products for all four TPM genes and the expressed related gene products showed elevated levels in EOC.

B. Chloride Ion Channel Protein Biomarkers

Figure 1A:
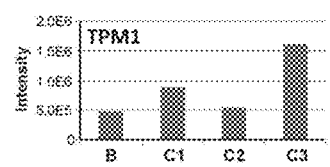
FIG. 1A is a quantitation of the biomarker tropomyosin 1 (TPM1) extracted from an LC-MS chromatogram using label-free discovery mode, and GeLC-MS/MS analysis of patient serum pools. Intensities of identified peptides unique to this biomarker were summed for each of four serum pools (B—benign disease; C1, C2, C3—three different advanced ovarian cancer pools. LC-MS data from corresponding gel fractions of different serum pools were aligned and quantitatively compared using Elucidator software.
Figure 1B:
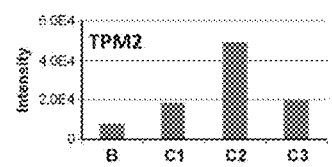
FIG. 1B is a quantitation as described in FIG. 1A for the biomarker tropomyosin 2 (TPM2), expressed from a different gene than that expressing TPM1.
Figure 1C:
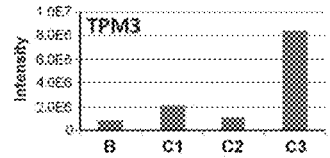
FIG. 1C is a quantitation as described in FIG. 1A for the biomarker tropomyosin 3 (TPM3), expressed from a different gene than that expressing TPM1.
Figure 1D:
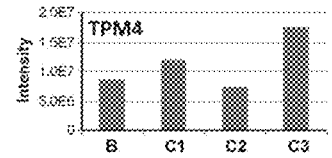
FIG. 1D is a quantitation as described in FIG. 1A for the biomarker tropomyosin 4 (TPM4), expressed from a different gene than that expressing TPM1.
Figure 1E:
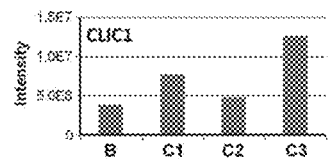
FIG. 1E is a quantitation as described in FIG. 1A for the biomarker chloride ion channel protein 1 (CLIC1).
Figure 1F:
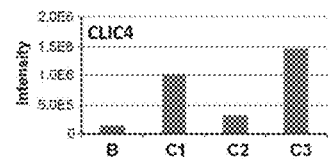
FIG. 1F is a quantitation as described in FIG. 1A for the biomarker chloride ion channel protein 4 (CLIC4) expressed from a different gene than that expressing CLIC1.
Figure 4A:
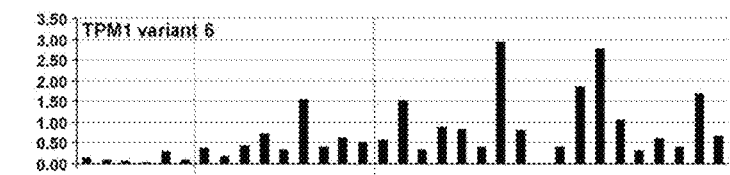
FIGS. 4A-4D are GeLC-MRM quantitations of tropomyosin biomarkers in individuals without ovarian cancer (WCS), individuals with benign (B), and individuals with late-stage (T) ovarian cancer. The following peptides were used to derive these values.
Figure 4B:
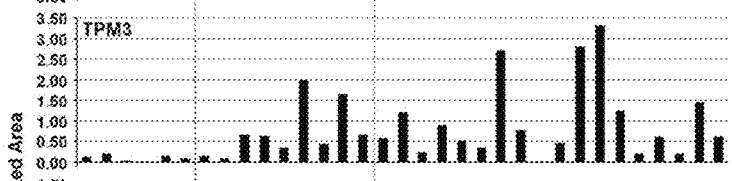
Figure 4C:
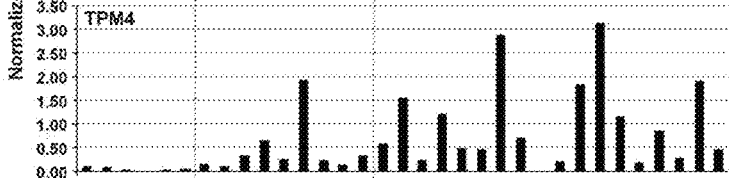
Figure 4D:
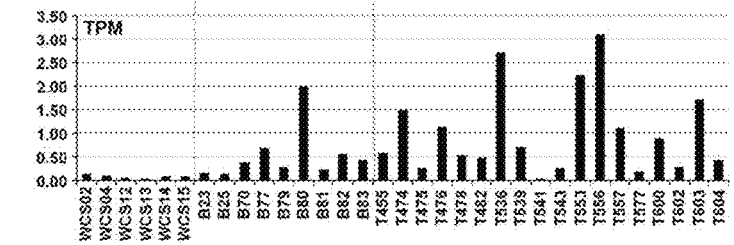

Two CLIC family proteins were identified in the patient sera and were quantitated by summing MS intensities for all peptides unique to a specific gene product (see FIGS. 1E and 1F). The previously identified CLIC1 was confirmed to be both detected and elevated in ovarian cancer patient serum compared to benign disease.

Another CLIC family member protein CLIC4 was newly identified in the ovarian cancer patient sera. CLIC4 is a multifunctional protein that has been shown to be highly expressed in ovarian cancer stroma and may play an important role in cancer development (Yao, Q et al., *Oncol Rep* 2009, 22, (3), 541-8; Shukla, A.; Yuspa, S. H., *Nucleus* 2010, 1, (2), 144-9). CLIC4 was detected by nine specific peptides and showed elevated levels in ovarian cancer patient sera, suggesting that it was an EOC biomarker. The observation of CLIC4 in ovarian cancer patient sera raised the question as to why human CLIC1 had been previously identified in the xenograft mouse serum, but CLIC4 had not been detected.

Examination of this data showed that CLIC4 was identified by four peptides, all peptides identical to mouse sequences, i.e., K.GVVFSVTTVDLK.R, aa48-61 of SEQ ID NO: 1; K.HPESNTAGM*DIFAK.F, aa110-125 of SEQ ID NO: 1; K.LDEYLNSPLPDEIDENSM*EDIK.F, aa150-173 of SEQ ID NO: 1; and R.KPADLQNLAPGTHPPFITF-NSEVK.T, aa61-86 of SEQ ID NO: 1. This is not surprising, as the human and mouse CLIC4 sequences are 99% identical (See FIG. 2A and Table 4). While distinguishing between mouse and human CLIC4 is very difficult, this problem is limited to the xenograft mouse model. In contrast, distinguishing the different CLIC family proteins, e.g., gene products, in human serum is more straightforward, as the sequence homologies of the four CLIC genes with similar molecular weights are somewhat lower. Specifically, the two CLIC family proteins detected, CLIC1 and CLIC4, share 67% identity. Hence, most CLIC peptides observed in the xenograft mouse serum and in patient serum pools were unique to either CLIC1 or CLIC4 (see FIG. 2B).

Example 4

Development of MRM Assays for Quantitation of CLIC4 and TPM Isoforms

CLIC and TPM biomarker protein levels in individual serum samples that included control serum samples (six normal and nine benign) and late-stage cancer samples (15 Stage III and 3 Stage IV) were determined using GeLC-MRM, essentially as previously described in Tang et al 2012, cited above. Peptides were selected based on their isoform specificity and signal intensity in MRM analysis using a 5500 QTRAP mass spectrometer. Peptide candidates for MRM were derived from a combination of the LCMS/MS analyses reported above and all human plasma/serum LC-MS/MS proteomic analyses that had been performed in this laboratory.

In the case of CLIC4, selection of MRM peptides was relatively straightforward because no major isoform issues were encountered with the identified peptides (FIG. 2B). Inclusion of peptides identified from other serum proteome analyses allowed selection of peptides with the strongest MRM signal. For example, the CLIC4 peptide, YLT-NAYSR, aa220-227 of SEQ ID NO: 1, was found to produce a stronger MRM signal than some of the peptides discovered in this analysis and was therefore used for MRM quantitation (See Tables 4 and 5). Table 4 shows MRM peak areas for CLIC4 peptides, which have been normalized and averaged in individual samples as an indication of the protein abundance level.

TABLE 4

| Sample | # | CLIC4 NSRPEANEALER, aa 131-142 of SEQ ID NO: 1 | CLIC4 YLTNAYSR aa220-227 of SEQ ID NO: 1 | CLIC4 EVEIAYSDVAK, aa 139-249 of SEQ ID NO: 1 | CLIC4 Norm & Avg |
|---|---|---|---|---|---|
| Normal | WCS02 | 71938 | 75784 | 5917 | 0.171 |
| Normal | WCS04 | 71504 | 94424 | 13193 | 0.214 |
| Normal | WCS12 | 58303 | 67969 | 5269 | 0.146 |
| Normal | WCS13 | 92896 | 92885 | 21819 | 0.268 |
| Normal | WCS14 | 133409 | 130748 | 38618 | 0.410 |
| Normal | WCSI5 | 90830 | 100865 | 28662 | 0.298 |
| Benign | B23 | 106848 | 144779 | 28506 | 0.355 |
| Benign | B25 | 93943 | 128049 | 23848 | 0.308 |
| Benign | B70 | 142389 | 164356 | 28363 | 0.412 |
| Benign | B77 | 180776 | 242906 | 75215 | 0.699 |
| Benign | B79 | 121455 | 162778 | 39150 | 0.427 |
| Benign | B80 | 233045 | 287533 | 87063 | 0.841 |
| Benign | B81 | 125616 | 150244 | 36499 | 0.411 |
| Benign | B82 | 162386 | 269199 | 41618 | 0.578 |
| Benign | B83 | 120162 | 217288 | 50882 | 0.518 |
| Cancer | T455 | 361477 | 343172 | 106250 | 1.106 |
| Cancer | T474 | 444226 | 449309 | 98203 | 1.264 |

TABLE 4-continued

| Sample | # | CLIC4 NSRPEANEALER, aa 131-142 of SEQ ID NO: 1 | CLIC4 YLTNAYSR aa220-227 of SEQ ID NO: 1 | CLIC4 EVEIAYSDVAK, aa 139-249 of SEQ ID NO: 1 | CLIC4 Norm & Avg |
|---|---|---|---|---|---|
| Cancer | T475 | 205961 | 249565 | 36565 | 0.590 |
| Cancer | T476 | 120474 | 170584 | 22532 | 0.371 |
| Cancer | T478 | 236002 | 254455 | 93543 | 0.839 |
| Cancer | T482 | 380003 | 516406 | 80345 | 1.187 |
| Cancer | T536 | 443069 | 340463 | 308048 | 1.942 |
| Cancer | T539 | 249682 | 306233 | 49728 | 0.739 |
| Cancer | T541 | 87267 | 113303 | 17938 | 0.266 |
| Cancer | T543 | 107946 | 206527 | 44406 | 0.471 |
| Cancer | T553 | 415869 | 618499 | 114770 | 1.446 |
| Cancer | T556 | 959630 | 1244493 | 256878 | 3.143 |
| Cancer | T557 | 266741 | 378642 | 60233 | 0.862 |
| Cancer | T577 | 176341 | 183183 | 41724 | 0.516 |
| Cancer | T600 | 360817 | 393236 | 87364 | 1.080 |
| Cancer | T602 | 167445 | 266095 | 68203 | 0.679 |
| Cancer | T603 | 257545 | 473664 | 89399 | 1.045 |
| Cancer | T604 | 114903 | 174142 | 46015 | 0.455 |
| Cancer | T455 | 361477 | 343172 | 106250 | 1.106 |

TABLE 5 shows MRM peak areas for CLIC1 peptides normalized and averaged in individual samples as an indication of the protein abundance level.

| Sample | # | CLIC1 GVTFNVTTVDTK, aa38-49 of SEQ ID NO: 3 | CLIC1 LAALNPESNT AGLDIFAK, aa96-113 of SEQ ID NO: 3 | CLIC1 NSNPALNDNLEK, aa120-131 of SEQ ID NO: 3 | CLIC1 Norm & Avg |
|---|---|---|---|---|---|
| Normal | WCS02 | 112466 | 46620 | 67000 | 0.099 |
| Normal | WCS04 | 201327 | 82090 | 148050 | 0.190 |
| Normal | WCS12 | 33884 | 30160 | 51100 | 0.054 |
| Normal | WCS13 | 28858 | 32810 | 30770 | 0.044 |
| Normal | WCS14 | 164134 | 155000 | 173700 | 0.230 |
| Normal | WCS15 | 104943 | 85700 | 87400 | 0.128 |
| Benign | B23 | 143772 | 113800 | 131900 | 0.179 |
| Benign | B25 | 105300 | 27596 | 58447 | 0.082 |
| Benign | B70 | 210921 | 194300 | 220300 | 0.313 |
| Benign | B77 | 680255 | 387400 | 491200 | 0.704 |
| Benign | B79 | 452783 | 340500 | 393500 | 0.544 |
| Benign | B80 | 754653 | 168561 | 528925 | 0.623 |
| Benign | B81 | 168894 | 56262 | 137171 | 0.159 |

TABLE 5-continued shows MRM peak areas for CLIC1 peptides normalized and averaged in individual samples as an indication of the protein abundance level.

| Sample | # | CLIC1 GVTFNVTTVDTK, aa38-49 of SEQ ID NO: 3 | CLIC1 LAALNPESNT AGLDIFAK, aa96-113 of SEQ ID NO: 3 | CLIC1 NSNPALNDNLEK, aa120-131 of SEQ ID NO: 3 | CLIC1 Norm & Avg |
|---|---|---|---|---|---|
| Benign | B82 | 1367992 | 623771 | 1039990 | 1.347 |
| Benign | B83 | 549811 | 153388 | 395116 | 0.476 |
| Cancer | T455 | 980711 | 546125 | 697954 | 0.999 |
| Cancer | T474 | 819310 | 351580 | 518150 | 0.745 |
| Cancer | T475 | 286624 | 205100 | 204300 | 0.318 |
| Cancer | T476 | 414920 | 306150 | 290460 | 0.463 |
| Cancer | T478 | 485804 | 298830 | 183150 | 0.435 |
| Cancer | T482 | 2816690 | 2008424 | 2505141 | 3.373 |
| Cancer | T536 | 1178896 | 964000 | 1143310 | 1.516 |
| Cancer | T539 | 651564 | 398980 | 428100 | 0.667 |
| Cancer | T541 | 49917 | 27680 | 36000 | 0.051 |
| Cancer | T543 | 511810 | 232600 | 314500 | 0.469 |
| Cancer | T553 | 1993369 | 1119800 | 1503310 | 2.076 |
| Cancer | T556 | 2808408 | 2207100 | 2532200 | 3.472 |
| Cancer | T557 | 651252 | 444800 | 440800 | 0.699 |
| Cancer | T577 | 346698 | 214500 | 277400 | 0.380 |
| Cancer | T600 | 567452 | 358500 | 471000 | 0.633 |
| Cancer | T602 | 455781 | 280500 | 317400 | 0.476 |
| Cancer | T603 | 771899 | 505560 | 620200 | 0.862 |
| Cancer | T604 | 280053 | 204600 | 316300 | 0.367 |

Selecting appropriate peptides for MRM quantitation of TPM1 isoforms and TPM family proteins in general, and TPM1 specifically, was more complicated due to the large number of TPM family members and isoforms. While TPM1 variant 6 (or isoform B7Z596) was clearly identified in the human serum samples, other TPM1 isoforms also could be present (See FIG. 3). Therefore, AELSEGQVR, aa147-155 of SEQ ID NO: 10, which was specific to TPM1v6, and three other peptides shared by several TPM1 isoforms and other TPM family members were used for MRM quantitation (see Table 1, and Table 6). Table 6 shows MRM peak areas for TPM1 peptides normalized and averaged in individual samples as an indication of the protein abundance level.

TABLE 6

| Sample | # | TPM1v6 LVIIESDLER, aa133-142 of SEQ ID NO: 10 | TPM1v6 AELSEGQVR, aa147-155 of SEQ ID NO: 10 | TPM1v6 ETAEADV ASLNR, aa43-54 of SEQ ID NO. 6 | TPM1v6 SLQEQAD AAEER, aa16-27 of SEQ ID NO: 10 | TPM1v6 Norm & Avg |
|---|---|---|---|---|---|---|
| Normal | WCS02 | 27232 | 74344 | 20979 | 11989 | 0.142 |
| Normal | WCS04 | 8305 | 80477 | 13397 | 9571 | 0.089 |
| Normal | WCS12 | 2975 | 54062 | 9440 | 6603 | 0.056 |
| Normal | WCS13 | 4094 | 41958 | 0 | 4239 | 0.033 |

TABLE 6-continued

| Sample | # | TPM1v6 LVIIESDLER, aa133-142 of SEQ ID NO: 10 | TPM1v6 AELSEGQVR aa147-155 of SEQ ID NO: 10 | TPM1v6 ETAEADV ASLNR, aa43-54 of SEQ ID NO. 6 | TPM1v6 SLQEQAD AAEER, aa16-27 of SEQ ID NO: 10 | TPM1v6 Norm & Avg |
|---|---|---|---|---|---|---|
| Normal | WCS14 | 44163 | 149293 | 40975 | 35597 | 0.287 |
| Normal | WCS15 | 11741 | 63033 | 15414 | 9777 | 0.093 |
| Benign | B23 | 47853 | 257616 | 51054 | 38261 | 0.357 |
| Benign | B25 | 14674 | 123609 | 30139 | 23165 | 0.175 |
| Benign | B70 | 46999 | 382365 | 66409 | 43960 | 0.440 |
| Benign | B77 | 101250 | 492555 | 105122 | 72337 | 0.713 |
| Benign | B79 | 50274 | 251060 | 48504 | 38126 | 0.355 |
| Benign | B80 | 145616 | 872565 | 306980 | 196336 | 1.542 |
| Benign | B81 | 45480 | 275283 | 60738 | 47356 | 0.395 |
| Benign | B82 | 53860 | 368472 | 128792 | 84337 | 0.638 |
| Benign | B83 | 56220 | 197314 | 86720 | 62744 | 0.500 |
| Cancer | T455 | 67782 | 428888 | 90666 | 64820 | 0.583 |
| Cancer | T474 | 181863 | 1122884 | 207117 | 179329 | 1.506 |
| Cancer | T475 | 50783 | 255305 | 45158 | 34454 | 0.344 |
| Cancer | T476 | 119220 | 523437 | 163132 | 86059 | 0.885 |
| Cancer | T478 | 120774 | 500688 | 118103 | 98305 | 0.832 |
| Cancer | T482 | 71530 | 313303 | 43307 | 31577 | 0.398 |
| Cancer | T536 | 431057 | 1930569 | 410941 | 320850 | 2.941 |
| Cancer | T539 | 104008 | 533374 | 123592 | 91636 | 0.806 |
| Cancer | T541 | 0 | 31284 | 0 | 0 | 0.012 |
| Cancer | T543 | 56020 | 257055 | 57840 | 44155 | 0.397 |
| Cancer | T553 | 209330 | 1191620 | 294342 | 236825 | 1.854 |
| Cancer | T556 | 279781 | 1873212 | 438823 | 361745 | 2.754 |
| Cancer | T557 | 140328 | 662386 | 164727 | 117159 | 1.048 |
| Cancer | T577 | 25267 | 233927 | 50457 | 44460 | 0.316 |
| Cancer | T600 | 69940 | 417227 | 96263 | 70731 | 0.605 |
| Cancer | T602 | 50571 | 210865 | 65650 | 51836 | 0.399 |
| Cancer | T603 | 234813 | 1190812 | 242276 | 167008 | 1.667 |
| Cancer | T604 | 57236 | 423975 | 125785 | 80801 | 0.652 |

We also attempted to target TPM2, TPM3, and TPM4, as products of these genes were also identified in the GeLC-MS/MS analysis of patient serum pools (Table 3). Of course, as is typically the case, strong, consistent, interference-free MRM signals could not be obtained for all desired peptides. The final MRM assay contained one peptide specific to TPM3, two peptides specific to TPM4, one peptide shared by TPM2 and TPM4, and one peptide shared by all four TPM genes (See Table 1 and Table 7). Table 7 shows MRM peak areas for TPM3 and TPM4 peptides normalized and averaged in individual samples as an indication of the protein abundance level.

TABLE 7

| Sample | # | TPM3 IQVLQQQ ADDAEER, SEQ ID NO: 12 | TPM3 Norm & Avg | TPM4 IQALQQQ ADEAEDR, SEQ ID NO: 14 | TPM4 AEGDV AALNR, SEQ ID NO: 13 | TPM4 KLVILE GELER, SEQ ID NO: 18 | TPM4 Norm & Avg |
|---|---|---|---|---|---|---|---|
| Normal | WCS02 | 37607 | 0.116 | 66530 | 657724 | 630468 | 0.110 |
| Normal | WCS04 | 62540 | 0.192 | 57080 | 425479 | 419663 | 0.079 |
| Normal | WCS12 | 11573 | 0.036 | 13120 | 179765 | 212806 | 0.030 |
| Normal | WCS13 | 0 | 0.000 | 0 | 70176 | 140492 | 0.012 |
| Normal | WCS14 | 44708 | 0.137 | 18371 | 173740 | 238804 | 0.034 |
| Normal | WCS15 | 23374 | 0.072 | 21477 | 215144 | 266941 | 0.039 |
| Benign | B23 | 50826 | 0.156 | 92784 | 769719 | 861540 | 0.144 |
| Benign | B25 | 31580 | 0.097 | 64680 | 592048 | 641548 | 0.106 |
| Benign | B70 | 215328 | 0.661 | 203602 | 1962777 | 1862029 | 0.331 |
| Benign | B77 | 205003 | 0.630 | 455168 | 3475540 | 3751568 | 0.660 |
| Benign | B79 | 113763 | 0.349 | 173730 | 1258455 | 1590148 | 0.257 |
| Benign | B80 | 651126 | 2.000 | 1431956 | 10630968 | 9275897 | 1.913 |
| Benign | B81 | 135085 | 0.415 | 167413 | 269426 | 1290576 | 0.237 |
| Benign | B82 | 533252 | 1.638 | 85394 | 681075 | 841789 | 0.134 |
| Benign | B83 | 210727 | 0.647 | 216592 | 1631897 | 1912271 | 0.320 |
| Cancer | T455 | 181883 | 0.559 | 329762 | 3198211 | 3703179 | 0.517 |
| Cancer | T474 | 385261 | 1.183 | 1033082 | 8868498 | 8154397 | 1.539 |
| Cancer | T475 | 78718 | 0.242 | 138849 | 1355419 | 1412261 | 0.235 |
| Cancer | T476 | 287108 | 0.882 | 740508 | 7091117 | 6861693 | 1.207 |
| Cancer | T478 | 163723 | 0.503 | 327030 | 2662922 | 2613253 | 0.480 |
| Cancer | T482 | 114583 | 0.352 | 264911 | 2633676 | 2720894 | 0.453 |
| Cancer | T536 | 876097 | 2.691 | 1796201 | 16550308 | 16225609 | 2.863 |
| Cancer | T539 | 249410 | 0.766 | 492600 | 3835421 | 3916627 | 0.711 |
| Cancer | T541 | 0 | 0.000 | 7022 | 47530 | 49422 | 0.009 |
| Cancer | T543 | 147454 | 0.453 | 143235 | 1017944 | 977404 | 0.191 |
| Cancer | T553 | 909385 | 2.793 | 1389863 | 8780337 | 10176023 | 1.830 |
| Cancer | T556 | 1070392 | 3.288 | 2182304 | 16019177 | 17806655 | 3.116 |
| Cancer | T557 | 394944 | 1.213 | 729285 | 6244945 | 7007301 | 1.157 |
| Cancer | T577 | 66040 | 0.203 | 126311 | 872615 | 987295 | 0.174 |
| Cancer | T600 | 191799 | 0.589 | 466198 | 4198007 | 6027998 | 0.842 |
| Cancer | T602 | 69239 | 0.213 | 168912 | 1430173 | 1592082 | 0.265 |
| Cancer | T603 | 477013 | 1.465 | 1191352 | 10077129 | 11834475 | 1.908 |
| Cancer | T604 | 197319 | 0.606 | 346242 | 2351772 | 2126914 | 0.442 |

Table 8 shows MRM peak areas for the TPM common peptide normalized in individual samples as an indication of the protein abundance level.

TABLE 8

| Sample | # | TPM RIQLVEEELDR, SEQ ID NO: 16 | TPM Norm & Avg |
|---|---|---|---|
| Normal | WCS02 | 716335 | 0.114 |
| Normal | WCS04 | 680639 | 0.108 |
| Normal | WCS12 | 273406 | 0.043 |
| Normal | WCS13 | 121600 | 0.019 |
| Normal | WCS14 | 519755 | 0.083 |
| Normal | WCS15 | 444269 | 0.071 |
| Benign | B23 | 1018792 | 0.162 |
| Benign | B25 | 784378 | 0.125 |
| Benign | B70 | 2396858 | 0.381 |
| Benign | B77 | 4183895 | 0.065 |
| Benign | B79 | 1122745 | 0.274 |
| Benign | B80 | 12378679 | 1.967 |
| Benign | B81 | 1384354 | 0.220 |
| Benign | B82 | 3515417 | 0.559 |
| Benign | B83 | 2601924 | 0.413 |
| Cancer | T455 | 3561471 | 0.566 |
| Cancer | T474 | 9345962 | 1.485 |
| Cancer | T475 | 1536987 | 0.244 |
| Cancer | T476 | 7037409 | 1.118 |
| Cancer | T478 | 3371869 | 0.536 |
| Cancer | T482 | 2992930 | 0.476 |
| Cancer | T536 | 17007129 | 2.702 |
| Cancer | T539 | 4446598 | 0.706 |
| Cancer | T541 | 148179 | 0.024 |
| Cancer | T543 | 1574956 | 0.250 |
| Cancer | T553 | 13973974 | 2.220 |
| Cancer | T556 | 19572892 | 3.110 |
| Cancer | T557 | 6989658 | 1.111 |
| Cancer | T577 | 1159454 | 0.184 |
| Cancer | T600 | 5455926 | 0.867 |
| Cancer | T602 | 1665550 | 0.265 |
| Cancer | T603 | 10720865 | 1.703 |
| Cancer | T604 | 2728471 | 0.434 |

Example 5

Quantitation of TPM and CLIC Isoforms in Patient Serum Samples

GeLC-MRM quantitation of the CLIC and TPM peptides and normalized protein values for individual patient samples are summarized in Tables 3-8. TPM peptide amounts were graphically compared across all serum samples as a first-level test of potential differences across patients in peptides specific for certain isoforms and those shared by multiple isoforms both within the TPM1 isoform group and across related gene products (See Table 3).

Similarly, the protein levels (normalized and averaged peptides values) across patient samples were compared as shown in FIG. 4. All the peptides monitored displayed similar quantitative profiles, although some minor variations were observed in some samples (See FIG. 4 and Table 3). Spearman's rank correlation coefficient analysis showed that all tropomyosin peptides analyzed here are highly correlated within each patient group with P-values<0.001 (data not shown), indicating a lack of evidence that specific tropomyosins differ from other family members and isoforms in being able to distinguish between ovarian cancer, benign disease, and normal donors. Also, if alternative TPM family proteins share some of the quantified peptides, their contribution is either minor or they track with the TPM proteins and isoforms quantitated here. Since the distribution of all tropomyosin peptides is similar, the peptide (K)LVI-LEGELER SEQ ID NO: 18 that is shared between TPM2 and TPM4 was assigned to TPM4 for the purpose of calculating the TPM4 protein level. In addition, factor analysis shows that all the tropomyosin proteins analyzed here are measuring the same factor (data not shown), which is consistent with the similar quantitative profiles shown in FIG. 4.

These data show that multiple TPM related proteins and isoforms thereof are present in human serum. At least in the current cohort, fluctuations in abundance levels related to benign ovarian disease and ovarian cancer for TPM family members and their isoforms appear to change in concert. However, it is possible that certain TPM isoforms may be more selective for specific clinical applications such as monitoring responses to different therapies or disease reoccurrence. Tropomyosin proteins are also known to be modified by post-translational modifications such as acetylation and phosphorylation, and the influence of post-translationally modified forms in ovarian cancer diagnosis has not yet been tested.

GeLC-MRM quantitative results for CLIC1 and CLIC4 peptide and protein levels also are shown in Tables 6 and 5, respectively. As expected, since the same patient samples were used, CLIC1 results were similar, but not identical, to the previously reported results in Tang et al, 2012, cited above, for this protein. There was some moderate variation because the two sets of label-free measurements were performed at different times and on two different instruments. That is, previous analyses were performed on an AB SCIEX 4000 QTRAP and the current results were from an AB SCIEX 5500 QTRAP instrument. The CLIC1 measurements were repeated here to provide a direct comparison to the newly identified biomarker CLIC4. For both CLIC proteins, all peptides from the same protein showed similar distributions among the individual patient samples (data not shown), indicating that the MRM signals used for quantitation were derived from the same protein and quantitation was not appreciably affected by interfering signals.

Example 6

CLIC and TPM Biomarkers can Distinguish EOC from Non-Cancer Cases

The capacities of the CLIC and TPM biomarkers to distinguish EOC cases were assessed in several ways using the GeLC-MRM quantitation data (See, Tables 4-8). A two-way comparison between the non-cancer (normal and benign) and cancer groups using the Mann-Whitney test showed that all isoforms could significantly distinguish ($P<0.05$) between cancer and non-cancer (see Table 9).

TABLE 9

GeLC-MRM comparison of non-cancer (normal and benign) versus cancer sera

| UniProt | Name | Descriptive Name | P-value[a] |
|---|---|---|---|
| O00299 | CLIC1 | Chloride intracellular channel protein 1 | 0.004 |
| Q9Y696 | CLIC4 | Chloride intracellular channel protein 4 | 0.0002 |
| Q1ZYL5 | TPM1, var. 6 | Tropomyosin 1 alpha variant 6 | 0.0052 |
| Q5VU59 | TPM3 | Tropomyosin 3 | 0.0337 |
| P67936 | TPM4 | Tropomyosin alpha-4 chain | 0.0021 |

NOTES
[a]P-values are from the Mann-Whitney test with Bonferroni adjustment

Based on the P-value, CLIC4 appeared to be the best biomarker in distinguishing cancer from non-cancer and TPM3 was the weakest biomarker.

For further evaluation, the normal and benign samples were compared separately to the cancer group (FIG. 5). All protein isoforms could distinguish between normal donors and ovarian cancer patients at a highly significant level ($P<0.0015$). However, CLIC4 was the only biomarker that showed a significant difference between benign disease and EOC.

The TPM isoforms did not show a statistically significant difference between benign disease and cancer primarily because a single benign sample (B80) had a much higher abundance level for all TPM isoforms than other samples in that group. Future analysis of larger cohorts will allow us to more definitively identify which proteins can reliably distinguish benign disease from ovarian cancer.

Although benign ovarian tumors and ovarian cancer appear to be very different diseases at a genetic level, a major challenge at the initial diagnosis stage in the clinic is to distinguish benign ovarian conditions from malignant ones.

To evaluate the potential diagnostic efficacy for each of these proteins, receiver operating characteristic (ROC) curve analyses were performed on the non-cancer and cancer groups (See FIG. 6). Consistent with the Mann-Whitney test, CLIC4 showed the largest area under the curve (AUC) and TPM3 showed the lowest area. It is anticipated that larger patient cohorts may support the use of CLIC4 and tropomyosin family proteins or isoforms, when used with other biomarkers simultaneously and in combination may outperform use of a single biomarker for detection and clinical monitoring of EOC.

To our knowledge, the plasma levels of CLIC4 and tropomyosin in ovarian cancer patients have not been reported previously.

It is anticipated that testing of the biomarkers and biomarkers sets described herein in larger cohorts of patients collected from different sites, longitudinal prediagnostic blood specimens, and specimens collected throughout therapeutic treatment will demonstrate results consistent with the above.

Each and every patent, patent application, and publication, including U.S. provisional patent application No. 61/709,695, the publications listed herein, and publically available peptide sequences, cited throughout the disclosure, is expressly incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

PUBLICATIONS

1. Siegel, R. et al, Cancer statistics, 2012. *CA Cancer J Clin* 2012, 62, (1), 10-29.
2. Cannistra, S. A., Cancer of the ovary. *N Engl J Med* 2004, 351, (24), 2519-29.
3. Mutch, D. G., Surgical management of ovarian cancer. *Semin Oncol* 2002, 29, (1 Suppl 1), 3-8.
4. Klug, T. L. et al, Monoclonal antibody immunoradiometric assay for an antigenic determinant (CA 125) associated with human epithelial ovarian carcinomas. *Cancer Res* 1984, 44, (3), 1048-53.
5. Anastasi, E. et al, HE4: a new potential early biomarker for the recurrence of ovarian cancer. *Tumour Biol* 2010, 31, (2), 113-9.
6. Zhang, Z. et al., Three biomarkers identified from serum proteomic analysis for the detection of early stage ovarian cancer. *Cancer Res* 2004, 64, (16), 5882-90.
7. Moore, R. G. et al, Comparison of a novel multiple marker assay vs the Risk of Malignancy Index for the prediction of epithelial ovarian cancer in patients with a pelvic mass. *Am J Obstet Gynecol* 2010, 203, (3), 228 e1-6.
8. Moss, E. L. et al, The role of CA125 in clinical practice. *J Clin Pathol* 2005, 58, (3), 308-12.
9. Nick, A. M.; Sood, A. K., The ROC 'n' role of the multiplex assay for early detection of ovarian cancer. *Nat Clin Pract Oncol* 2008, 5, (10), 568-9.
10. Gagne, J. P. et al, Proteome profiling of human epithelial ovarian cancer cell line TOV-112D. *Mol Cell Biochem* 2005, 275, (1-2), 25-55.
11. Dai, L. et al, Comparative proteomic study of two closely related ovarian endometrioid adenocarcinoma cell lines using cIEF fractionation and pathway analysis. *Electrophoresis* 2009, 30, (7), 1119-31.
12. Zhu, Y. et al, Classifications of ovarian cancer tissues by proteomic patterns. *Proteomics* 2006, 6, (21), 5846-56.
13. Bengtsson, S. et al, Large-scale proteomics analysis of human ovarian cancer for biomarkers. *J Proteome Res* 2007, 6, (4), 1440-50.
14. Gortzak-Uzan, L. et al, A proteome resource of ovarian cancer ascites: integrated proteomic and bioinformatic analyses to identify putative biomarkers. *J Proteome Res* 2008, 7, (1), 339-51.
15. Kuk, C. et al., Mining the ovarian cancer ascites proteome for potential ovarian cancer biomarkers. *Mol Cell Proteomics* 2009, 8, (4), 661-9.
16. Faca, V. M. et al, Proteomic analysis of ovarian cancer cells reveals dynamic processes of protein secretion and shedding of extra-cellular domains. *PLoS One* 2008, 3, (6), e2425.
17. Gunawardana, C. G. et al, Comprehensive analysis of conditioned media from ovarian cancer cell lines identi- 18. Wei, B. R. et al, Serum S100A6 concentration predicts peritoneal tumor burden in mice with epithelial ovarian cancer and is associated with advanced stage in patients. *PLoS One* 2009, 4, (10), e7670.
19. Pitteri, S. J. et al, Integrated proteomic analysis of human cancer cells and plasma from tumor bearing mice for ovarian cancer biomarker discovery. *PLoS One* 2009, 4, (11), e7916.
20. He, Y. et al, LC-MS/MS analysis of ovarian cancer metastasis-related proteins using a nude mouse model: 14-3-3 zeta as a candidate biomarker. *J Proteome Res* 2010, 9, (12), 6180-90.
21. Tang, H. Y. et al, A xenograft mouse model coupled with in-depth plasma proteome analysis facilitates identification of novel serum biomarkers for human ovarian cancer. *J Proteome Res* 2012, 11, (2), 678-91.
22. Anderson, L.; Hunter, C. L., Quantitative mass spectrometric multiple reaction monitoring assays for major plasma proteins. *Mol Cell Proteomics* 2006, 5, (4), 573-88.
23. Domon, B.; Aebersold, R., Options and considerations when selecting a quantitative proteomics strategy. *Nat Biotechnol* 2010, 28, (7), 710-21.
24. Sherman, J. et al, How specific is my SRM?: The issue of precursor and product ion redundancy. *Proteomics* 2009, 9, (5), 1120-3.
25. Duncan, M. W. et al, Quantifying proteins by mass spectrometry: the selectivity of SRM is only part of the problem. *Proteomics* 2009, 9, (5), 1124-7.
26. Nesvizhskii, A. I.; Aebersold, R., Interpretation of shotgun proteomic data: the protein inference problem. *Mol Cell Proteomics* 2005, 4, (10), 1419-40.
27. Rodriguez-Pineiro, A. M. et al, Differential expression of serum clusterin isoforms in colorectal cancer. *Mol Cell Proteomics* 2006, 5, (9), 1647-57.
28. Kriventseva, E. V. et al, Increase of functional diversity by alternative splicing. *Trends Genet* 2003, 19, (3), 124-8.
29. Garcia-Blanco, M. A. et al, Alternative splicing in disease and therapy. *Nat Biotechnol* 2004, 22, (5), 535-46.
30. Tang, H. Y. et al, Rapid Verification of Candidate Serological Biomarkers Using Gel-based, Label-free Multiple Reaction Monitoring. *J Proteome Res* 2011, 10, (9), 4005-17.
31. Beer, L. A. et al, Systematic discovery of ectopic pregnancy serum biomarkers using 3-D protein profiling coupled with label-free quantitation. *J Proteome Res* 2011, 10, (3), 1126-38.
32. Wang, H. et al, Data analysis strategy for maximizing high-confidence protein identifications in complex proteomes such as human tumor secretomes and human serum. *J Proteome Res* 2011, 10, (11), 4993-5005.
33. Gunning, P. W. et al, Tropomyosin isoforms: divining rods for actin cytoskeleton function. *Trends Cell Biol* 2005, 15, (6), 333-41.
34. Choi, C. et al, From skeletal muscle to cancer: insights learned elucidating the function of tropomyosin. *J Struct Biol* 2012, 177, (1), 63-9.
35. Yao, Q. et al, CLIC4 mediates TGF-beta1-induced fibroblast-to-myofibroblast transdifferentiation in ovarian cancer. *Oncol Rep* 2009, 22, (3), 541-8.
36. Shukla, A.; Yuspa, S. H., CLIC4 and Schnurri-2: a dynamic duo in TGF-beta signaling with broader implications in cellular homeostasis and disease. *Nucleus* 2010, 1, (2), 144-9.
37. Hellman, D. M.; Flynn, P.; Khan, P; Saeed, A., Tropomyosin as a regulator of cancer cell transformation. *Adv Exp Med Biol* 2008, 644, 124-31.
38. Raval, G. N. et al, Loss of expression of tropomyosin-1, a novel class II tumor suppressor that induces anoikis, in primary breast tumors. *Oncogene* 2003, 22, (40), 6194-203.
39. Chow, S. N. et al., Analysis of protein profiles in human epithelial ovarian cancer tissues by proteomic technology. *Eur J Gynaecol Oncol* 2010, 31, (1), 55-62.
40. Rostila, A. et al, Peroxiredoxins and tropomyosins as plasma biomarkers for lung cancer and asbestos exposure. *Lung Cancer* 2012, 77, (2), 450-9.
41. Lu, H. et al, Targeting serum antibody for cancer diagnosis: a focus on colorectal cancer. *Expert Opin Ther Targets* 2007, 11, (2), 235-44.
42. International Patent Application No. PCT/US2012/54136.

The invention claimed is:

1. A method for diagnosing or detecting or monitoring the progress or treatment of ovarian cancer in a subject comprising:
contacting a sample obtained from a test subject with a diagnostic reagent consisting of
 (a) a ligand capable of specifically complexing with, binding to, or quantitatively detecting or identifying the biomarker chloride intracellular channel protein 4 (CLIC4) or an isoform, pro-form, modified molecular form, posttranslational modification, or unique peptide fragment or unique nucleic acid fragment thereof;
 (b) a ligand capable of specifically complexing with, binding to, or quantitatively detecting or identifying the biomarker chloride intracellular channel protein 1 (CLIC1) or an isoform, pro-form, modified molecular form, posttranslational modification, or unique peptide fragment or unique nucleic acid fragment thereof; and
 (c) a ligand capable of specifically complexing with, binding to, or quantitatively detecting or identifying the biomarker cathepsin D-30 (CTSD-30) or an isoform, pro-form, modified molecular form, posttranslational modification, or unique peptide fragment or unique nucleic acid fragment thereof; and
one or more additional ligands, each additional ligand capable of specifically complexing with, binding to, or quantitatively detecting, or identifying an additional biomarker that indicates the presence of ovarian cancer in a human subject, wherein said additional biomarker is selected from:
 i. tropomyosin 1 (TPM1);
 ii. tropomyosin 2 (TPM2);
 iii. tropomyosin 3 (TPM3);
 iv. tropomyosin 4 (TPM4);
 v. proteasome subunit alpha type-7 (PSMA7)
 vi. CA125; and
 vii. HE4,
(ii) detecting or measuring in the sample or from a protein level profile generated from the sample, the protein levels of the selected biomarkers;
(iii) comparing the protein level of the selected biomarkers in the subject's sample with the level of the same biomarkers in a reference standard;
wherein a significant change in the protein level of one or more of the selected biomarkers in the subject's sample from that in the reference standard indicates a diagnosis, risk, or the status of progression or remission of ovarian cancer in the subject.

2. The method according to claim 1,
wherein an isoform of TPM1 is TPM1, variant 6 (UniProt ID No. Q1ZYL5) or TPM1, variant 8 (UniProt ID No. B7Z596);
wherein an isoform of TPM2 is TPM2 beta chain (UniProt ID No. UR1H_P07951, UR1H_Q5TCU3, or UR1H_Q5TCU8) or TPM2, isoform 2 (UniProt ID No. P07951-2, A7XZE4), wherein an isoform of TPM3 is TPM3 alpha-3 chain (UniProt ID No. P06753, Q5VU59, Q5HYB6, B2RDE1, or E2RB38); or wherein an isoform of TPM4 is TPM4 alpha-4 chain (UniProt ID No. P6736), or TPM4, Isoform 2 (UniProt ID No. P67936-2).

3. The method according to claim 1, further comprising: detecting or measuring in the sample or from a protein level profile generated from the sample, the protein levels of one or more additional ovarian cancer biomarkers; and comparing the protein levels of the additional biomarkers in relation to the levels of the additional biomarkers in the subject's sample with the same biomarkers in a reference standard or profile.

4. The method according to claim 3, wherein the reference standard is a mean, an average, a numerical mean or range of numerical means, a numerical pattern, a ratio, a graphical pattern or a protein level profile derived from the same biomarker or biomarkers in a reference subject or reference population.

5. The method according to claim 3, wherein the additional biomarker is CA125, or an isoform, pro-form, modified molecular form, or unique peptide fragment therefrom; or HE4, or an isoform, pro-form, modified molecular form, or unique peptide fragment therefrom.

6. The method according to claim 1, wherein said change in the protein level of each said biomarker comprises an increase in comparison to said reference or control or a decrease in comparison to said reference or control.

7. The method according to claim 1, wherein said diagnosis comprises early diagnosis of disease, monitoring relapse after initial diagnosis and treatment, predicting clinical outcome, or determining the best clinical treatment.

8. The method according to claim 1, wherein the biological sample is selected from group consisting of whole blood, plasma, serum, circulating tumor cells, ascites fluid, peritoneal fluid and tumor tissue or tissue or fluid from a biopsy sample, surgical sample, or tumor cell sample.

9. The method according to claim 1, wherein the biomarker CLIC4 is Uniprot ID no. Z9Y696 or a peptide fragment thereof.

10. The method according to claim 9, wherein the CLIC4 peptide fragment comprises:

```
(a)
aa 49-60 of SEQ ID NO: 1
GVVFSVTTVDLK,;

(b)
aa 151-172 of SEQ ID NO: 1
LDEYLNSPLPDEIDENSMEDIK,;
```

```
-continued
(c)
aa 131-142 of SEQ ID NO: 1
NSRPEANEALER,;

(d)
aa 20-27 of SEQ ID NO: 1
YLTNAYSR,;

(d)
aa 139-249 of SEQ ID NO: 1
EVEIAYSDVAK,;

(e)
aa 41-48 of SEQ ID NO: 1
LFMILWLK,;

(f)
aa 228-238 of SEQ ID NO: 1
DEFTNTCPSDK,;

(g)
aa 91-103 of SEQ ID NO: 1
IEEFLEEVLCPPK,;

(h)
aa 178-194 of SEQ ID NO: 1
FLDGNEMTLADCNLLPK,;

(i)
aa 12-24 of SEQ ID NO: 1
EEDKEPLIELFVK,;
or (j)
aa 111-124 of SEQ ID NO: 1
HPESNTAGMDIFAK,;
``` wherein in each sequence where methionine occurs, it is in the oxidized or unoxidized form.

11. The method according to claim 1, wherein the CLIC1 peptide fragment comprises:

```
(a)
aa 38-49 of SEQ ID NO: 3;
GVTFNVTTVDTK, (b)
aa 96-113 of SEQ ID NO: 3;
LAALNPESNTAGLDIFAK,
or (c)
aa 120-131 of SEQ ID NO: 3
NSNPALNDNLEK,.
```

12. The method according to claim 1, wherein any of said ligands comprises an antibody or fragment of an antibody, an antibody mimic, a synthetic antibody, a single chain antibody or an equivalent that binds to or complexes with a single biomarker.

* * * * *